United States Patent
Kock et al.

(10) Patent No.: US 10,674,688 B2
(45) Date of Patent: Jun. 9, 2020

(54) *PERONOSPORA* RESISTANCE IN *SPINACIA OLERACEA*

(71) Applicant: RIJK ZWAAN ZAADTEELT EN ZAADHANDEL B.V., De Lier (NL)

(72) Inventors: Vincent Laurens Adrianus Kock, De Lier (NL); Johannes Geert Jan Feitsma, De Lier (NL); Raoul Jacobus Johannes Maria Frijters, De Lier (NL)

(73) Assignee: RIJK ZWAAN ZAADTEELT EN ZAADHANDEL B.V., De Lier (NL)

(*) Notice: Subject to any disclaimer, the term of this patent is extended or adjusted under 35 U.S.C. 154(b) by 0 days.

(21) Appl. No.: 15/720,760

(22) Filed: Sep. 29, 2017

(65) Prior Publication Data

US 2019/0110422 A1    Apr. 18, 2019

(51) Int. Cl.
A01H 5/12      (2018.01)
A01H 6/02      (2018.01)
C07K 14/415    (2006.01)

(52) U.S. Cl.
CPC ............... *A01H 5/12* (2013.01); *A01H 6/028* (2018.05); *C07K 14/415* (2013.01)

(58) Field of Classification Search
None
See application file for complete search history.

(56) References Cited

U.S. PATENT DOCUMENTS

| | | | |
|---|---|---|---|
| 9,265,275 B2 | 2/2016 | Den Braber | |
| 9,402,363 B1* | 8/2016 | Feitsma | C12Q 1/6895 |
| 10,017,781 B2 | 7/2018 | Torjek et al. | |
| 2005/0183150 A1 | 8/2005 | Torisky et al. | |
| 2009/0300786 A1* | 12/2009 | Baerends | A01H 5/12 800/268 |
| 2013/0230635 A1* | 9/2013 | Den Braber | A01H 1/04 426/615 |
| 2017/0027126 A1* | 2/2017 | Dijkstra | A01H 1/04 |
| 2017/0027127 A1* | 2/2017 | Dijkstra | A01H 6/028 |
| 2019/0127753 A1* | 5/2019 | Kock | C12N 15/8282 |

FOREIGN PATENT DOCUMENTS

| | | |
|---|---|---|
| DE | 10 2013 010 026 A1 | 12/2014 |
| EP | 2 848 114 A1 | 3/2015 |
| EP | 2 912 940 A1 | 9/2015 |
| WO | 2015/036469 A1 | 3/2015 |

OTHER PUBLICATIONS

Qi & Innes (2013) Front Immunol 4:348.*
Bentham et al. (2017) Annals Bot 119:689-702.*
Sukarta et al. (2016) Sem Cell Devol Biol 56:134-49.*
Dodds et al. (2001) Plant Cell 13:163-78.*
Chakraborty et al. (2018) Plant Sci 269:85-93.*
Eitas & Dangl (2010) Curr Opin Plant Biol 13:472-77.*
Irish et al. (2008) Phytopath 90(8):894-900.*
Correll et al. (2011) Eur J Plant Pathol 129:193-205.*
Irish et al. (2007) Plant Dis 91:1392-96.*
She et al. (2018) Theor Appl Genet 131:2529-41.*
Guo et al. (2004) Proc Natl Acad Sci USA 101:9205-10.*
Feng Chunda, et al., Construction of a Spinach Bacterial Artificial Chromosome (BAC) Library as a Resource for Gene Identification and Marker Development, Plant Molecular Biology Reporter (May 16, 2015) vol. 33, No. 6, p. 1996-2005.

* cited by examiner

*Primary Examiner* — Russell T Boggs
(74) *Attorney, Agent, or Firm* — Duane Morris LLP; Thomas J. Kowalski; Deborah L. Lu

(57) ABSTRACT

The present invention relates to an allele designated alpha-WOLF 8 which confers resistance to at least one *Peronospora farinosa* f. sp. *spinaciae* race, wherein the protein encoded by said allele is a CC-NB S-LRR protein that comprises in its amino acid sequence: a) the motif "MAEIGYSVC" (SEQ ID NO: 15) at its N-terminus; and b) the motif "KWMCLR" (SEQ ID NO: 16); and wherein the LRR domain of the protein has in order of increased preference at least 92%, 93%, 94%, 95%, 96%, 97%, 98%, 99%, 100% sequence similarity to SEQ ID NO: 12. When the allele is homozygously present in a spinach plant confers complete resistance to *Peronospora farinosa* f. sp. *spinaciae* races Pfs:1, Pfs:2, Pfs:6, Pfs:8 and Pfs:15, and confers intermediate resistance to Pfs:5, Pfs:10 and Pfs:16, and does not confer resistance to Pfs:3, Pfs:4, Pfs:7, Pfs:9, Pfs:11, Pfs:12, Pfs:13 and Pfs:14.

54 Claims, No Drawings
Specification includes a Sequence Listing.

PERONOSPORA RESISTANCE IN SPINACIA OLERACEA

RELATED APPLICATIONS AND INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on May 4, 2018, is named 43104002321_Correctedsequencelisting.txt and is 69,059 bytes in size.

FIELD OF THE INVENTION

The invention relates to an allele capable of conferring resistance to a spinach plant against multiple *Peronospora farinosa* f. sp. *spinaciae* races. The invention also relates to a spinach plant, to propagation material of said spinach plant, to a cell of said spinach plant, and to seed of said spinach plant carrying the allele. The invention further relates to a method of producing a spinach plant carrying the allele and to the use of the allele in breeding to confer resistance against *Peronospora farinosa* f. sp. *Spinaciae*.

BACKGROUND OF THE INVENTION

Downy mildew (*Peronospora farinosa* f. sp. *spinaciae*) is a major threat for spinach growers because it directly affects the harvested leaves. In spinach, downy mildew is caused by the oomycete *Peronospora farinosa* f. sp. *spinaciae* (formerly known as *P. effusa*). Infection makes the leaves unsuitable for sale and consumption, as it manifests itself phenotypically as yellow lesions on the older leaves, and on the abaxial leaf surface a greyish fungal growth can be observed. The infection can spread very rapidly, and it can occur both in glasshouse cultivation and in soil cultivation. The optimal temperature for formation and germination of *P. farinosa* f. sp. *spinaciae* spores is 9 to 12° C., and it is facilitated by a high relative humidity. When spores are deposited on a humid leaf surface they can readily germinate and infect the leaf. Fungal growth is optimal between 8 and 20° C. and a relative humidity of ≥80%, and within 6 and 13 days after infection mycelium growth can be observed. Oospores of *P. farinosa* can survive in the soil for up to 3 years, or as mycelium in seeds or living plants.

To date 16 pathogenic races of spinach downy mildew (Pfs) have been officially identified and characterized, and many new candidates are observed in the field. The 16 officially recognised races of *Peronospora farinosa* f. sp. *spinaciae*, are designated Pfs:1 to Pfs:16 (Irish et al. Phtypathol. Vol. 98 pg. 894-900, 2008; Plantum NL (Dutch association for breeding, tissue culture, production and trade of seed and young plants) press release, "Benoeming van Pfs: 14, een nieuwe fysio van valse meeldauw in spinazie", Sep. 19, 2012; Report Jim Correl (Univ. Arkansas) and Steven Koike (UC Cooperative Extension, Monterey County), "Race Pfs: 14—Another new race of the spinach downy mildew pathogen", Sep. 18, 2012; Plantum NL press release, "Denomination of Pfs: 15, a new race of downy mildew in spinach", Sep. 2, 2014, Plantum NL press release, "Denomination of Pfs: 16, a new race of downy mildew in spinach, Mar. 15, 2016). Races 4 to 15 were identified between 1990 and 2014, while only recently another new *Peronospora* isolate has been identified, termed UA201519B, which subsequently has been officially named Pfs:16 by the International Working Group on *Peronospora* (IWGP) (Plantum NL (Dutch association for breeding, tissue culture, production and trade of seed and young plants) press release, "Denomination of Pfs: 16, a new race of downy mildew in spinach", Mar. 15, 2016. All 16 officially recognized Pfs races are publicly available from the Department of Plant Pathology, University of Arkansas, Fayetteville, Ark. 72701, USA, and also from NAK Tuinbouw, Sotaweg 22, 2371 GD Roelofarendsveen, the Netherlands.

Especially the latest identified *Peronospora* races can break the resistance of many spinach varieties that are currently used commercially worldwide, and they thus pose a serious threat to the productivity of the spinach industry. Therefore, it is crucial to stay at the forefront of developments in this field, as *Peronospora* continuously develops the ability to break the resistances that are present in commercial spinach varieties. For this reason new resistance genes against downy mildew are very valuable assets, and they form an important research focus in breeding and particular in spinach and lettuce breeding. One of the main goals of spinach breeders is to rapidly develop spinach varieties with a resistance to as many *Peronospora* races as possible, including the latest identified races, before these races become wide-spread and pose a threat to the industry.

In commercial spinach varieties resistance against downy mildew is usually caused by so-called R-genes. R-gene mediated resistance is based on the ability of a plant to recognize the invading pathogen. In many cases this recognition occurs after the pathogen has established the first phases of interaction and transferred a so called pathogenicity (or avirulence) factor into the plant cell. These pathogenicity factors interact with host components in order to establish conditions which are favorable for the pathogen to invade the host and thereby cause disease. When a plant is able to recognize the events triggered by the pathogenicity factors a resistance response can be initiated. In many different plant pathogen interaction systems such as the interaction of spinach with different downy mildew strains, the plant initiates these events only after specific recognition of the invading pathogen.

Co-evolution of plant and pathogen has led to an arms race in which a R-gene mediated resistance is sometimes overcome as a consequence of the capability of the pathogen to interact with and modify alternative host targets or the same targets in a different way, such that the recognition is lost and infection can be established successfully resulting in disease. In order to re-establish resistance in a plant, a new R-gene has to be introduced which is able to recognize the mode of action of an alternative pathogenicity factor.

Despite the fact that the durability of R-genes is relatively low, R-genes are in spinach still the predominant form of defense against downy mildew. This is mainly due to the fact that it is the only form of defense that gives absolute resistance. So far plant breeders have been very successful in generating downy mildew resistant spinach varieties by making use of resistance genes residing in the wild germplasm of the crop species. Even though R-genes are extensively used in spinach breeding, until now not much is known of these R-genes. The R-genes present in the current commercial spinach varieties have never been characterized at the molecular level, i.e. their sequence until now was unknown. Also up until now there are no closely linked molecular markers known in the art that separate these R-genes, nor are the molecular characteristics of the genes themselves known in the art. Therefore, the search for new R-genes and R-gene identification is currently based on phenotypic assays in which many accessions are screened for possible variation in their resistance pattern. Subsequently it has to be determined through crossing and selection whether a newly observed resistance is in fact caused by an R-gene.

Citation or identification of any document in this application is not an admission that such document is available as prior art to the present invention.

SUMMARY OF THE INVENTION

Adequately responding to newly emerging downy mildew races is crucial for developing commercially successful spinach varieties. Therefore, it is the object of the invention to provide a new resistance allele conferring resistance to a newly emerged downy mildew isolate and to provide molecular biological tools for identifying this new resistance allele.

In the research leading to the present invention, it was found that different resistance genes that confer resistance to *Peronospora farinosa* f. sp. *spinaciae* in spinach are not separate resistance loci, as had been previously assumed, but that they are different alleles of the same one or two genes. These one or two genes, which are either "alpha-WOLF" type or "beta-WOLF" type genes (together referred to as "the WOLF genes") each encode a protein that belongs to the CC-NBS-LRR family (Coiled Coil—Nucleotide Binding Site—Leucine-Rich Repeat). Depending on the allelic variant (or the allelic variants) that is (are) present in a spinach plant, said plant will produce a variant of the WOLF protein that confers a certain resistance profile to pathogenic races of *Peronospora farinosa* f. sp. *spinaciae*. The research leading to the present invention has furthermore elucidated the relationship between the different alleles present in the genome of a spinach plant and the resistance profile of said plant to a number of different pathogenic races of *Peronospora farinosa* f. sp. *spinaciae*.

In the context of this invention the term "allele" or "allelic variant" is used to designate a version of the gene that is linked to a specific phenotype, i.e. resistance profile. It was found that a spinach plant may carry one or two WOLF genes. Each of these two WOLF genes encompasses multiple alleles, each allele conferring a particular resistance profile. The beta WOLF gene is located on scaffold12735 (sequence: GenBank: KQ143339.1), at position 213573-221884. In case the spinach plant also carries or only carries the alpha-WOLF gene, the alpha-WOLF gene is located at approximately the same location as where the beta-WOLF gene is located on scaffold12735 in the Viroflay genome assembly.

A screen for novel WOLF-alleles in the spinach germplasm identified a new allele of the alpha-WOLF gene conferring a new and unique resistance profile against several downy mildew races including the recently identified race Pfs:16.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Seeds of a plant 16R.58468 that comprises the alpha-WOLF 8 allele of the invention in its genome were deposited with NCIMB Ltd, Ferguson Building, Craibstone Estate, Bucksburn, Aberdeen AB21 9YA, UK, on Sep. 9 2016, under deposit accession number 42646. The deposit was made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

A genome assembly for spinach variety Viroflay—which is susceptible to all known pathogenic races of *Peronospora farinosa* f. sp. *spinaciae*—is publicly available (*Spinacia oleracea* cultivar SynViroflay, whole genome shotgun sequencing project; Bioproject: PRJNA41497; GenBank: AYZV00000000.2; BioSample: SAMN02182572, see also Dohm et al, 2014, Nature 505: 546-549). In this genome assembly for Viroflay, the beta-WOLF gene is located on scaffold12735 (sequence: GenBank: KQ143339.1), at position 213573-221884. The sequence covered by this interval comprises the entire genomic sequence of the beta-WOLF gene of Viroflay, plus 2000 basepairs sequence upstream from the gene, plus the sequence downstream from the gene, up to the locus of the neighbouring gene that is situated downstream from the WOLF gene. Spinach variety Viroflay only possesses a single WOLF gene, namely a beta-WOLF gene, but most other spinach lines harbor a single alpha-type WOLF gene at the same location in the genome. Other spinach lines harbor two WOLF genes at approximately the same location in the genome. In such cases, the two WOLF genes are positioned adjacent to each other. In most spinach lines that harbor two WOLF genes, one of said WOLF genes belongs to the alpha-type, and the other WOLF gene belongs to the beta-type. In the research leading to the present invention, it was observed that this allelic variation in the WOLF locus is responsible for differences in resistance to pathogenic races of *Peronospora farinosa* f. sp. *spinaciae*.

The difference between an allele of an alpha-WOLF gene and an allele of a beta-WOLF gene lies in the presence of specific conserved amino acid motifs in the encoded protein sequence. As mentioned above, all WOLF proteins possess—from N- to C-terminus—the following domains that are generally known in the art: a coiled coil domain (RX-CC-like, cd14798), an NBS domain (also referred to as "NB-ARC domain", pfam00931; van der Biezen & Jones, 1998, *Curr. Biol.* 8: R226-R228), and leucine-rich repeats (IPR032675) which encompass the LRR domain. In addition, all WOLF proteins comprise in their amino acid sequence the motif "MAEIGYSVC" (SEQ ID NO:15) at the N-terminus. In addition to this, all alpha-WOLF proteins comprise the motif "KWMCLR" (SEQ ID NO:16) in their amino acid sequence, whereas all beta-WOLF proteins comprise the motif "HVGCVVDR" (SEQ ID NO:17) in their amino acid sequence.

The present invention relates to a new *Peronospora farinosa* f. sp. *spinaciae* resistance conferring allele of the alpha-WOLF gene designated alpha-WOLF 8.

In particular, the invention relates to a *Peronospora farinosa* f. sp. *spinaciae* resistance conferring allele designated alpha-WOLF 8 wherein the protein encoded by said allele is a CC-NBS-LRR protein that may comprise in its amino acid sequence: a) the motif "MAEIGYSVC" (SEQ ID NO:15) at its N-terminus; and b) the motif "KWMCLR" (SEQ ID NO:16); and wherein the LRR domain of the protein has in order of increased preference at least 92%, 93%, 94%, 95%, 96%, 97%, 98%, 99%, 100% sequence similarity to SEQ ID NO:12. Optionally, the alpha WOLF 8 allele may further comprise an additional motif in their amino acid sequence, namely "DQEDEGEDN" (SEQ ID NO:18).

For the purpose of this invention, the LRR domain of the protein of the alpha-WOLF 8 allele is defined as the amino acid sequence that in order of increased preference has at least 92%, 93%, 94%, 95%, 96%, 97%, 98%, 99%, 100% sequence similarity to SEQ ID NO:12.

The skilled person is familiar with methods for the calculation of sequence similarity. Suitably sequence similarity is calculated using EMBOSS stretcher 6.6.0, using the EBLOSUM62 matrix and the resulting "similarity score".

The LRR domain of the alpha-WOLF 8 allele as defined herein can be determined by amplifying and sequencing the genomic DNA encoding for the amino acid sequence of LRR domain using specific primers, and subsequently translating the DNA sequence into an amino acid sequence, thereby applying common sense in choosing the correct reading frame. The skilled person is capable of doing this, using freely available online bioinformatics tools.

The genomic sequence of a LRR domain of an alpha-WOLF gene such as alpha-WOLF 8 can be amplified using a primer pair having a forward primer which is a nucleic acid molecule having the sequence of SEQ ID NO:8 and a reverse primer which is a nucleic acid molecule having the sequence of SEQ ID NO:9.

PCR conditions for amplifying the LRR domain-encoding region of an alpha-WOLF gene using primers having SEQ ID NO:8 and SEQ ID NO:9 are, using Platinum Taq enzyme (Thermo Fisher Scientific): 3 minutes at 95° C. (initial denaturing step); 40 amplification cycles, each cycle consisting of: 30 seconds denaturation at 95° C., 30 seconds annealing at 60° C., and 30 seconds extension at 72° C.; 2 minutes at 72° C. (final extension step).

The LRR domain of a beta-WOLF gene, e.g. the null allele as present in variety Viroflay, can be amplified using a forward primer which is a nucleic acid molecule having the sequence of SEQ ID NO:10 and a reverse primer which is a nucleic acid molecule having the sequence of SEQ ID NO:9.

PCR conditions for amplifying the LRR domain-encoding region of a beta-WOLF gene using primers having SEQ ID NO:9 and SEQ ID NO:10 are as follows, using Platinum Taq enzyme (Thermo Fisher Scientific):—3 minutes at 95° C. (initial denaturing step); 40 amplification cycles, each cycle consisting of: 30 seconds denaturation at 95° C., 50 seconds annealing at 58° C. and 50 seconds extension at 72° C.; 2 minutes at 72° C. (final extension step).

Therefore, the invention also relates to a primer pair for amplifying the LRR domain of an alpha-WOLF gene, more in particular for amplifying the LRR domain of an alpha-WOLF 8 allele wherein the forward primer is a nucleic acid molecule having the sequence of SEQ ID NO:8 and the reverse primer which is a nucleic acid molecule having the sequence of SEQ ID NO:9. The primers disclosed herein have been specifically designed for selectively amplifying part of a WOLF gene, and not of any other CC-NBS-LRR protein-encoding genes.

The invention relates to an alpha-WOLF 8 allele which has a genomic sequence that in order of increased preference has at least 80%, 81%, 82%, 83%, 84%, 85%. 86%, 87%, 88%, 89%, 90%, 91%, 92%, 93%, 94%, 95%, 96%, 97%, 98%, 99%, 100% sequence similarity to SEQ ID NO:1.

The invention relates to three different splice variants. In one embodiment, the invention relates to an alpha-WOLF 8 allele which has a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:2. This is the first splice variant of the alpha-WOLF 8 allele.

In a further embodiment the alpha-WOLF 8 allele has a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:3. This is the second splice variant.

In another embodiment the alpha-WOLF 8 allele has a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:4. This is the third splice variant.

In a further aspect of the invention the alpha-WOLF 8 allele encodes for a protein having an amino acid sequence which in order of increased preference has at least 92%, 93%, 94%, 95%, 96%, 97%, 98%, 99%, 100% sequence similarity to SEQ ID NO:5.

In another embodiment the alpha-WOLF 8 allele encodes for a protein having an amino acid sequence which in order of increased preference has at least 92%, 93%, 94%, 95%, 96%, 97%, 98%, 99%, 100% sequence similarity to SEQ ID NO:6.

In yet a further embodiment the alpha-WOLF 8 allele encodes for a protein having an amino acid sequence which in order of increased preference has at least 92%, 93%, 94%, 95%, 96%, 97%, 98%, 99%, 100% sequence similarity to SEQ ID NO:7.

The alpha-WOLF 8 allele when homozygously present in a spinach plant confers complete resistance to the officially recognized *Peronospora farinosa* f. sp. *spinaciae* races Pfs:1, Pfs:2, Pfs:6, Pfs:8 and Pfs:15, and confers intermediate resistance to Pfs:5, Pfs:10 and Pfs:16, and does not confer resistance to downy mildew races Pfs:3, Pfs:4, Pfs:7, Pfs:9, Pfs:11, Pfs:12, Pfs:13 and Pfs:14 (See Table 1). As indicated in Table 1, a spinach plant heterozygous for the alpha-WOLF 8 allele and not carrying any other resistance conferring allele will be susceptible for downy mildew races Pfs:5, Pfs:10, and Pfs:16.

The resistance of a spinach plant against one or more races of *Peronospora farinosa* f. sp. *Spinaciae* can be determined using a seedling test. Herein, a seedling test is defined as a test wherein spinach plants are planted in trays containing growth medium, optionally fertilized twice a week after seedling emergence. Plants were inoculated at the first true leaf stage with a sporangial suspension having a concentration of approximately $2.5 \times 10^5$/ml of one of the pathogenic races of *Peronospora farinosa* f. sp. *spinaciae* or isolates to be tested. The inoculated plants are placed in a dew chamber at 18° C. with 100% relative humidity for a 24 h period, and then moved to a growth chamber at 18° C. with a 12 h photoperiod for 6 days. After 6 days, the plants are returned to the dew chamber for 24 h to induce sporulation, and subsequently scored for a disease reaction. Preferably, 30 plants per race are tested.

As used herein, a plant is completely resistant against a *Peronospora farinosa* f. sp. *spinaciae* race when a plant shows no symptoms in the seedling test described herein.

As used herein, a plant is intermediately resistant against a *Peronospora farinosa* f. sp. *spinaciae* race when a plant shows only symptoms of chlorosis, or sporulation occurring only on the tips of the cotyledons in the seedling test described herein.

As used herein, a plant is susceptible to an isolate of a *Peronospora farinosa* f. sp. *spinaciae* race when a plant shows more than only symptoms of chlorosis, or when sporulation occurs on area larger than only the tips of the cotyledons in the seedling test described herein.

Another aspect of the invention relates to a spinach plant, which may comprise the alpha-WOLF 8 allele of invention, of which a representative sample of seed was deposited with the NCIMB under NCIMB accession number 42646.

In a further embodiment the plant of the invention which may comprise the alpha-WOLF 8 allele is an agronomically elite spinach plant.

In the context of this invention an agronomically elite spinach plant is a plant having a genotype that results into an accumulation of distinguishable and desirable agronomic traits which allow a producer to harvest a product of commercial significance, preferably the agronomically elite spinach plant which may comprise the alpha-WOLF 8 allele is a plant of an inbred line or a hybrid.

As used herein, a plant of an inbred line is a plant of a population of plants that is the result of three or more rounds of selfing, or backcrossing; or which plant is a double haploid. An inbred line may e.g. be a parent line used for the production of a commercial hybrid.

As used herein, a hybrid plant is a plant which is the result of a cross between two different plants having different genotypes. More in particular, a hybrid plant is the result of a cross between plants of two different inbred lines, such a hybrid plant may e.g. be a plant of an $F_1$ hybrid variety.

A plant carrying the alpha-WOLF 8 allele in heterozygous form may further comprise a beta-WOLF 0 allele as e.g. present in variety Viroflay wherein the beta-WOLF 0 allele does not confer any resistance to downy mildew. However, a plant heterozygous for the alpha-WOLF 8 allele may further comprise an allele of the alpha/beta-WOLF gene that does provide resistance to downy mildew. Preferably, such an allele would complement the alpha-WOLF 8 allele such that the spinach plant will be at least intermediately resistant to one or more other races to which the alpha-WOLF 8 allele does not provide resistance. Most preferably the other allele of the alpha/beta-WOLF gene complements the alpha-WOLF 8 allele such that the plant is resistant to *Peronospora farinosa* f. sp. *spinaciae* races Pfs:1 to Pfs:16. In one embodiment such a plant is an agronomically elite plant.

Alternatively, the resistance profile of a plant carrying the alpha-WOLF 8 allele is complemented by a resistance conferring allele of a totally different gene. Examples of such genes are e.g. DMR1 as described in U.S. Pat. No. 8,354,570 and DMR6 as described in U.S. Pat. No. 9,121,029.

The invention thus relates to a spinach plant carrying the alpha-WOLF 8 allele and may further comprise a genetic determinant resulting in resistance against *Peronospora farinosa* f. sp. *spinaciae* races Pfs:1 to Pfs:16. The genetic determinant can be another resistance conferring alpha/beta-WOLF allele or a resistance conferring allele of a totally different gene.

The invention further relates to propagation material which may comprise the alpha-WOLF 8 allele. In one embodiment, the propagation material is suitable for sexual reproduction. Such propagation material may comprise for example a microspore, pollen, ovary, ovule, embryo sac and egg cell. In another embodiment, the propagation material is suitable for vegetative reproduction. Such propagation material may comprise for example a cutting, root, stem, cell, protoplast, and a tissue culture of regenerable cells. A part of the plant that is suitable for preparing tissue cultures is in particular a leaf, pollen, an embryo, a cotyledon, a hypocotyl, a meristematic cell, a root tip, an anther, a flower, a seed and a stem.

The invention furthermore relates to a cell of a spinach plant which may comprise the alpha-WOLF 8 allele. Such a cell may be either in isolated form or may be part of the complete plant or parts thereof and then still constitutes a cell of the invention because such a cell harbors the alpha-WOLF 8 allele that confers resistance to downy mildew. Each cell of a plant of the invention carries the genetic information that confers resistance to *Peronospora farinosa* f. sp. *spinaciae*. Such a cell of the invention may also be a regenerable cell that can be used to regenerate a new plant which may comprise the allele of the invention.

Yet another aspect of the invention relates to a method for making a hybrid spinach seed which may comprise crossing a first parent spinach plant with a second parent spinach plant and harvesting the resultant hybrid spinach seed, wherein said first and/or second parent spinach plant may comprise the alpha-WOLF 8 allele. In particular embodiment, the first and/or second parent plant is a plant of an inbred line as defined herein.

The invention further relates hybrid spinach plant grown from seed produced by crossing a first parent spinach plant with a second parent spinach plant and harvesting the resultant hybrid spinach seed, wherein said first and/or second parent spinach plant may comprise the alpha-WOLF 8 allele.

Another aspect of the invention relates to a method for identifying or selecting a spinach plant carrying the alpha-WOLF 8 allele, which may comprise determining the presence of a genomic nucleotide sequence or a part thereof in the genome of a plant, wherein said sequence has in order of increased preference 92%, 93%, 94%, 95%, 96%, 97%, 98%, 99%, 100% sequence similarity to SEQ ID NO:1.

The invention further relates a method for identifying or selecting a spinach plant carrying the alpha-WOLF 8 allele, which may comprise determining the presence of a coding sequence or a part thereof in the genome of a plant, wherein said sequence has in order of increased preference 92%, 93%, 94%, 95%, 96%, 97%, 98%, 99%, 100% sequence similarity to SEQ ID NO:2.

The invention further relates a method for identifying or selecting a spinach plant carrying the alpha-WOLF 8 allele, which may comprise determining the presence of a coding sequence or a part thereof in the genome of a plant, wherein said sequence has in order of increased preference 92%, 93%, 94%, 95%, 96%, 97%, 98%, 99%, 100% sequence similarity to SEQ ID NO:3.

The invention further relates a method for identifying or selecting a spinach plant carrying the alpha-WOLF 8 allele, which may comprise determining the presence of a coding sequence or a part thereof in the genome of a plant, wherein said sequence has in order of increased preference 92%, 93%, 94%, 95%, 96%, 97%, 98%, 99%, 100% sequence similarity to SEQ ID NO:4.

Determining the genomic DNA or coding DNA sequence of at least part of a WOLF gene in the genome of a spinach plant may be performed using any suitable molecular biological method known in the art, including but not limited to (genomic) PCR amplification followed by Sanger sequencing, whole-genome-sequencing, transcriptome sequencing, sequence-specific target capture followed by next-generation sequencing (using, for example, the xGen® target capture system of Integrated DNA Technologies), specific amplification of LRR-domain which may comprise gene sequences (using, for example, the RenSeq methodology, as described in U.S. patent application Ser. No. 14/627,116, and in Jupe et al., 2013, *Plant J.* 76: 530-544) followed by sequencing, etcetera.

In another embodiment the invention relates to a method for identifying or selecting a plant carrying the alpha-WOLF 8 allele which may comprise determining the DNA sequence coding for the LRR domain as defined herein.

In a further embodiment of the method the LRR domain of the alpha-WOLF 8 allele is determined by using a primer pair to amplify the genomic DNA region of the LRR domain. The forward primer is preferably a nucleic acid molecule having the sequence of SEQ ID NO:8 and the reverse primer is preferably a nucleic acid molecule having the sequence of SEQ ID NO:9.

Another aspect of the invention relates to a method for producing a spinach plant which may comprise resistance to *Peronospora farinosa* f. sp. *spinaciae* which may comprise: (a) crossing a plant which may comprise the alpha-WOLF 8 allele, with another plant; (b) optionally performing one or more rounds of selfing and/or crossing; (c) optionally selecting after each round of selfing or crossing for a plant that may comprise the alpha-WOLF 8 allele.

Selecting a plant which may comprise the alpha-WOLF 8 allele can be done genotypically by determining the presence of the genomic DNA sequence of the allele having in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:1.

In another embodiment, selecting a plant which may comprise the alpha-WOLF 8 allele can be done genotypically by determining the presence the coding sequence of the allele having in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:2, In another embodiment, selecting a plant which may comprise the alpha-WOLF 8 allele can be done genotypically by determining the presence the coding sequence of the allele having in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:3.

In yet another embodiment, selecting a plant which may comprise the alpha-WOLF 8 allele can be done genotypically by determining the presence the coding sequence of the allele having in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:4.

Alternatively, the presence of the alpha-WOLF 8 allele can be determined phenotypically by assaying a plant in a disease test, for example the test as described herein, and identifying a plant carrying the alpha-WOLF 8 allele based on the resistance pattern as described herein and indicated in Table 1.

The invention further relates to the use of a spinach plant carrying the alpha-WOLF 8 allele in breeding to confer resistance against *Peronospora farinosa* f. sp. *spinaciae*.

The invention also relates to a breeding method for the development of spinach plants carrying the alpha-WOLF 8 allele of the invention wherein germplasm which may comprise said allele is used. Seed capable of growing into a plant which may comprise the allele of the invention and being representative for the germplasm was deposited with the NCIMB under deposit number NCIMB 42646.

In another aspect, the invention relates to a method for the production of a spinach plant which may comprise the alpha-WOLF 8 allele, which method may comprise: (a) crossing a plant which may comprise the allele with another plant; (b) optionally selecting for plants which may comprise said allele in the F1; (c) optionally backcrossing the resulting F1 with the preferred parent and selecting for plants that have the said allele in the BC1F1; (d) optionally performing one or more additional rounds of selfing, crossing, and/or backcrossing, and subsequently selecting for a plant which may comprise the said allele or shows the resistance profile corresponding to said allele. The invention also encompasses a spinach plant produced by this method.

The invention also relates to a harvested leaf of a spinach plant of the invention, to a food product which may comprise a harvested leaf of a spinach plant of the invention, either in natural or in processed form.

Spinach leaves are sold in packaged form, including without limitation as pre-packaged spinach leaves or as processed in a salad which may comprise said leaves.

Mention of such a package is e.g. made in U.S. Pat. No. 5,523,136, which provides packaging film, and packages from such packaging film, including such packaging containing leafy produce, and methods for making and using such packaging film and packages, which are suitable for use with the spinach leaves of the invention. Thus, the invention comprehends the use of and methods for making and using the leaves of the spinach plant of the invention, as well as leaves of spinach plants derived from the invention.

The invention further relates to a container which may comprise one or more plants of the invention, or one or more spinach plants derived from a plant of the invention, in a growth substrate for harvest of leaves from the plant, in a domestic environment. This way the consumer may pick very fresh leaves for use in salads, when the plant is in a ready-to-harvest condition.

The invention also relates to the use of a spinach plant, of which representative seed was deposited with the NCIMB under accession number NCIMB 42646, in the production of a spinach plant which may comprise the alpha-WOLF 8 allele.

In a further embodiment the said spinach plant is a hybrid, doubled haploid, or inbred spinach plant.

Another aspect of the invention is the use of a cell which may comprise the alpha-WOLF 8 allele for the production of a spinach plant showing resistance to *Peronospora farinosa* f. sp. *spinaciae*.

The invention also relates to the use of a tissue culture which may comprise the alpha-WOLF 8 allele for the production of a spinach plant showing resistance to *Peronospora farinosa* f. sp. *spinaciae*.

Resistance Information

TABLE 1

Resistance profile conferred by the Alpha-WOLF 8 allele. A "−" means complete resistance against a particular downy mildew race; "(−)" means intermediate resistance against a particular downy mildew race; "+" means that the allele confers no resistance and would cause a plant only carrying the Alpha-WOLF 8 allele to be fully susceptible for that particular downy mildew race. Alpha-WOLF 8 resistance profile

| *Peronospora farinosa* f. sp. *Spinaciae* race | Resistance score |
| --- | --- |
| Pfs: 1 | − |
| Pfs: 2 | − |
| Pfs: 3 | + |
| Pfs: 4 | + |
| Pfs: 5 | (−)* |
| Pfs: 6 | − |
| Pfs: 7 | + |
| Pfs: 8 | − |
| Pfs: 9 | + |
| Pfs: 10 | (−)* |
| Pfs: 11 | + |
| Pfs: 12 | + |
| Pfs: 13 | + |
| Pfs: 14 | + |
| Pfs: 15 | − |
| Pfs: 16 | (−)* |

*The intermediate resistances against Pfs: 5, Pfs: 10 and Pfs: 16 conferred by the alpha-WOLF 8 allele are only observed in homozygous state. A plant carrying the allele in heterozygous state and not carrying any other resistance conferring allele (i.e. carrying the beta-WOLF zero allele) would be susceptibile for Pfs: 5, Pfs: 10, and Pfs: 16.

Sequence Information

TABLE 2

| Sequence information. | |
| --- | --- |
| SEQ ID No: 1:<br>Genomic<br>sequence of<br>alpha-WOLF8 | ATGGCCGAAATCGGATACTCGGTTTGTGCGAAACTCATCGA<br>AGTGATTGGCAGTGAGCTGATCAAAGAGATTTGTGACACAT<br>GGGGTTACAAATCTCTTCTTGAGGACCTCAACAAAACTGTAT<br>TGACGGTCAGGAACGTTCTCATTCAAGCCGGGGTGATGCGG<br>GAGCTTACTAGTGAACAACAAGGTTTCATTGCAGACCTTAA<br>AGATGTTGTTTATGATGCTGATGACTTGTTCGACAAGTTACT<br>CACTCGTGCTGAGCGAAAACAGATTGATGGAAACGAAATCT<br>CTGAAAAGGTACGTCGTTTCTTTTCCTCTAGTAACAAGATCG<br>GTCAAGCTTACTACATGTCTCGTAAGGTTAAGGAAATTAAG<br>AAGCAGTTGGATGAAATTGTTGATAGGCATACAAAATTTGG<br>GTTTAGTGCCGAGTTTATACCTGTTTGTAGGGAAAGGGGGA<br>ACGAGAGGGAAACACGTTCATATATAGATGTCAAGAATATT<br>CTTGGGAGGGATAAAGATAAGAATGATATCATAGATAGGTT<br>GCTTAATCGTAATGGTAATGAAGCTTGTAGTTTCCTGACCAT<br>AGTGGGAGCGGGAGGATTGGGAAAAACTGCTCTTGCACAAC<br>TTGTGTTCAATGATGAAAGGGTCAAAATTGAGTTCCATGATT<br>TGAGGTATTGGGTTTGTGTCTCTGATCAAGATGGGGGCCAAT<br>TTGATGTGAAAGAAATCCTTTGTAAGATTTTAGAGGTGGTTA<br>CTAAGGAGAAAGTTGATAATAGTTCCACATTGGAATTGGTA<br>CAAAGCCAATTTCAAGAGAAGTTAAGAGGAAAGAAGTACTT<br>CCTTGTTCTTGATGATGTATGGAACGAAGATCGTGAGAAGTG<br>GCTTCCTTTGGAAGAGTTGTTAATGTTGGGTCAAGGGGGAA<br>GCAAGGTTGTAGTGACCGCACGTTCAGAGAAGACAGCAAAT<br>GTCATAGGGAAAAGACATTTTTATACACTGGAATGTTTGTCA<br>CCAGATTATTCATGGAGCTTATTTGAAATGTCGGCTTTTCAG<br>AAAGGGCATGAGCAGGAAAACCATCACGAACTAGTTGATAT<br>TGGGAAAAAGATTGTTGAAAAATGTTATAACAATCCACTTG<br>CTATAACGGTGGTAGGAAGTCTTCTTTATGGAGAGGAGATA<br>AGTAAGTGGCGGTCATTTGAAATGAGTGAGTTGGCCAAAAT<br>TGGCAATGGGGATAATAAGATTTTGCCGATATTAAAGCTCA<br>GTTACCATAATCTTATACCCTCGTTGAAGAGTTGCTTCAGTT<br>ATTGTGCAGTGTTTCCCAAGGATCATGAAATAAAGAAGGAG<br>ATGTTGATTGATCTTTGGATAGCACAAGGATACGTTGTGGCA<br>CTTGATGGAGGTCAAAGTATAGAAGATGCTGCCGAAGAACA<br>TTTTGTAATTTTGTTACGGAGATGTTTCTTTCAAGATGTAAA<br>GAAGGATGAATATGGTGATGTTGATTCTGTTAAAATCCACG<br>ACTTGATGCACGATGTCGCCCAAGAAGTGGGGAGGGAGGAA<br>ATATGTGTAGTGAATGATAATACAAAGAACTTGGGTGATAA |

TABLE 2-continued

Sequence information.

```
AATCCGTCATGTACATGGTGATGTCAATAGATATGCACAAA
GAGTCTCTCTGTGTAGCCATAGCCATAAGATTCGTTCGTATA
TTGGTGGTGATTGTGAAAAACGTTGTGTGGATACACTAATAG
ACAAGTGGATGTGTCTTAGGATGTTGGACTTGTCATGGTCGG
ATGTTAAAAATTTGCCTAATTCAATAGGTAAATTGTTGCACT
TGAGGTATCTTAACCTGTCAGATAATAGAAATCTAAAGATA
CTTCCTGATGCAATTACAAGACTGCATAATTTGCAGACACTG
CTTTTAAAAGATTGCAGAAGTTTAAAGGAGTTGCCAAAAGA
TTTTTGCAAATTGGTCAAACTGAGACACTTGGATTTATGGGG
TTGTGATGATTTGATTGGTATGCCATTTGGAATGGATAAGCT
AACTAGTCTTAGAATACTACCAAACATTGTGGTGGGTAGGA
AGGAACAAAGTGTTGATGATGAGCTGAAAGCCCTTAAAGGC
CTCACCGAGATAAAAGGCGACATTGATATCAAATCTGTGA
AAATTATAGAATAGTTGAAGGCATGAATGACACAGGAGGAG
CTGGGTATTTGAAGAGCATGAAACATCTCAGGGAGATTGGT
ATTACATTTGATGGTGGATGTGTTAACCCTGAAGCTGTGTTG
GCAACCCTAGAGCCACCTTCAAATATCAAGAGCTTATCTATA
CATCGTTTTGATGGTAAAACACTTCCAGTATGGGGAAGAGC
AGAGATTAATTGGGCAATCTCCCTCTCACATCTTGTCGACAT
CCAGCTTTGGCATTGTCGTAATTTGCAGGAGATGCCAGTGCT
GAGTAAACTGCCTCATTTGAAATCACTGGAACTTTATAATTT
GATTAGTTTAGAGTACATGGAGAGCACAAGCAGAAGCAGTA
GCAGTGACACAGAAGCAGCAACACCAGAATTACCAACATTC
TTCCCTTCCCTTGAAAAACTTACACTTTGGGGTCTGGAAAAG
TTGAAGGGTTTGGGGAACAGGAGATCGAGTAGTTTTCCCCG
CCTCTCTGAATTGAAAATCATGGAATGCCCAGATCTAACGTG
GTTTCCTCCCTGTCCAAGCCTTGAAAAACTTACACTTTGGCG
TCTGGACAAGTTGAAGGGTTTTGGGAACCGGAGATCGAGTA
CTTTTCCCCGCCTCTCTGAATTGGAAATCAAGAAATGCCCAG
ATCTAACGTCATTTCCTTCTTGTCCAAGCCTTGAGAAGTTGG
AATTGAAAGAAAGCAATGAAGCATTGCAAATAATAGTAAAA
ATAACAACAAGAGGTAAAGAAAAAGAAGAGAACAATAATG
CTGGTGTTAGAAATTCACAAGATGATGACAAAGTCAAATTA
CGGAAGATGGTGATAGACAATCTGGGTTATCTCAAATCACT
GCCCACAAATTGTCTTACTCACCTCGACCTTACAATAAGTGA
TTCCAAGGAGGGGGAGGGTGAATGGGAAGTTGGGGATGCAT
TTCAGAAGTGTGTATCTTCTTTGAGAAGCCTCACCATAATCG
GAAATCACGGAATAAATAAAGTGAAGAGACTGTCTGGAAGA
ACAGGGTTGGAGCATTTCACTCTGTTGGAATCACTCAAACTT
TCAGATATAGAAGACCAGGAAGATGAGGGCGAAGACAACA
TCATATTCTGGAAATCCTTTCCTCAAAACCTCCGCAGTTTGA
GAATTAAAGACTCTGACAAAATGACAAGTTTGCCCATGGGG
ATGCAGTACTTAACCTCCCTCCAAACCCTCTATCTACACCAT
TGTTATGAATTGAATTCCCTTCCAGAATGGATAAGCAGCTTA
TCATCTCTTCAATACCTGCGCATATACTACTGTCCAGCCCTG
AAATCACTACCAGAAGCAATGCGGAACCTCACCTCCCTTCA
GACACTTGGGATATCGGATTGTCCAGACCTAGTTAAAAGAT
GCAGAAAACCCAACGGCAAGGACTATCCCAAAATTCAACAC
ATCCCCTATTGGAGTATAGAACATCAGGTTATAACTAGCTTG
TAACTAACTTGTAACTACCTAGTATAAATACAGTAGTTTGTA
CTATTTTACATTCAATTACACAATTAATAAAATGTAGACTCT
CACTCTCTCTCTCTAAGCCACGAGCTCCAAGCTCGTCAATGG
CTTCCCTTCTCTGTTCTTGCTTTCTTCTTTCCTCTTCAATTCAC
AAATTCAACATGGTATCAGAGCGGGACGATCCTTGCTCTTCA
CTTCCGCACAAAATTTTCGTTCAATTCAACCCATCAAATTTTT
TTTTTCCCCCAAATTTTCTCGAATTCGGTCAAAATTCGACGA
ATTAGGGATTCAATTTACCCTGATTTCTTCTGATTCCATTCAA
TGATTGTTCATTTCGAATCTTGAATCAAATAATTGTTGATTCT
GGATTCCCCAAATTCTAGGGTTCTTGAAGGATTTACAAGAAT
CTGGCATTGCTGATAGATTCTTGAAGCAATTTGCGTCTCCGT
GTTCCTCGGTGGTCTTGAGTTTGTTTCCGTATTCGCTGCTCTC
ATCTTTACTGGGGATTGTGGTCTGATTTCTTGGCTTCCTCTGT
CGATGATGTGATTGGTAATACTTAAAACCCCTCTCTCTCTTT
CCGAAATTATTGATGCTGGTTCGTCATTTTTTTTTTGGAATC
ATCTCAGTTTATCGCCGCAATTTGAGTTGTTGTTGGGTAATT
GTTGTTGCTGCCGATGATGTTTTGTGAATTTGAGAATTGTTA
GAATGATTCTTGTTCAATCAATTTGGTTCTCATACTCTAATG
GAAGCCTGTTTTGGAGCGACGAATTATGCAATTCTGAGATTT
CTTTTGATCCTTATTTCTTTTCTTCACTTGAATTTCTGGTATTT
GTGAGTAATTCTTGGTTAATGTTTGATCTGGGTAGTTCTTGG
GTTTACTGAAGACGTTTCTTGAAGGTTTTGACAGAAAAGCTG
AGGTTTAATTCCAAAATTCTTCTGTCCAATTACATTTTATTG
TTGATGGTTCTTATGTGAGAACTAGACTGAGTTTTTTTTATG
AAATTGTTTCGACCTTCAGATGGATTCGAGAGATTTGAGTTC
ATTTTCTTTGATGAATGTGTTAGAAAAGGTTTTGGTGCAGTG
ACCATTTTAAACCAAATAGAGTTACATAAATATTGGGATTCT
TTTCTGGGAATGTAGTTAGGAGTTGAAATCTTTTGGAGCTGC
TTTACCATAAAACCCAGCCTCAGAGTCTGTTAACCAGTTAGG
```

TABLE 2-continued

Sequence information.

```
ACCGTGTAAACATGATCCCAGGCTGCATTTGCGTTATCAGAT
TTGATTCAGTTTTGGAATTGTGGATTTTGAGGGTTTAAAAGC
TTACAGTTGCTCCTGGAGAATGGTGTGAGCAATATAGGAATT
CAGCACTAGTATTGCAGAAAATGAAGCTTGGTTGTTGATTGT
TGGCATGTTTTGTTGCCATTGTTTTGGGTTGATGTTTTCCTTT
TCTTTTGAATGTTGGCACGATTCAACATTTCTTTCCTGCAACA
GATTTGGAGTTCAGTACCTGTATAATCAGGTCAATTTTGTTC
ATTTTTCCCAGCAACAGATCTGGAGAATCAGAACCTGTAAA
ANNNNNNNNNNNNNNNNNNNNNNNNNNNNNNNNNNNN
NNNNNNNNNNNNNNNNNNNNNNNACCCAAAGAGGTCAGTTT
TCATTGATCCATTGTGATCATTCTTTTGATGAGACCCATTGA
GGCTCATTTCTTCAAGGCAATATTGGAAGTTGTAGATTGATA
TGAGCAGTTGGTACAACAGCAACAAAAGTGGCCAGCATCTA
TGCTTGTTCATGAGGAGTTCTTGGTGCAGAGTTAATGAAGAG
TCTGTTTTGAAGCTTTCAAACTGAAGATGTTTATCACCATCT
CCAGTTTGAGGGGGGGTATTGGAGTATAGAACATCAGGTTA
TAACTAGCTTGTAACTAACTTGTAACTACCTAGTATAAATAC
AGTAGTTTGTACNNNNNNNNNNNNNNNNNNNNNNNNNNNN
NNNNNNNNNNNNNNNNNNNNNCCACGAGCTCCAAGCTCG
TCAATGGCTTCCCTTCTCTGTTCTTGCTTTCTTCTTTCCTCTTC
AATTCACAAATTCAACATCCCCAAAATTGTAAGTCATTGCAG
AAAGTAATTTATTCATTTATATTTATTTTATGCTTAGAATGAT
ATACGCAGTCGTCCTTTGGTTTCAAATCTTGAATTTGGTTTTT
GTTTTCTTTCTTTGTTTCTTTATTCAACACCAGCCCATTTATG
ATTGATTCATTAAAAAAAGGATGGAGTTTTATGGATTTGAAG
AAGACAACGAATTGAGATTCCTGGGGTTTTCTTTTTGTTGGG
GTTGGATTTCATGTATATGTTGCTGATTAAATACGAGACTGA
TGATGATGATGTGTTTATGGGTTTTAAATCAGATTAAATATA
TGGGAAATGCAAGTTAATTTGGGATGCACATAAGGTGTTTG
CTGAAATGTCTATGAGAAATGTTGTTTCTTGGACTTAGAATG
ATATACACTGTCGTCCTTTGGTTTCCAATCTTACATTTGGTTT
GTGTTTTCTTAGTTTGTTTCTTTAATCAACACCAACCCGTTTT
TTTTAAACTACCTGCAACTACTAATTTACGTTTACCCTGTATC
TCAGGTACTAAATGAATATTGGTGATTTTCAGTTACTCAACA
CTAGCTTGATCCTGAACGCACCCAACCTTCAGGTTAGAATCC
GGCTTACTCATCCTTTTGTCCAGTTTTCAAGTAATTGTTTTGG
CAGGATCAATTCTCTAATTGTTGTACACCGTATATTGCAATT
TATAGTGACTACAGTTAATGAATGTTTACAAAAAATTAGTCA
TGTAAAAACTTCTTCTCTGTCCATTACATAAACTCTTTTTCTC
TTTCTAACTTATCATGTTCATGTCTAAACAATTAAACATGCT
CACATCAATGTTCATTTAAGCTAACTTACTTCTGTAAGAGAG
CGAGCTAGTTAAAAACTCCTTTAACTTTCTGTTTTATACTCA
GGACATGGATTGATGCAAGCATGAAGAACTTCGGGAATTTG
CTAAAACTCTACCAAAGCGATGAGAGTTTGGACTTTATTTCA
CTTGAAGTCAGGGACTGTCAACAAAGCCACAGTGTGCATGT
TGGCTGTTTCACTTGGACGATAAAAAGGTTTATTTAATTGTT
TTCCTAAGTGTATTTGGCTTACAAGCTTTTACTTTTCACTTGA
AAGGGTTTTTCTTGTTTTAAGCTTTTCGAATTAGAGTTTTCGG
TTGAAGTAAGAGTAGTCGTATTAGTCTTTTACCTAAGGAAGA
CTCTTTTTTGTAATTTTCAGACTATGCAATTCAAGTTTTCGAG
TGTTTTCTTGCTTGTGTGATTGTGAGTTGGTGAATTCGTCTTT
CATACATTTTGAGATTATCAGAAGCTTTATGCTCCACCGGTA
GTCTAGTACCTTTTCTGTTACTGTGCAGGGAAGTAATCTGGT
ACCTTCTATATATATGGAAAAACATACATTATACATTATGCA
AAATTCTTACAGGTTAGTTACTTCCTGGAACTTCATTTACAC
TTAGTTTTTTTTGTTCCATTCCCTCGGAATCAAGTCATTCCCT
CTGAGAAATATGTAATGAACTTCTGTATGTTGCTGTTTGGTT
CCTGTTTTAATCTTCAATTTTCTTGTATAGTTACAGCTGCATT
TACAATGAAGTTTAAGCAGACACTCTCTTTATATAGTGCCTC
TTTCTGGAGCACCGTAGAGCTGTCTGTGGTTGATCACCATCT
GCTGCCGAGAGATTCAGCAATCGCGTGTTTGATCAGGTAAA
AGTTTTTATGTCAATGTGTTTTTTTTCCGTTTGATCAATTTA
TGTCTGTATTCAGATTCTTATCTTCTTACAGTAGCATAACAC
ATTGTTTCTTTCATTTATGTAAACTGTTTCAAGATTACAGAG
ATGTATGCTTCAGTCGACATTGATGATAACTTAAGATGGCAT
TCCTACAACAGTTGCAGGCGCATTCTAACTCCGGCAATTCTA
GTTAGGCAAGAGGAGCATTGCCAATACCTGCCACCTCTGGG
ATTTACTATACCAGGGTTGAAGTTTATGGAAGACACCAGCTA
TGCACAAGCCTTCAAGGGGTCATCCTACATAACAAGTTGAA
CCAACCAATTGCTTGTTGGTTCAGTGGTAATTGAAGCTGAAT
TTGGTAGGGATGGCCCGTGTTCGATCCCCACAACAACAATTG
GGAGGGGACTGGAACCTATCCACACAGAACTCGCCCTGAAT
CCGGATTAGCCCTAAGGGTGAACGGGGTGCTAACACCAAAA
AAAAAAACATAACAAGTTGAACCAAACATACTTTGTTTGAA
TTGAAGATTTAGTGATTTCATTTGATCGATTGAGATGTCTTA
TTATAAGCGTATATGCTCTTGGATTTGGCCACTTAGGTGTTG
TTTGACAATTGGACATTAACTCGCTTTTATATTTTCTTTTCTC
TTAGGAAAGGTGATCCTGAGAATTTATATTGGAACACTTTTT
```

TABLE 2-continued

Sequence information.

|  |  |
|---|---|
|  | TTTTCTCACTAGCTTTAAAAAAGTGTTCTGTGTTACCTGCAAT<br>TCAATTTGATTATTTTTCACATAGTTTTACCTGAAAAAGTGTT<br>ACCTGAAAAAGTGTTACCTGAAAATCAACTGACATAAGTTTT<br>TGTTTGGATCCAATTAAGGACACTAGATAAATCGGAATAAA<br>TAATCAACCAATTAAGTACTTCATAATTAAATATGAAGTGTA<br>TTATTATCTTATGCTTGTGACATTGAAGGATGTTATGATATTT<br>TAACTCAATACCTTGCAAAATATACTGG |
| SEQ ID No: 2:<br>cds alpha-<br>WOLF8 | ATGGCCGAAATCGGATACTCGGTTTGTGCGAAACTCATCGA<br>AGTGATTGGCAGTGAGCTGATCAAAGAGATTTGTGACACAT<br>GGGGTTACAAATCTCTTCTTGAGGACCTCAACAAAACTGTAT<br>TGACGGTCAGGAACGTTCTCATTCAAGCCGGGGTGATGCGG<br>GAGCTTACTAGTGAACAACAAGGTTTCATTGCAGACCTTAA<br>AGATGTTGTTTATGATGCTGATGACTTGTTCGACAAGTTACT<br>CACTCGTGCTGAGCGAAAACAGATTGATGGAAACGAAATCT<br>CTGAAAAGGTACGTCGTTTCTTTTCCTCTAGTAACAAGATCG<br>GTCAAGCTTACTACATGTCTCGTAAGGTTAAGGAAATTAAG<br>AAGCAGTTGGATGAAATTGTTGATAGGCATACAAAATTTGG<br>GTTTAGTGCCGAGTTTATACCTGTTTGTAGGGAAAGGGGGA<br>ACGAGAGGGAAACACGTTCATATATAGATGTCAAGAATATT<br>CTTGGGAGGGATAAAGATAAGAATGATATCATAGATAGGTT<br>GCTTAATCGTAATGGTAATGAAGCTTGTAGTTTCCTGACCAT<br>AGTGGGAGCGGGAGGATTGGGAAAAACTGCTCTTGCACAAC<br>TTGTGTTCAATGATGAAAGGGTCAAAATTGAGTTCCATGATT<br>TGAGGTATTGGGTTTGTGTCTCTGATCAAGATGGGGCCAAT<br>TTGATGTGAAAGAAATCCTTTGTAAGATTTTAGAGGTGGTTA<br>CTAAGGAGAAAGTTGATAATAGTTCCACATTGGAATTGGTA<br>CAAAGCCAATTTCAAGAGAAGTTAAGAGGAAAGAAGTACTT<br>CCTTGTTCTTGATGATGTATGGAACGAAGATCGTGAGAAGTG<br>GCTTCCTTTGGAAGAGTTGTTAATGTTGGGTCAAGGGGGAA<br>GCAAGGTTGTAGTGACCGCACGTTCAGAGAAGACAGCAAAT<br>GTCATAGGGAAAAGACATTTTTATACACTGGAATGTTTGTCA<br>CCAGATTATTCATGGAGCTTATTTGAAATGTCGGCTTTTCAG<br>AAAGGGCATGAGCAGGAAAACCATCACGAACTAGTTGATAT<br>TGGGAAAAAGATTGTTGAAAAATGTTATAACAATCCACTTG<br>CTATAACGGTGGTAGGAAGTCTTCTTTATGGAGAGGAGATA<br>AGTAAGTGGCGGTCATTTGAAATGAGTGAGTTGGCCAAAAT<br>TGGCAATGGGGATAATAAGATTTTGCCGATATTAAAGCTCA<br>GTTACCATAATCTTATACCCTCGTTGAAGAGTTGCTTCAGTT<br>ATTGTGCAGTGTTTCCCAAGGATCATGAAATAAAGAAGGAG<br>ATGTTGATTGATCTTTGGATAGCACAAGGATACGTTGTGGCA<br>CTTGATGGAGGTCAAAGTATAGAAGATGCTGCCGAAGAACA<br>TTTTGTAATTTTGTTACGGAGATGTTTCTTTCAAGATGTAAA<br>GAAGGATGAATATGGTGATGTTGATTCTGTTAAAATCCACG<br>ACTTGATGCACGATGTCGCCCAAGAAGTGGGGAGGGAGGAA<br>ATATGTGTAGTGAATGATAATACAAAGAACTTGGGTGATAA<br>AATCCGTCATGTACATGGTGATGTCAATAGATATGCACAAA<br>GAGTCTCTCTGTGTAGCCATAGCCATAAGATTCGTTCGTATA<br>TTGGTGGTGATTGTGAAAAACGTTGTGTGGATACACTAATAG<br>ACAAGTGGATGTGTCTTAGGATGTTGGACTTGTCATGGTCGG<br>ATGTTAAAAATTTGCCTAATTCAATAGGTAAATTGTTGCACT<br>TGAGGTATCTTAACCTGTCAGATAATAGAAATCTAAAGATA<br>CTTCCTGATGCAATTACAAGACTGCATAATTTTGCAGACACTG<br>CTTTTAAAAGATTGCAGAAGTTTAAAGGAGTTGCCAAAAGA<br>TTTTTGCAAATTGGTCAAACTGAGACACTTGGATTTATGGGG<br>TTGTGATGATTTGATTGGTATGCCATTTGGAATGGATAAGCT<br>AACTAGTCTTAGAATACTACCAAACATTGTGGTGGGTAGGA<br>AGGAACAAAGTGTTGATGATGAGCTGAAAGCCCTTAAAGGC<br>CTCACCGAGATAAAAGGCGACATTGATATCAAAATCTGTGA<br>AAATTATAGAATAGTTGAAGGCATGAATGACACAGGAGGAG<br>CTGGGTATTTGAAGAGCATGAAACATCTCAGGGAGATTGGT<br>ATTACATTTGATGGTGGATGTGTTAACCCTGAAGCTGTGTTG<br>GCAACCCTAGAGCCACCTTCAAATATCAAGAGCTTATCTATA<br>CATCGTTTTGATGGTAAAACACTTCCAGTATGGGGAAGAGC<br>AGAGATTAATTGGGCAATCTCCCTCTCACATCTTGTCGACAT<br>CCAGCTTTGGCATTGTCGTAATTTGCAGGAGATGCCAGTGCT<br>GAGTAAACTGCCTCATTTGAAATCACTGGAACTTTATAATTT<br>GATTAGTTTAGAGTACATGGAGAGCACAAGCAGAAGCAGTA<br>GCAGTGACACAGAAGCAGCAACACCAGAATTACCAACATTC<br>TTCCCTTCCCTTGAAAAACTTACACTTTGGGGTCTGGAAAAG<br>TTGAAGGGTTTGGGGAACAGGAGATCGAGTAGTTTTCCCCG<br>CCTCTCTGAATTGAAAATCATGGAATGCCCAGATCTAACGTG<br>GTTTCCTCCCTGTCCAAGCCTTGAAAAACTTACACTTTGGCG<br>TCTGGACAAGTTGAAGGGTTTTGGGAACCGGAGATCGAGTA<br>CTTTTCCCCGCCTCTCTGAATTGGAAATCAAGAAATGCCCAG<br>ATCTAACGTCATTTCCTTCTTGTCCAAGCCTTGAGAAGTTGG<br>AATTGAAAGAAAGCAATGAAGCATTGCAAATAATAGTAAAA<br>ATAACAACAAGAGGTAAAGAAAAAGAAGAGAACAATAATG |

TABLE 2-continued

Sequence information.

|  |  |
|---|---|
|  | CTGGTGTTAGAAATTCACAAGATGATGACAAAGTCAAATTA<br>CGGAAGATGGTGATAGACAATCTGGGTTATCTCAAATCACT<br>GCCCACAAATTGTCTTACTCACCTCGACCTTACAATAAGTGA<br>TTCCAAGGAGGGGGAGGGTGAATGGGAAGTTGGGGATGCAT<br>TTCAGAAGTGTGTATCTTCTTTGAGAAGCCTCACCATAATCG<br>GAAATCACGGAATAAATAAAGTGAAGAGACTGTCTGGAAGA<br>ACAGGGTTGGAGCATTTCACTCTGTTGGAATCACTCAAACTT<br>TCAGATATAGAAGACCAGGAAGATGAGGGCGAAGACAACA<br>TCATATTCTGGAAATCCTTTCCTCAAAACCTCCGCAGTTTGA<br>GAATTAAAGACTCTGACAAATGACAAGTTTGCCCATGGGG<br>ATGCAGTACTTAACCTCCCTCCAAACCCTCTATCTACACCAT<br>TGTTATGAATTGAATTCCCTTCCAGAATGGATAAGCAGCTTA<br>TCATCTCTTCAATACCTGCGCATATACTACTGTCCAGCCCTG<br>AAATCACTACCAGAAGCAATGCGGAACCTCACCTCCCTTCA<br>GACACTTGGGATATCGGATTGTCCAGACCTAGTTAAAAGAT<br>GCAGAAAACCCAACGGCAAGGACTATCCCAAAATTCAACAC<br>ATCCCCTATTGGAGTATAGAACATCAGGTTATAACTAGCTTG<br>TAA |
| SEQ ID No: 3:<br>cds of alpha-<br>WOLF 8<br>(isoform 1) | ATGGCCGAAATCGGATACTCGGTTTGTGCGAAACTCATCGA<br>AGTGATTGGCAGTGAGCTGATCAAAGAGATTTGTGACACAT<br>GGGGTTACAAATCTCTTCTTGAGGACCTCAACAAAACTGTAT<br>TGACGGTCAGGAACGTTCTCATTCAAGCCGGGGTGATGCGG<br>GAGCTTACTAGTGAACAACAAGGTTTCATTGCAGACCTTAA<br>AGATGTTGTTTATGATGCTGATGACTTGTTCGACAAGTTACT<br>CACTCGTGCTGAGCGAAAACAGATTGATGGAAACGAAATCT<br>CTGAAAAGGTACGTCGTTTCTTTTCCTCTAGTAACAAGATCG<br>GTCAAGCTTACTACATGTCTCGTAAGGTTAAGGAAATTAAG<br>AAGCAGTTGGATGAAATTGTTGATAGGCATACAAAATTTGG<br>GTTTAGTGCCGAGTTTATACCTGTTTGTAGGGAAAGGGGGA<br>ACGAGAGGGAAACACGTTCATATATAGATGTCAAGAATATT<br>CTTGGGAGGGATAAAGATAAGAATGATATCATAGATAGGTT<br>GCTTAATCGTAATGGTAATGAAGCTTGTAGTTTCCTGACCAT<br>AGTGGGAGCGGGAGGATTGGGAAAAACTGCTCTTGCACAAC<br>TTGTGTTCAATGATGAAAGGGTCAAAATTGAGTTCCATGATT<br>TGAGGTATTGGGTTTGTGTCTCTGATCAAGATGGGGCCAAT<br>TTGATGTGAAAGAAATCCTTTGTAAGATTTTAGAGGTGGTTA<br>CTAAGGAGAAAGTTGATAATAGTTCCACATTGGAATTGGTA<br>CAAAGCCAATTTCAAGAGAAGTTAAGAGGAAAGAAGTACTT<br>CCTTGTTCTTGATGATGTATGGAACGAAGATCGTGAGAAGTG<br>GCTTCCTTTGGAAGAGTTGTTAATGTTGGGTCAAGGGGGAA<br>GCAAGGTTGTAGTGACCGCACGTTCAGAGAAGACAGCAAAT<br>GTCATAGGGAAAGACATTTTTATACACTGGAATGTTTGTCA<br>CCAGATTATTCATGGAGCTTATTTGAAATGTCGGCTTTTCAG<br>AAAGGGCATGAGCAGGAAAACCATCACGAACTAGTTGATAT<br>TGGGAAAAAGATTGTTGAAAAATGTTATAACAATCCACTTG<br>CTATAACGGTGGTAGGAAGTCTTCTTTATGGAGAGGAGATA<br>AGTAAGTGGCGGTCATTTGAAATGAGTGAGTTGGCCAAAAT<br>TGGCAATGGGGATAATAAGATTTTGCCGATATTAAAGCTCA<br>GTTACCATAATCTTATACCCTCGTTGAAGAGTTGCTTCAGTT<br>ATTGTGCAGTGTTTCCCAAGGATCATGAAATAAAGAAGGAG<br>ATGTTGATTGATCTTTGGATAGCACAAGGATACGTTGTGGCA<br>CTTGATGGAGGTCAAAGTATAGAAGATGCTGCCGAAGAACA<br>TTTTGTAATTTTGTTACGGAGATGTTTCTTTCAAGATGTAAA<br>GAAGGATGAATATGGTGATGTTGATTCTGTTAAAATCCACG<br>ACTTGATGCACGATGTCGCCCAAGAAGTGGGGAGGGAGGAA<br>ATATGTGTAGTGAATGATAATACAAAGAACTTGGGTGATAA<br>AATCCGTCATGTACATGGTGATGTCAATAGATATGCACAAA<br>GAGTCTCTCTGTGTAGCCATAGCCATAAGATTCGTTCGTATA<br>TTGGTGGTGATTGTGAAAAACGTTGTGTGGATACACTAATAG<br>ACAAGTGGATGTGTCTTAGGATGTTGGACTTGTCATGGTCGG<br>ATGTTAAAAATTTGCCTAATTCAATAGGTAAATTGTTGCACT<br>TGAGGTATCTTAACCTGTCAGATAATAGAAATCTAAAGATA<br>CTTCCTGATGCAATTACAAGACTGCATAATTTGCAGACACTG<br>CTTTTAAAAGATTGCAGAAGTTTAAAGGAGTTGCCAAAAGA<br>TTTTTGCAAATTGGTCAAACTGAGACACTTGGATTTATGGGG<br>TTGTGATGATTTGATTGGTATGCATTTGGAATGGATAAGCT<br>AACTAGTCTTAGAATACTACCAAACATTGTGGTGGGTAGGA<br>AGGAACAAAGTGTTGATGATGAGCTGAAAGCCCTTAAAGGC<br>CTCACCGAGATAAAAGGCGACATTGATATCAAAATCTGTGA<br>AAATTATAGAATAGTTGAAGGCATGAATGACACAGGAGGAG<br>CTGGGTATTTGAAGAGCATGAAACATCTCAGGGAGATTGGT<br>ATTACATTTGATGGTGGATGTGTTAACCCTGAAGCTGTGTTG<br>GCAACCCTAGAGCCACCTTCAAATATCAAGAGCTTATCTATA<br>CATCGTTTTGATGGTAAAACACTTCCAGTATGGGGAAGAGC<br>AGAGATTAATTGGGCAATCTCCCTCTCACATCTTGTCGACAT<br>CCAGCTTTGGCATTGTCGTAATTTGCAGGAGATGCCAGTGCT<br>GAGTAAACTGCCTCATTTGAAATCACTGGAACTTTATAATTT |

TABLE 2-continued

Sequence information.

|  |  |
| --- | --- |
|  | GATTAGTTTAGAGTACATGGAGAGCACAAGCAGAAGCAGTA<br>GCAGTGACACAGAAGCAGCAACACCAGAATTACCAACATTC<br>TTCCCTTCCCTTGAAAAACTTACACTTTGGGGTCTGGAAAAG<br>TTGAAGGGTTTGGGGAACAGGAGATCGAGTAGTTTTCCCCG<br>CCTCTCTGAATTGAAAATCATGGAATGCCCAGATCTAACGTG<br>GTTTCCTCCCTGTCCAAGCCTTGAAAAACTTACACTTTGGCG<br>TCTGGACAAGTTGAAGGGTTTTGGGAACCGGAGATCGAGTA<br>CTTTTCCCCGCCTCTCTGAATTGGAAATCAAGAAATGCCCAG<br>ATCTAACGTCATTTCCTTCTTGTCCAAGCCTTGAGAAGTTGG<br>AATTGAAAGAAAGCAATGAAGCATTGCAAATAATAGTAAAA<br>ATAACAACAAGAGGTAAAGAAAAAGAAGAGAACAATAATG<br>CTGGTGTTAGAAATTCACAAGATGATGACAAAGTCAAATTA<br>CGGAAGATGGTGATAGACAATCTGGGTTATCTCAAATCACT<br>GCCCACAAATTGTCTTACTCACCTCGACCTTACAATAAGTGA<br>TTCCAAGGAGGGGGAGGGTGAATGGGAAGTTGGGGATGCAT<br>TTCAGAAGTGTGTATCTTCTTTGAGAAGCCTCACCATAATCG<br>GAAATCACGGAATAAATAAAGTGAAGAGACTGTCTGGAAGA<br>ACAGGGTTGGAGCATTTCACTCTGTTGGAATCACTCAAACTT<br>TCAGATATAGAAGACCAGGAAGATGAGGGCGAAGACAACA<br>TCATATTCTGGAAATCCTTTCCTCAAAACCTCCGCAGTTTGA<br>GAATTAAAGACTCTGACAAAATGACAAGTTTGCCCATGGGG<br>ATGCAGTACTTAACCTCCCTCCAAACCCTCTATCTACACCAT<br>TGTTATGAATTGAATTCCCTTCCAGAATGGATAAGCAGCTTA<br>TCATCTCTTCAATACCTGCGCATATACTACTGTCCAGCCCTG<br>AAATCACTACCAGAAGCAATGCGGAACCTCACCTCCCTTCA<br>GACACTTGGGATATCGGATTGTCCAGACCTAGTTAAAAGAT<br>GCAGAAAACCCAACGGCAAGGACTATCCCAAAATTCAACAC<br>ATCCCCTATTGGAGTATAGAACATCAGGTACTAAATGAATAT<br>TGGTGA |
| SEQ ID No: 4:<br>cds of alpha-<br>WOLF 8<br>(isoform 2) | ATGGCCGAAATCGGATACTCGGTTTGTGCGAAACTCATCGA<br>AGTGATTGGCAGTGAGCTGATCAAAGAGATTTGTGACACAT<br>GGGGTTACAAATCTCTTCTTGAGGACCTCAACAAAACTGTAT<br>TGACGGTCAGGAACGTTCTCATTCAAGCCGGGGTGATGCGG<br>GAGCTTACTAGTGAACAACAAGGTTTCATTGCAGACCTTAA<br>AGATGTTGTTTATGATGCTGATGACTTGTTCGACAAGTTACT<br>CACTCGTGCTGAGCGAAAACAGATTGATGGAAACGAAATCT<br>CTGAAAAGGTACGTCGTTTCTTTTCCTCTAGTAACAAGATCG<br>GTCAAGCTTACTACATGTCTCGTAAGGTTAAGGAAATTAAG<br>AAGCAGTTGGATGAAATTGTTGATAGGCATACAAAATTTGG<br>GTTTAGTGCCGAGTTTATACCTGTTTGTAGGGAAAGGGGGA<br>ACGAGAGGGAAACACGTTCATATATAGATGTCAAGAATATT<br>CTTGGGAGGGATAAAGATAAGAATGATATCATAGATAGGTT<br>GCTTAATCGTAATGGTAATGAAGCTTGTAGTTTCCTGACCAT<br>AGTGGGAGCGGGAGGATTGGGAAAAACTGCTCTTGCACAAC<br>TTGTGTTCAATGATGAAAGGGTCAAAATTGAGTTCCATGATT<br>TGAGGTATTGGGTTTGTGTCTCTGATCAAGATGGGGCCAAT<br>TTGATGTGAAAGAAATCCTTTGTAAGATTTTAGAGGTGGTTA<br>CTAAGGAGAAAGTTGATAATAGTTCCACATTGGAATTGGTA<br>CAAAGCCAATTTCAAGAGAAGTTAAGAGGAAAGAAGTACTT<br>CCTTGTTCTTGATGATGTATGGAACGAAGATCGTGAGAAGTG<br>GCTTCCTTTGGAAGAGTTGTTAATGTTGGGTCAAGGGGGAA<br>GCAAGGTTGTAGTGACCGCACGTTCAGAGAAGACAGCAAAT<br>GTCATAGGGAAAAGACATTTTTATACACTGGAATGTTTGTCA<br>CCAGATTATTCATGGAGCTTATTTGAAATGTCGGCTTTTCAG<br>AAAGGGCATGAGCAGGAAAACCATCACGAACTAGTTGATAT<br>TGGGAAAAAGATTGTTGAAAAATGTTATAACAATCCACTTG<br>CTATAACGGTGGTAGGAAGTCTTCTTTATGGAGAGGAGATA<br>AGTAAGTGGCGGTCATTTGAAATGAGTGAGTTGGCCAAAAT<br>TGGCAATGGGGATAATAAGATTTTGCCGATATTAAAGCTCA<br>GTTACCATAATCTTATACCCTCGTTGAAGAGTTGCTTCAGTT<br>ATTGTGCAGTGTTTCCCAAGGATCATGAAATAAAGAAGGAG<br>ATGTTGATTGATCTTTGGATAGCACAAGGATACGTTGTGGCA<br>CTTGATGGAGGTCAAAGTATAGAAGATGCTGCCGAAGAACA<br>TTTTGTAATTTTGTTACGGAGATGTTTCTTTCAAGATGTAAA<br>GAAGGATGAATATGGTGATGTTGATTCTGTTAAAATCCACG<br>ACTTGATGCACGATGTCGCCCAAGAAGTGGGGAGGGAGGAA<br>ATATGTGTAGTGAATGATAATACAAAGAACTTGGGTGATAA<br>AATCCGTCATGTACATGGTGATGTCAATAGATATGCACAAA<br>GAGTCTCTCTGTGTAGCCATAGCCATAAGATTCGTTCGTATA<br>TTGGTGGTGATTGTGAAAAACGTTGTGTGGATACACTAATAG<br>ACAAGTGGATGTGCTTAGGATGTTGGACTTGTCATGGTCGG<br>ATGTTAAAAATTTGCCTAATTCAATAGGTAAATTGTTGCACT<br>TGAGGTATCTTAACCTGTCAGATAATAGAAATCTAAAGATA<br>CTTCCTGATGCAATTACAAGACTGCATAATTTGCAGACACTG<br>CTTTTAAAAGATTGCAGAAGTTTAAAGGAGTTGCCAAAAGA<br>TTTTTGCAAATTGGTCAAACTGAGACACTTGGATTTATGGGG<br>TTGTGATGATTTGATTGGTATGCCATTTGGAATGGATAAGCT |

TABLE 2-continued

Sequence information.

```
AACTAGTCTTAGAATACTACCAAACATTGTGGTGGGTAGGA
AGGAACAAAGTGTTGATGATGAGCTGAAAGCCCTTAAAGGC
CTCACCGAGATAAAAGGCGACATTGATATCAAAATCTGTGA
AAATTATAGAATAGTTGAAGGCATGAATACACAGGAGGAG
CTGGGTATTTGAAGAGCATGAAACATCTCAGGGAGATTGGT
ATTACATTTGATGGTGGATGTGTTAACCCTGAAGCTGTGTTG
GCAACCCTAGAGCCACCTTCAAATATCAAGAGCTTATCTATA
CATCGTTTTGATGGTAAAACACTTCCAGTATGGGGAAGAGC
AGAGATTAATTGGGCAATCTCCCTCTCACATCTTGTCGACAT
CCAGCTTTGGCATTGTCGTAATTTGCAGGAGATGCCAGTGCT
GAGTAAACTGCCTCATTTGAAATCACTGGAACTTTATAATTT
GATTAGTTTAGAGTACATGGAGAGCACAAGCAGAAGCAGTA
GCAGTGACACAGAAGCAGCAACACCAGAATTACCAACATTC
TTCCCTTCCCTTGAAAAACTTACACTTTGGGGTCTGGAAAAG
TTGAAGGGTTTGGGGAACAGGAGATCGAGTAGTTTTCCCCG
CCTCTCTGAATTGAAAATCATGGAATGCCCAGATCTAACGTG
GTTTCCTCCCTGTCCAAGCCTTGAAAAACTTACACTTTGGCG
TCTGGACAAGTTGAAGGGTTTTGGGAACCGGAGATCGAGTA
CTTTTCCCCGCCTCTCTGAATTGGAAATCAAGAAATGCCCAG
ATCTAACGTCATTTCCTTCTTGTCCAAGCCTTGAGAAGTTGG
AATTGAAAGAAAGCAATGAAGCATTGCAAATAATAGTAAAA
ATAACAACAAGAGGTAAAGAAAAAGAAGAGAACAATAATG
CTGGTGTTAGAAATTCACAAGATGATGACAAAGTCAAATTA
CGGAAGATGGTGATAGACAATCTGGGTTATCTCAAATCACT
GCCCACAAATTGTCTTACTCACCTCGACCTTACAATAAGTGA
TTCCAAGGAGGGGAGGGTGAATGGGAAGTTGGGGATGCAT
TTCAGAAGTGTGTATCTTCTTTGAGAAGCCTCACCATAATCG
GAAATCACGGAATAAATAAAGTGAAGAGACTGTCTGGAAGA
ACAGGGTTGGAGCATTTCACTCTGTTGGAATCACTCAAACTT
TCAGATATAGAAGACCAGGAAGATGAGGGCGAAGACAACA
TCATATTCTGGAAATCCTTTCCTCAAAACCTCCGCAGTTTGA
GAATTAAAGACTCTGACAAAATGACAAGTTTGCCCATGGGG
ATGCAGTACTTAACCTCCCTCCAAACCCTCTATCTACACCAT
TGTTATGAATTGAATTCCCTTCCAGAATGGATAAGCAGCTTA
TCATCTCTTCAATACCTGCGCATATACTACTGTCCAGCCCTG
AAATCACTACCAGAAGCAATGCGGAACCTCACCTCCCTTCA
GACACTTGGGATATCGGATTGTCCAGACCTAGTTAAAAGAT
GCAGAAAACCCAACGGCAAGGACTATCCCAAAATTCAACAC
ATCCCCTATTGGAGTATAGAACATCAGTTACTCAACACTAGC
TTGATCCTGAACGCACCCAACCTTCAGGACATGGATTGA
```

SEQ ID No: 5:
protein
sequence of
alpha-WOLF 8

MAEIGYSVCAKLIEVIGSELIKEICDTWGYKSLLEDLNKTVLTV
RNVLIQAGVMRELTSEQQGFIADLKDVVYDADDLFDKLLTRAE
RKQIDGNEISEKVRRFFSSSNKIGQAYYMSRKVKEIKKQLDEIV
DRHTKFGFSAEFIPVCRERGNERETRSYIDVKNILGRDKDKNDII
DRLLNRNGNEACSFLTIVGAGGLGKTALAQLVFNDERVKIEFH
DLRYWVCVSDQDGGQFDVKEILCKILEVVTKEKVDNSSTLELV
QSQFQEKLRGKKYFLVLDDVWNEDREKWLPLEELLMLGQGGS
KVVVTARSEKTANVIGKRHFYTLECLSPDYSWSLFEMSAFQKG
HEQENHHELVDIGKKIVEKCYNNPLAITVVGSLLYGEEISKWRS
FEMSELAKIGNGDNKILPILKLSYHNLIPSLKSCFSYCAVFPKDH
EIKKEMLIDLWIAQGYVVALDGGQSIEDAAEEHFVILLRRCFFQ
DVKKDEYGDVDSVKIHDLMHDVAQEVGREEICVVNDNTKNL
GDKIRHVHGDVNRYAQRVSLCSHSHKIRSYIGGDCEKRCVDTL
IDKWMCLRMLDLSWSDVKNLPNSIGKLLHLRYLNLSDNRNLKI
LPDAITRLHNLQTLLLKDCRSLKELPKDFCKLVKLRHLDLWGC
DDLIGMPFGMDKLTSLRILPNIVVGRKEQSVDDELKALKGLTEI
KGDIDIKICENYRIVEGMNDTGGAGYLKSMKHLREIGITFDGGC
VNPEAVLATLEPPSNIKSLSIHRFDGKTLPVWGRAEINWAISLSH
LVDIQLWHCRNLQEMPVLSKLPHLKSLELYNLISLEYMESTSRS
SSSDTEAATPELPTFFPSLEKLTLWGLEKLKGLGNRRSSSFPRLS
ELKIMECPDLTWFPPCPSLEKLTLWRLDKLKGFGNRRSSTFPRL
SELEIKKCPDLTSFPPSCPSLEKLELKESNEALQIIVKITTRGKEKE
ENNNAGVRNSQDDDKVKLRKMVIDNLGYLKSLPTNCLTHLDL
TISDSKEGEGEWEVGDAFQKCVSSLRSLTIIGNHGINKVKRLSG
RTGLEHFTLLESLKLSDIEDQEDEGEDNIIFWKSFPQNLRSLRIK
DSDKMTSLPMGMQYLTSLQTLYLHHCYELNSLPEWISSLSSLQ
YLRIYYCPALKSLPEAMRNLTSLQTLGISDCPDLVKRCRKPNGK
DYPKIQHIPYWSIEHQVITSL

SEQ ID No: 6:
protein
sequence of
alpha-WOLF 8
(isoform 1)

MAEIGYSVCAKLIEVIGSELIKEICDTWGYKSLLEDLNKTVLTV
RNVLIQAGVMRELTSEQQGFIADLKDVVYDADDLFDKLLTRAE
RKQIDGNEISEKVRRFFSSSNKIGQAYYMSRKVKEIKKQLDEIV
DRHTKFGFSAEFIPVCRERGNERETRSYIDVKNILGRDKDKNDII
DRLLNRNGNEACSFLTIVGAGGLGKTALAQLVFNDERVKIEFH
DLRYWVCVSDQDGGQFDVKEILCKILEVVTKEKVDNSSTLELV
QSQFQEKLRGKKYFLVLDDVWNEDREKWLPLEELLMLGQGGS
KVVVTARSEKTANVIGKRHFYTLECLSPDYSWSLFEMSAFQKG

TABLE 2-continued

Sequence information.

|  |  |
|---|---|
|  | HEQENHHELVDIGKKIVEKCYNNPLAITVVGSLLYGEEISKWRS<br>FEMSELAKIGNGDNKILPILKLSYHNLIPSLKSCFSYCAVFPKDH<br>EIKKEMLIDLWIAQGYVVALDGGQSIEDAAEEHFVILLRRCFFQ<br>DVKKDEYGDVDSVKIHDLMHDVAQEVGREEICVVNDNTKNL<br>GDKIRHVHGDVNRYAQRVSLCSHSHKIRSYIGGDCEKRCVDTL<br>IDKWMCLRMLDLSWSDVKNLPNSIGKLLHLRYLNLSDNRNLKI<br>LPDAITRLHNLQTLLLKDCRSLKELPKDFCKLVKLRHLDLWGC<br>DDLIGMPFGMDKLTSLRILPNIVVGRKEQSVDDELKALKGLTEI<br>KGDIDIKICENYRIVEGMNDTGGAGYLKSMKHLREIGITFDGGC<br>VNPEAVLATLEPPSNIKSLSIHRFDGKTLPVWGRAEINWAISLSH<br>LVDIQLWHCRNLQEMPVLSKLPHLKSLELYNLISLEYMESTSRS<br>SSSDTEAATPELPTFFPSLEKLTLWGLEKLKGLGNRRSSSFPRLS<br>ELKIMECPDLTWFPPCPSLEKLTLWRLDKLKGFGNRRSSTFPRL<br>SELEIKKCPDLTSFPSCPSLEKLELKESNEALQIIVKITTRGKEKE<br>ENNNAGVRNSQDDDKVKLRKMVIDNLGYLKSLPTNCLTHLDL<br>TISDSKEGEGEWEVGDAFQKCVSSLRSLTIIGNHGINKVKRLSG<br>RTGLEHFTLLESLKLSDIEDQEDEGEDNIIFWKSFPQNLRSLRIK<br>DSDKMTSLPMGMQYLTSLQTLYLHHCYELNSLPEWISSLSSLQ<br>YLRIYYCPALKSLPEAMRNLTSLQTLGISDCPDLVKRCRKPNGK<br>DYPKIQHIPYWSIEHQVLNEYW |
| SEQ ID No: 7:<br>protein<br>sequence of<br>alpha-WOLF 8<br>(isoform 2) | MAEIGYSVCAKLIEVIGSELIKEICDTWGYKSLLEDLNKTVLTV<br>RNVLIQAGVMRELTSEQQGFIADLKDVVYDADDLFDKLLTRAE<br>RKQIDGNEISEKVRRFFSSSNKIGQAYYMSRKVKEIKKQLDEIV<br>DRHTKFGFSAEFIPVCRERGNERETRSYIDVKNILGRDKDKNDII<br>DRLLNRNGNEACSFLTIVGAGGLGKTALAQLVFNDERVKIEFH<br>DLRYWVCVSDQDGGQFDVKEILCKILEVVTKEKVDNSSTLELV<br>QSQFQEKLRGKKYFLVLDDVWNEDREKWLPLEELLMLGQGGS<br>KVVVTARSEKTANVIGKRHFYTLECLSPDYSWSLFEMSAFQKG<br>HEQENHHELVDIGKKIVEKCYNNPLAITVVGSLLYGEEISKWRS<br>FEMSELAKIGNGDNKILPILKLSYHNLIPSLKSCFSYCAVFPKDH<br>EIKKEMLIDLWIAQGYVVALDGGQSIEDAAEEHFVILLRRCFFQ<br>DVKKDEYGDVDSVKIHDLMHDVAQEVGREEICVVNDNTKNL<br>GDKIRHVHGDVNRYAQRVSLCSHSHKIRSYIGGDCEKRCVDTL<br>IDKWMCLRMLDLSWSDVKNLPNSIGKLLHLRYLNLSDNRNLKI<br>LPDAITRLHNLQTLLLKDCRSLKELPKDFCKLVKLRHLDLWGC<br>DDLIGMPFGMDKLTSLRILPNIVVGRKEQSVDDELKALKGLTEI<br>KGDIDIKICENYRIVEGMNDTGGAGYLKSMKHLREIGITFDGGC<br>VNPEAVLATLEPPSNIKSLSIHRFDGKTLPVWGRAEINWAISLSH<br>LVDIQLWHCRNLQEMPVLSKLPHLKSLELYNLISLEYMESTSRS<br>SSSDTEAATPELPTFFPSLEKLTLWGLEKLKGLGNRRSSSFPRLS<br>ELKIMECPDLTWFPPCPSLEKLTLWRLDKLKGFGNRRSSTFPRL<br>SELEIKKCPDLTSFPSCPSLEKLELKESNEALQIIVKITTRGKEKE<br>ENNNAGVRNSQDDDKVKLRKMVIDNLGYLKSLPTNCLTHLDL<br>TISDSKEGEGEWEVGDAFQKCVSSLRSLTIIGNHGINKVKRLSG<br>RTGLEHFTLLESLKLSDIEDQEDEGEDNIIFWKSFPQNLRSLRIK<br>DSDKMTSLPMGMQYLTSLQTLYLHHCYELNSLPEWISSLSSLQ<br>YLRIYYCPALKSLPEAMRNLTSLQTLGISDCPDLVKRCRKPNGK<br>DYPKIQHIPYWSIEHQLLNTSLILNAPNLQDMD |
| SEQ ID No: 8:<br>Forward primer<br>LRR domain<br>(Alpha) | ACAAGTGGATGTGTCTTAGG |
| SEQ ID No: 9:<br>Reverse primer<br>LRR domain | TTCGCCCTCATCTTCCTGG |
| SEQ ID No: 10:<br>Forward primer<br>LRR domain<br>(Beta) | TCACGTGGGTTGTGTTGT |
| SEQ ID No: 11:<br>Amplicon of<br>LRR domain of<br>the alpha-<br>WOLF 8 allele | ACAAGTGGATGTGTCTTAGGATGTTGGACTTGTCATGGTCGG<br>ATGTTAAAAATTTGCCTAATTCAATAGGTAAATTGTTGCACT<br>TGAGGTATCTTAACCTGTCAGATAATAGAAATCTAAAGATA<br>CTTCCTGATGCAATTACAAGACTGCATAATTTGCAGACACTG<br>CTTTTAAAAGATTGCAGAAGTTTAAAGGAGTTGCCAAAAGA<br>TTTTTGCAAATTGGTCAAACTGAGACACTTGGATTTATGGGG<br>TTGTGATGATTTGATTGGTATGCCATTTGGAATGGATAAGCT<br>AACTAGTCTTAGAATACTACCAAACATTGTGGTGGGTAGGA<br>AGGAACAAAGTGTTGATGATGAGCTGAAAGCCCTTAAAGGC<br>CTCACCGAGATAAAAGGCGACATTGATATCAAAATCTGTGA<br>AAATTATAGAATAGTTGAAGGCATGAATGACACAGGAGGAG<br>CTGGGTATTTGAAGAGCATGAAACATCTCAGGGAGATTGGT<br>ATTACATTTGATGGTGGATGTGTTAACCCTGAAGCTGTGTTG<br>GCAACCCTAGAGCCACCTTCAAATATCAAGAGCTTATCTATA |

TABLE 2-continued

Sequence information.

|  |  |
|---|---|
|  | CATCGTTTTGATGGTAAAACACTTCCAGTATGGGGAAGAGC<br>AGAGATTAATTGGGCAATCTCCCTCTCACATCTTGTCGACAT<br>CCAGCTTTGGCATTGTCGTAATTTGCAGGAGATGCCAGTGCT<br>GAGTAAACTGCCTCATTTGAAATCACTGGAACTTTATAATTT<br>GATTAGTTTAGAGTACATGGAGAGCACAAGCAGAAGCAGTA<br>GCAGTGACACAGAAGCAGCAACACCAGAATTACCAACATTC<br>TTCCCTTCCCTTGAAAAACTTACACTTTGGGGTCTGGAAAAG<br>TTGAAGGGTTTGGGGAACAGGAGATCGAGTAGTTTTCCCCG<br>CCTCTCTGAATTGAAAATCATGGAATGCCCAGATCTAACGTG<br>GTTTCCTCCCTGTCCAAGCCTTGAAAAACTTACACTTTGGCG<br>TCTGGACAAGTTGAAGGGTTTTGGGAACCGGAGATCGAGTA<br>CTTTTCCCCGCCTCTCTGAATTGAAATCAAGAAATGCCCAG<br>ATCTAACGTCATTTCCTTCTTGTCCAAGCCTTGAGAAGTTGG<br>AATTGAAAGAAAGCAATGAAGCATTGCAAATAATAGTAAAA<br>ATAACAACAAGAGGTAAAGAAAAAGAAGAGAACAATAATG<br>CTGGTGTTAGAAATTCACAAGATGATGACAAAGTCAAATTA<br>CGGAAGATGGTGATAGACAATCTGGGTTATCTCAAATCACT<br>GCCCACAAATTGTCTTACTCACCTCGACCTTACAATAAGTGA<br>TTCCAAGGAGGGGGAGGGTGAATGGGAAGTTGGGGATGCAT<br>TTCAGAAGTGTGTATCTTCTTTGAGAAGCCTCACCATAATCG<br>GAAATCACGGAATAAATAAAGTGAAGAGACTGTCTGGAAGA<br>ACAGGGTTGGAGCATTTCACTCTGTTGGAATCACTCAAACTT<br>TCAGATATAGAAGACCAGGAAGATGAGGGCGAA |
| SEQ ID No: 12:<br>amino acid<br>sequence<br>encoded by<br>amplicon of<br>LRR domain<br>alpha Wolf 8 | KWMCLRMLDLSWSDVKNLPNSIGKLLHLRYLNLSDNRNLKILP<br>DAITRLHNLQTLLLKDCRSLKELPKDFCKLVKLRHLDLWGCDD<br>LIGMPFGMDKLTSLRILPNIVVGRKEQSVDDELKALKGLTEIKG<br>DIDIKICENYRIVEGMNDTGGAGYLKSMKHLREIGITFDGGCVN<br>PEAVLATLEPPSNIKSLSIHRFDGKTLPVWGRAEINWAISLSHLV<br>DIQLWHCRNLQEMPVLSKLPHLKSLELYNLISLEYMESTSRSSS<br>SDTEAATPELPTFFPPSLEKLTLWGLEKLKGLGNRRSSSFPRLSEL<br>KIMECPDLTWFPPCPSLEKLTLWRLDKLKGFGNRRSSTFPRLSE<br>LEIKKCPDLTSFPSCPSLEKLELKESNEALQIIVKITTRGKEKEEN<br>NNAGVRNSQDDDKVKLRKMVIDNLGYLKSLPTNCLTHLDLTIS<br>DSKEGEGEWEVGDAFQKCVSSLRSLTIIGNHGINKVKRLSGRTG<br>LEHFTLLESLKLSDIEDQEDEGE |
| SEQ ID No: 13:<br>Amplicon of<br>LRR domain of<br>the beta-WOLF<br>0 allele | TCACGTGGGTTGTGTTGTCGATAGAGATCCAGAAATAGTCTT<br>TTTATGTAGCAATAAGATTCGTTCGTATATTAGCGGTCGCTG<br>CATAAAGAATCCGGTGGATTCACAAATAGACAACTGGATGT<br>GCCTTAGGGTGTTGGACTTGTCAGATTCATGTGTTAAAGATT<br>TGTCTGATTCAATAGGTAAGCTGCTGCACTTAAGGTATCTTA<br>ACCTCTCTTCTAATATAAAGTTGGAGATAATCCCTGATGCAA<br>TTACAAGACTGCATAACTTGCAGACACTACTTTTAGAAGATT<br>GCAGAAGTTTAAAGGAGTTGCCAAAAGATTTTTGCAAATTG<br>GTCAAACTGAGGCACTTGGAATTACAGGGTTGTCATGATTTG<br>ATTGGTATGTCATTTGGAATGGATAAGCTAACTAGTCTTAGA<br>ATACTACCAAACATTGTGGTGGGTAGGAAGGAACAAAGTGT<br>TGATGATGAGCTGAAAGCCCTAAAAGGCCTCACCGAGATAA<br>AAGGCTCCATTGATATCACAATCTATTCAAAATATAGAAGA<br>GTTGAAGGCATGAATGGCACAGGAGGAGGAGCTGGGTATTT<br>GAAGAGCATGAAACATCTCACGGGGGTTAATATTACATTTG<br>ATGAAGGTGGATGTGTTAACCCTGAAGCTGTGTATTTGAAG<br>AGCATGAAACATCTCACGAGGGTTATTATTATATTTGATTAT<br>AAAGGTGGATGTGTTAACCCTGAAGCTGTGTTGGCAACCCT<br>AGAGCCACCTTCAAATATCAAGAGGTTAGAGATGTGGCATT<br>ACAGTGGTACAACAATTCCAGTATGGGGAAGAGCAGAGATT<br>AATTGGGCAATCTCCCTCTCACATCTTGTCGACATCACGCTT<br>GAAGATTGTTACAATTTGCAGGAGATGCCAGTGCTGAGTAA<br>ACTGCCTCATTTGAAATCACTGGAACTTACAGAGTTGGATAA<br>CTTAGAGTACATGGAGAGTAGAAGCAGCAGCAGTAGCAGTG<br>ACACAGAAGCAGCAACACCAGAATTACCAACATTCTTCCCT<br>TCCCTTGAAAAACTTACACTTTGGCGTCTGGACAAGTTGAAG<br>GGTTTTGGGAACAGGAGATCGAGTAGTTTTCCCCGCCTCTCT<br>AAATTGGAAATCTGGAAATGTCCAGATCTAACGTCATTTCCT<br>TCTTGTCCAAGCCTTGAGAGTTGGAATTGAAAGAAAACAA<br>TGAAGCGTTGCAAATAATAGTAAAAATAACAACAACAAGAG<br>GTAAAGAAGAAAAGAAGAAGACAAGAATGCTGGTGTTGG<br>AAATTCACAAGATGATGACAATGTCAAATTATGGAAGGTGG<br>AAATAGACAATCTGGGTTATCTCAAATCACTGCCCACAAATT<br>GTCTGACTCACCTCGACCTTACAATAAGTGATTCCAAGGAGG<br>GGGAGGGTGAATGGGAAGTTGGGGATGCATTTCAGAAGTGT<br>GTATCTTCTTTGAGAAGCCTCACCATAATCGGAAATCACGGA<br>ATAAATAAAGTGAAGAGACTGTCTGGAAGAACAGGGTTGGA<br>GCATTTCACTCTGTTGGAATCACTCAAACTTTCAGATATAGA<br>AGACCAGGAAGATGAGGGCGAA |

TABLE 2-continued

Sequence information.

```
SEQ ID No: 14:      HVGCVVDRDPEIVFLCSNKIRSYISGRCIKNPVDSQIDNWMCLR
amino acid          VLDLSDSCVKDLSDSIGKLLHLRYLNLSSNIKLEIIPDAITRLHNL
sequence            QTLLLEDCRSLKELPKDFCKLVKLRHLELQGCHDLIGMSFGMD
encoded by          KLTSLRILPNIVVGRKEQSVDDELKALKGLTEIKGSIDITIYSKYR
amplicon of         RVEGMNGTGGGAGYLKSMKHLTGVNITFDEGGCVNPEAVYL
LRR domain          KSMKHLTRVIIIFDYKGGCVNPEAVLATLEPPSNIKRLEMWHYS
Beta Wolf 0         GTTIPVWGRAEINWAISLSHLVDITLEDCYNLQEMPVLSKLPHL
(Viroflay)          KSLELTELDNLEYMESRSSSSSSDTEAATPELPTFFPSLEKLTLW
                    RLDKLKGFGNRRSSSFPRLSKLEIWKCPDLTSFPSCPSLEELELK
                    ENNEALQIIVKITTTRGKEEKEEDKNAGVGNSQDDDNVKLWK
                    VEIDNLGYLKSLPTNCLTHLDLTISDSKEGEGEWEVGDAFQKC
                    VSSLRSLTIIGNHGINKVKRLSGRTGLEHFTLLESLKLSDIEDQE
                    DEGE
```

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Testing for Resistance to *Peronospora Farinosaf Sp. Spinaciae* in Spinach Plants The resistance to downy mildew infection was assayed as described by Irish et al. (2008; *Phytopathol.* 98: 894-900), using a differential set. Spinach plants of the invention were sown along with spinach plants from different other genotypes (see Table 3) in trays containing Scotts Redi-Earth medium, and fertilized twice a week after seedling emergence with Osmocote Peter's (13-13-13) fertilizer (Scotts). Plants were inoculated with a sporangial suspension (2.5× $10^5$/ml) of a pathogenic race of *Peronospora farinosa* f. sp. *spinaciae* at the first true leaf stage. In this manner, 16 officially recognized pathogenic races were tested.

The inoculated plants were placed in a dew chamber at 18° C. with 100% relative humidity for a 24 h period, and then moved to a growth chamber at 18° C. with a 12 h photoperiod for 6 days. After 6 days, the plants were returned to the dew chamber for 24 h to induce sporulation, and they were scored for disease reaction.

Plants for this specific test were scored as resistant, intermediately resistant, or susceptible based on symptoms of chlorosis and signs of pathogen sporulation on the cotyledons and true leaves, as described by Irish et al. (2007; *Plant Dis.* 91: 1392-1396). Plants exhibiting no evidence of chlorosis and sporulation were in this specific test considered as resistant. Resistant plants were re-inoculated to assess whether plants initially scored as resistant had escaped infection, or whether they were truly resistant. Plants that showed only symptoms of chlorosis, or sporulation occurring only on the tips of the cotyledons were scored as intermediately resistant. Plants showing more than these symptoms of downy mildew infection were scored as being susceptible.

Table 1 shows the resistance of a plant carrying the alpha-WOLF 8 allele to each one of these pathogenic races. Table 3 shows the differential set of spinach downy mildew races and the resistance of various spinach varieties (hybrids) to each one of these pathogenic races. A susceptible reaction is scored as "+" (indicating a successful infection by the fungus, with sporulation occurring on the entire cotyledon), and resistance is depicted as "−" (absence of sporulation on the cotyledons). A weak resistance response is indicated as "(−)", which in practice means a slightly reduced level of infection (with only symptoms of chlorosis, or sporulation only occurring on the tips of the cotyledons in the differential seedling test).

TABLE 3

| Races/plants | Viroflay | Resistoflay | Califlay | Clermont | Campania | Boeing | Lion | Lazio | Whale | Polka | Pigeon | Meerkat |
|---|---|---|---|---|---|---|---|---|---|---|---|---|
| Pfs:1  | + | − | − | − | −   | − | − | − | −   | −   | − | − |
| Pfs:2  | + | − | + | − | −   | − | − | − | −   | −   | − | − |
| Pfs:3  | + | + | − | − | −   | − | − | − | −   | −   | − | − |
| Pfs:4  | + | + | + | − | −   | − | − | − | (−) | +   | − | − |
| Pfs:5  | + | + | − | + | −   | − | − | − | −   | −   | − | − |
| Pfs:6  | + | + | + | + | +   | − | − | − | (−) | +   | − | − |
| Pfs:7  | + | + | + | + | −   | − | − | − | (−) | +   | − | − |
| Pfs:8  | + | + | − | + | +   | + | − | − | −   | −   | − | − |
| Pfs:9  | + | + | − | + | +   | − | − | − | −   | −   | − | − |
| Pfs:10 | + | + | + | + | +   | + | + | − | +   | +   | − | − |
| Pfs:11 | + | + | − | + | −   | − | − | + | −   | −   | − | − |
| Pfs:12 | + | + | − | + | +   | + | − | + | −   | −   | − | − |
| Pfs:13 | + | + | + | + | (−) | − | − | + | +   | (−) | − | − |
| Pfs:14 | + | + | − | + | +   | + | − | + | (−) | −   | + | − |
| Pfs:15 | + | + | + | − | −   | − | − | − | +   | +   | − | − |
| Pfs:16 | + | + | − | + | −   | − | − | + | −   | −   | + | + |

Example 2: Amplification of the LRR Domain-Encoding Region

The isolated genomic DNA of a spinach plant comprising the alpha-WOLF 8 allele, of which a representative sample of seed was deposited with the NCIMB under NCIMB accession number 42646 was used in polymerase chain reactions (PCR), using forward primer ACAAGTGGATGT-GTCTTAGG (SEQ ID NO:8) and reverse primer TTCGC-CCTCATCTTCCTGG (SEQ ID NO:9). The primer pair amplifies the LRR domain-encoding region of an alpha-WOLF gene, and has been designed for selectively amplifying part of a WOLF gene, and not of other CC-NBS-LRR protein-encoding genes.

PCR conditions for amplifying the LRR domain-encoding region of an alpha-WOLF gene using primers having SEQ ID NO:8 and SEQ ID NO:9 were as follows, using Platinum Taq enzyme (Thermo Fisher Scientific):
 3 minutes at 95° C. (initial denaturing step)
 40 amplification cycles, each cycle consisting of: 30 seconds denaturation at 95° C., 30 seconds annealing at 60° C., and 30 seconds extension at 72° C.
 2 minutes at 72° C. (final extension step)

The isolated genomic DNA of a spinach plant of variety Viroflay comprising the beta-WOLF 0 allele was used in polymerase chain reactions (PCR), using forward primer TCACGTGGGTTGTGTTGT (SEQ ID NO:10) and reverse primer TTCGCCCTCATCTTCCTGG (SEQ ID NO:9). The primer pair amplifies the LRR domain-encoding region of a beta-WOLF gene, and has been designed for selectively amplifying part of a WOLF gene, and not of other CC-NBS-LRR protein-encoding genes.

PCR conditions for amplifying the LRR domain-encoding region of a beta-WOLF gene using primers having SEQ ID NO:9 and SEQ ID NO:10 were as follows, using Platinum Taq enzyme (Thermo Fisher Scientific):
 3 minutes at 95° C. (initial denaturing step)
 40 amplification cycles, each cycle consisting of: 30 seconds denaturation at 95° C., 50 seconds annealing at 58° C. and 50 seconds extension at 72° C.
 2 minutes at 72° C. (final extension step)

The PCR products were visualized on agarose gel (not shown), and DNA was purified from the PCR reaction. Subsequently the sequence of the PCR products was determined using methods well known in the art.

The sequence of the LRR domain of the alpha WOLF 8 allele amplified by primers having SEQ ID NO:8 and SEQ ID NO:9 is provided in Table 2 under SEQ ID NO:11.

The sequence of the LRR domain of the beta-WOLF 0 allele amplified by primers having SEQ ID NO:9 and SEQ ID NO:10 is provided in Table 2 under SEQ ID NO:13.

Finally, the obtained sequences were translated into the corresponding amino acid sequence of the LRR domain having SEQ ID NO:12 and SEQ ID NO:14 for the alpha-WOLF 8 allele and the beta-WOLF 0, respectively (See also Table 2).

If PCR products were to be sequenced using SMRT sequencing (Pacific Biosciences), PCR primers and PCR conditions were different.

To the above-mentioned forward primers the following standard amplification sequence was added: GCAGTC-GAACATGTAGCTGACTCAGGTCAC (SEQ ID NO:19).

To the reverse primer, the following standard amplification sequence was added: TGGATCACTTGTGCAAGCAT-CACATCGTAG (SEQ ID NO:20).

Example 3: Introducing Alpha-WOLF 8 Allele in a Plant not Carrying the Allele A spinach plant comprising the alpha-WOLF 8 allele, of which a representative sample of seed was deposited with the NCIMB under NCIMB accession number 42646 was crossed with a plant of variety Viroflay carrying the beta-WOLF 0 allele to obtain a F1 generation. Subsequently, a F1 plant was selfed to obtain a F2 population.

Plants of the F2 population were assayed as described in Example 1 for resistance to *Peronospora farinosa* f. sp. *spinaciae* Pfs:15. Approximately 75% of the plants scored completely resistant in the assay.

Genomic DNA of each plant of the same F2 population was isolated and used in two different polymerase chain reactions (PCR). The first PCR reaction was done using primers for amplifying the LRR domain of an alpha-WOLF allele and the second PCR reaction was done using primers for amplifying the LRR domain of a beta-WOLF allele, both as described in Example 2.

The PCR products were visualized on agarose gel (not shown), this demonstrated that approximately 25% of the plant only contained an alpha-WOLF fragment, approximately 50% contained both an alpha- and a beta-WOLF fragment, and that the remaining approximately 25% of the plants only contained a beta-WOLF fragment. The plants containing the alpha-WOLF fragment completely correlated with the plants that scored resistant for Pfs:15. The plants only comprising the beta-WOLF fragment completely correlated with the plants that scored susceptible for Pfs:15.

DNA from the PCR reaction was purified, and subsequently the sequence of the PCR products was determined. The alpha-WOLF PCR products gave a sequence that corresponded to the sequence of SEQ ID NO:11, the genomic sequence of the LRR domain of the alpha-WOLF 8 allele. The beta-WOLF PCR products gave a sequence that corresponded to the sequence of SEQ ID NO:13 the genomic sequence of the LRR domain of the beta-WOLF 0 allele.

The invention is further described by the following numbered paragraphs:

1. An allele designated alpha-WOLF 8 which confers resistance to at least one *Peronospora farinosa* f. sp. *spinaciae* race when present in a spinach plant, wherein the protein encoded by said allele is a CC-NBS-LRR protein that comprises in its amino acid sequence: a) the motif "MAEIGYSVC" (SEQ ID NO:15) at its N-terminus; and b) the motif "KWMCLR" (SEQ ID NO:16); and wherein the LRR domain of the protein has in order of increased preference at least 92%, 93%, 94%, 95%, 96%, 97%, 98%, 99%, 100% sequence similarity to SEQ ID NO:12.

2. The allele of paragraph 1, wherein the allele when homozygously present in a spinach plant confers complete resistance to *Peronospora farinosa* f. sp. *spinaciae* races Pfs:1, Pfs:2, Pfs:6, Pfs:8 and Pfs:15, and confers intermediate resistance to Pfs:5, Pfs:10 and Pfs:16, and does not confer resistance to Pfs:3, Pfs:4, Pfs:7, Pfs:9, Pfs:11, Pfs:12, Pfs:13 and Pfs:14.

3. The allele of paragraph 1 or 2, wherein the allele has a genomic nucleotide sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:1.

4. The allele of paragraph 1 or 2, wherein the allele has a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:2.

5. The allele of paragraph 1 or 2, wherein the allele has a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:3.

6. The allele of paragraph 1 or 2, wherein the allele has a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:4.

7. The allele of paragraph 1 or 2, wherein the allele encodes a protein having an amino acid sequence which in order of increased preference has at least 92%, 93%, 94%, 95%, 96%, 97%, 98%, 99%, 100% sequence similarity to SEQ ID NO:5.

8. The allele of paragraph 1 or 2, wherein the allele encodes for a protein having an amino acid sequence which in order of increased preference has at least 92%, 93%, 94%, 95%, 96%, 97%, 98%, 99%, 100% sequence similarity to SEQ ID NO:6.

9. The allele of paragraph 1 or 2, wherein the allele encodes for a protein having an amino acid sequence which in order of increased preference has at least 92%, 93%, 94%, 95%, 96%, 97%, 98%, 99%, 100% sequence similarity to SEQ ID NO:7.

10. A spinach plant comprising the allele of any one of the paragraphs 1 to 9, of which a representative sample of seed capable of growing into a plant comprising said allele was deposited with the NCIMB under NCIMB accession number 42646.

11. The spinach plant of paragraph 10, wherein the plant is an agronomically elite plant.

12. The spinach plant of paragraph 11, wherein the agronomically elite plant is a hybrid variety or an inbred line.

13. The spinach plant of paragraph 11, further comprising a genetic determinant resulting in resistance against *Peronospora farinosa* f. sp. *spinaciae* races Pfs:1 to Pfs:16.

14. Propagation material capable of developing into and/or being derived from a spinach plant as defined in any of the paragraphs 10 to 13, wherein the propagation material comprises the allele of any of the paragraphs 1 to 9 and wherein the propagation material is selected from a group consisting of a microspore, a pollen, an ovary, an ovule, an embryo, an embryo sac, an egg cell, a cutting, a root, a root tip, a hypocotyl, a cotyledon, a stem, a leaf, a flower, an anther, a seed, a meristematic cell, a protoplast, a cell, or a tissue culture thereof.

15. Cell of a spinach plant, which cell comprises the allele of any of the paragraphs 1 to 9.

16. A method of producing a hybrid spinach seed comprising crossing a first parent spinach plant with a second parent spinach plant and harvesting the resultant hybrid spinach seed, wherein said first parent spinach plant comprises the allele of any of the paragraphs 1 to 9.

17. The method of paragraph 16, wherein the first and/or second parent is a plant of an inbred line.

18. A hybrid spinach plant grown from the seed produced by the method of paragraph 16 or paragraph 17.

19. Method for identifying or selecting a spinach plant carrying the allele of any of the paragraphs 1 to 9, comprising determining the presence of a genomic nucleotide sequence or a part thereof in the genome of a plant, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:1.

20. Method for identifying or selecting a spinach plant carrying the allele of any of the paragraphs 1-4 and 7, comprising determining the presence of a genomic nucleotide sequence or a part thereof in the genome of a plant, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:2.

21. Method for identifying or selecting a spinach plant carrying the allele of any of the paragraphs 1-3, 5 and 8, comprising determining the presence of a genomic nucleotide sequence or a part thereof in the genome of a plant, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:3.

22. Method for identifying or selecting a spinach plant carrying the allele of any of the paragraphs 1-3, 6 and 9, comprising determining the presence of a genomic nucleotide sequence or a part thereof in the genome of a plant, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:4.

23. The method of any of the paragraphs 19 to 22, comprising determining the presence of the LRR domain as defined in paragraph 1.

24. The method of paragraph 23, wherein the LRR domain is determined by using a primer pair to amplify the LRR domain, wherein the forward primer is a nucleic acid molecule having the sequence of SEQ ID NO:8.

25. The method of paragraph 23, wherein the LRR domain is determined by using a primer pair to amplify the LRR domain, wherein the reverse primer is a nucleic acid molecule having the sequence of SEQ ID NO:9.

26. Primer pair comprising a forward primer which is a nucleic acid molecule having the sequence of SEQ ID NO:8 and a reverse primer which is a nucleic acid molecule having the sequence of SEQ ID NO:9.

27. A method for producing a spinach plant showing resistance to *Peronospora farinosa* f. sp. *spinaciae* comprising: (a) crossing a plant comprising the allele of any one of the paragraphs 1 to 9, with another plant; (b) optionally performing one or more rounds of selfing and/or crossing; (c) selecting after one or more rounds of selfing and/or crossing for a plant that comprises said allele of any of the paragraphs 1 to 9.

28. The method of paragraph 27, wherein the selection of a plant comprising the allele comprises determining the presence of the allele according the method of anyone of the paragraphs 19 to 25.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An agronomically elite spinach plant comprising an allele which confers resistance to at least one *Peronospora farinosa* f. sp. *spinaciae* race when present in a spinach plant and encoding a a CC-NBS-LRR protein
   that has at least 92% sequence identity to a protein comprising an amino acid sequence selected from the group consisting of SEQ ID NO: 5, SEQ ID NO: 6 and SEQ ID NO: 7; wherein said protein comprises in its amino acid sequence:
   a) SEQ ID NO: 15,
   b) SEQ ID NO: 16,
   and wherein the LRR domain of the protein has at least 95% sequence identity to SEQ ID NO: 12.

2. The agronomically elite spinach plant of claim 1, wherein the allele when homozygously present in a spinach plant confers complete resistance to *Peronospora farinosa* f. sp. *spinaciae* races Pfs:1, Pfs:2, Pfs:6, Pfs:8 and Pfs:15, and confers intermediate resistance to Pfs:5, Pfs:10 and Pfs:16, and does not confer resistance to Pfs:3, Pfs:4, Pfs:7, Pfs:9, Pfs:11, Pfs:12, Pfs:13 and Pfs:14.

3. An agronomically elite spinach plant comprising an allele which when homozygously present in a spinach plant encodes a protein that confers complete resistance to at least *Peronospora farinosa* f. sp. *spinaciae* races Pfs:1, Pfs:2, Pfs:6, Pfs:8 and Pfs:15, and intermediate resistance to Pfs:5, Pfs:10 and Pfs:16, and does not confer resistance to Pfs:3, Pfs:4, Pfs:7, Pfs:9, Pfs:11, Pfs:12, Pfs:13 and Pfs:14, wherein the allele has a genomic nucleotide sequence which is SEQ ID NO: 1.

4. The agronomically elite spinach plant of claim 1, wherein the allele encodes a protein comprising an amino acid sequence having at least 95% sequence identity to SEQ ID NO: 5.

5. The agronomically elite spinach plant of claim 1, wherein the allele encodes a protein comprising an amino acid sequence having at least 95% sequence identity to SEQ ID NO: 6.

6. The agronomically elite spinach plant of claim 1, wherein the allele encodes a protein comprising an amino acid sequence having at least 95% sequence identity to SEQ ID NO:7.

7. The agronomically elite spinach plant as claimed in claim 1, of which a representative sample of seed capable of growing into a plant comprising said allele was deposited with the NCIMB under accession number 42646.

8. The agronomically elite spinach plant of claim 1 or 3, wherein the agronomically elite plant is a hybrid variety or an inbred line.

9. A propagation material capable of developing into the agronomically elite spinach plant as claimed in claim 1 or 3 and wherein the propagation material comprises a microspore, a pollen, an ovary, an ovule, an embryo, an embryo sac, an egg cell, a cutting, a root, a root tip, a hypocotyl, a cotyledon, a stem, a leaf, a flower, an anther, a seed, a meristematic cell, a protoplast, a cell, or a tissue culture thereof.

10. A cell of the agronomically elite spinach plant as claimed in claim 1 or 3.

11. A method of producing an F1 hybrid spinach seed comprising crossing a first parent spinach plant with a second parent spinach plant and harvesting the resultant hybrid spinach seed, wherein said first parent spinach plant and/or said second parent spinach plant is the agronomically elite spinach plant as claimed in claim 1 or 3.

12. The method of claim 11, wherein the first and/or second parent is a plant of an inbred line.

13. An F1 hybrid spinach plant grown from the seed produced by the method of claim 11, wherein the F1 hybrid plant carries the allele which confers resistance to at least one *Peronospora farinosa* f. sp. *spinaciae* race when present in a spinach plant and encoding a CC-NBS-LRR protein that has at least 92% sequence identity to a protein comprising an amino acid sequence selected from the group consisting of SEQ ID NO: 5, SEQ ID NO: 6 and SEQ ID NO: 7; wherein said protein comprises in its amino acid sequence:
    a) SEQ ID NO: 15,
    b) SEQ ID NO: 16,
    and wherein the LRR domain of the protein has at least 95% sequence identity to SEQ ID NO: 12.

14. A method for producing a spinach plant showing resistance to *Peronospora farinosa* f. sp. *spinaciae* comprising: (a) crossing the plant as claimed in claim 1 or 3 with another spinach plant; (b) optionally performing one or more rounds of selfing and/or crossing; (c) optionally selecting after the crossing or the one or more rounds of selfing and/or crossing for a plant that comprises said allele.

15. The method of claim 14, wherein the method includes performing the optional selection, and the selection of the plant comprising the allele expressing the protein comprises determining the presence of the allele according to a method comprising any one or more of:
    determining the presence of a nucleotide sequence in a plant, wherein said sequence has at least 95% sequence identity to SEQ ID NO: 1, or
    determining the presence of a nucleotide sequence in a plant, wherein said sequence has at least 95% sequence identity to SEQ ID NO: 2, or
    determining the presence of a nucleotide sequence in a plant, wherein said sequence has at least 95% sequence identity to SEQ ID NO: 3, or
    or
    determining the presence of a nucleotide sequence encoding a LRR domain having at least 95% sequence identity to SEQ ID NO: 11.

16. The method of claim 14, wherein the method includes performing the optional one or more rounds of selfing and/or crossing and the optional selection, and the selection of the plant comprising the allele expressing the protein comprises determining the presence of the allele according to a method comprising any one or more of:
    determining the presence of a nucleotide sequence in the genome of a plant, wherein said sequence has at least 95% sequence identity to SEQ ID NO: 1, or
    determining the presence of a nucleotide sequence in a plant, wherein said sequence has at least 95% sequence identity to SEQ ID NO: 2, or
    determining the presence of a nucleotide sequence in a plant, wherein said sequence has at least 95% sequence identity to SEQ ID NO: 3, or
    determining the presence of a nucleotide sequence encoding a LRR domain having at least 95% sequence identity to SEQ ID NO: 11.

17. A method of producing a hybrid spinach seed comprising crossing a first parent spinach plant with a second parent spinach plant and harvesting the resultant hybrid spinach seed, wherein said first parent spinach plant and/or said second parent spinach is the plant of claim 1 or 3.

18. The plant of claim 1, wherein the allele encodes a protein having at least 96% sequence identity to SEQ ID NO: 5, 6 or 7.

19. The plant of claim 1, wherein the allele encodes a protein having at least 97% sequence identity to SEQ ID NO: 5, 6 or 7.

20. The plant of claim 1, wherein the allele encodes a protein having at least 98% sequence identity to SEQ ID NO: 5, 6 or 7.

21. The plant of claim 1, wherein the allele encodes a protein having at least 99% sequence identity to SEQ ID NO: 5, 6 or 7.

22. The plant of claim 1, wherein the allele encodes a protein having 100% sequence identity to SEQ ID NO: 5, 6 or 7.

23. The plant of claim 4, wherein the allele encodes a protein having at least 96% sequence identity to SEQ ID NO: 5.

24. The plant of claim 4, wherein the allele encodes a protein having at least 97% sequence identity to SEQ ID NO: 5.

25. The plant of claim 4, wherein the allele encodes a protein having at least 98% sequence identity to SEQ ID NO: 5.

26. The plant of claim 4, wherein the allele encodes a protein having at least 99% sequence identity to SEQ ID NO: 5.

27. The plant of claim 4, wherein the allele encodes a protein having 100% sequence identity to SEQ ID NO: 5.

28. The plant of claim 5, wherein the allele encodes a protein having at least 96% sequence identity to SEQ ID NO: 6.

29. The plant of claim 5, wherein the allele encodes a protein having at least 97% sequence identity to SEQ ID NO: 6.

30. The plant of claim 5, wherein the allele encodes a protein having at least 98% sequence identity to SEQ ID NO: 6.

31. The plant of claim 5, wherein the allele encodes a protein having at least 99% sequence identity to SEQ ID NO: 6.

32. The plant of claim 5, wherein the allele encodes a protein having 100% sequence identity to SEQ ID NO: 6.

33. The plant of claim 6, wherein the allele encodes a protein having at least 96% sequence identity to SEQ ID NO: 7.

34. The plant of claim 6, wherein the allele encodes a protein having at least 97% sequence identity to SEQ ID NO: 7.

35. The plant of claim 6, wherein the allele encodes a protein having at least 98% sequence identity to SEQ ID NO: 7.

36. The plant of claim 6, wherein the allele encodes a protein having at least 99% sequence identity to SEQ ID NO: 7.

37. The plant of claim 6, wherein the allele encodes a protein having 100% sequence identity to SEQ ID NO: 7.

38. The plant of claim 3, wherein the allele has at least 96% sequence identity to SEQ ID NO: 1.

39. The plant of claim 3, wherein the allele has at least 97% sequence identity to SEQ ID NO: 1.

40. The plant of claim 3, wherein the allele has at least 98% sequence identity to SEQ ID NO: 1.

41. The plant of claim 3, wherein the allele has at least 99% sequence identity to SEQ ID NO: 1.

42. The plant of claim 3, wherein the allele has 100% sequence identity to SEQ ID NO: 1.

43. The method of claim 15, wherein the determining the presence of the allele expressing the protein comprises determining the presence of a genomic nucleotide sequence in a plant, wherein the sequence has at least 96% sequence identity to SEQ ID NO: 1, 2 or 3.

44. The method of claim 15, wherein the determining the presence of the allele expressing the protein comprises determining the presence of a genomic nucleotide sequence in a plant, wherein the sequence has at least 97% sequence identity to SEQ ID NO: 1, 2 or 3.

45. The method of claim 15, wherein the determining the presence of the allele expressing the protein comprises determining the presence of a genomic nucleotide sequence in a plant, wherein the sequence has at least 98% sequence identity to SEQ ID NO: 1, 2 or 3.

46. The method of claim 15, wherein the determining the presence of the allele expressing the protein comprises determining the presence of a genomic nucleotide sequence in a plant, wherein the sequence has at least 99% sequence identity to SEQ ID NO: 1, 2 or 3.

47. The method of claim 15, wherein the determining the presence of the allele expressing the protein comprises determining the presence of a genomic nucleotide sequence in a plant, wherein the sequence has 100% sequence identity to SEQ ID NO: 1, 2 or 3.

48. The method of claim 16, wherein the determining the presence of the allele expressing the protein comprises determining the presence of a genomic nucleotide sequence in a plant, wherein the sequence has at least 96% sequence identity to SEQ ID NO: 1, 2 or 3.

49. The method of claim 16, wherein the determining the presence of the allele expressing the protein comprises determining the presence of a genomic nucleotide sequence in a plant, wherein the sequence has at least 97% sequence identity to SEQ ID NO: 1, 2 or 3.

50. The method of claim 16, wherein the determining the presence of the allele expressing the protein comprises determining the presence of a genomic nucleotide sequence in a plant, wherein the sequence has at least 98% sequence identity to SEQ ID NO: 1, 2 or 3.

51. The method of claim 16, wherein the determining the presence of the allele expressing the protein comprises determining the presence of a genomic nucleotide sequence in a plant, wherein the sequence has at least 99% sequence identity to SEQ ID NO: 1, 2 or 3.

52. The method of claim 16, wherein the determining the presence of the allele expressing the protein comprises determining the presence of a genomic nucleotide sequence in a plant, wherein the sequence has 100% sequence identity to SEQ ID NO: 1, 2 or 3.

53. An agronomically elite spinach plant comprising an allele which when homozygously present in a spinach plant encodes a protein that confers complete resistance to at least *Peronospora farinosa* f. sp. *spinaciae* races Pfs:1, Pfs:2, Pfs:6, Pfs:8 and Pfs:15, and intermediate resistance to Pfs:5, Pfs:10 and Pfs:16, and does not confer resistance to Pfs:3, Pfs:4, Pfs:7, Pfs:9, Pfs:11, Pfs:12, Pfs:13 and Pfs:14, wherein the allele has a nucleotide sequence which is SEQ ID NO: 2.

54. An agronomically elite spinach plant comprising an allele which when homozygously present in a spinach plant encodes a protein that confers complete resistance to at least *Peronospora farinosa* f. sp. *spinaciae* races Pfs:1, Pfs:2, Pfs:6, Pfs:8 and Pfs:15, and intermediate resistance to Pfs:5, Pfs:10 and Pfs:16, and does not confer resistance to Pfs:3, Pfs:4, Pfs:7, Pfs:9, Pfs:11, Pfs:12, Pfs:13 and Pfs:14, wherein the allele has a nucleotide sequence which is SEQ ID NO: 3.

* * * * *

SEQUENCE LISTING

<160> NUMBER OF SEQ ID NOS: 20

<210> SEQ ID NO 1
<211> LENGTH: 8389
<212> TYPE: DNA
<213> ORGANISM: Spinacia oleracea
<220> FEATURE:
<221> NAME/KEY: unsure
<222> LOCATION: 5171..5230
<223> OTHER INFORMATION: /note="n = unknown"
<220> FEATURE:
<221> NAME/KEY: unsure
<222> LOCATION: 5553..5602
<223> OTHER INFORMATION: /note="n = unknown"

<400> SEQUENCE: 1

| | | | | | |
|---|---|---|---|---|---|
| atggccgaaa | tcggatactc | ggtttgtgcg | aaactcatcg | aagtgattgg | cagtgagctg | 60 |
| atcaaagaga | tttgtgacac | atggggttac | aaatctcttc | ttgaggacct | caacaaaact | 120 |
| gtattgacgg | tcaggaacgt | tctcattcaa | gccggggtga | tgcggagct | actagtgaa | 180 |
| caacaaggtt | tcattgcaga | ccttaaagat | gttgtttatg | atgctgatga | cttgttcgac | 240 |
| aagttactca | ctcgtgctga | gcgaaaacag | attgatggaa | acgaaatctc | tgaaaaggta | 300 |
| cgtcgttct | tttcctctag | taacaagatc | ggtcaagctt | actacatgtc | tcgtaaggtt | 360 |
| aaggaaatta | agaagcagtt | ggatgaaatt | gttgataggc | atacaaaatt | tgggtttagt | 420 |
| gccgagttta | tacctgtttg | tagggaaagg | gggaacgaga | gggaaacacg | ttcatatata | 480 |
| gatgtcaaga | atattcttgg | gagggataaa | gataagaatg | atatcataga | taggttgctt | 540 |
| aatcgtaatg | gtaatgaagc | ttgtagtttc | ctgaccatag | tgggagcggg | aggattggga | 600 |
| aaaactgctc | ttgcacaact | tgtgttcaat | gatgaaaggg | tcaaaattga | gttccatgat | 660 |
| ttgaggtatt | gggtttgtgt | ctctgatcaa | gatggggcc | aatttgatgt | gaaagaaatc | 720 |
| ctttgtaaga | ttttagaggt | ggttactaag | gagaaagttg | ataatagttc | cacattggaa | 780 |
| ttggtacaaa | gccaatttca | agagaagtta | agaggaaaga | agtacttcct | tgttcttgat | 840 |
| gatgtatgga | acgaagatcg | tgagaagtgg | cttcctttgg | aagagttgtt | aatgtttggt | 900 |
| caaggggaa | gcaaggttgt | agtgaccgca | cgttcagaga | agacagcaaa | tgtcataggg | 960 |
| aaaagacatt | tttatacact | ggaatgtttg | tcaccagatt | attcatggag | cttatttgaa | 1020 |
| atgtcggctt | ttcagaaagg | gcatgagcag | gaaaaccatc | acgaactagt | tgatattggg | 1080 |
| aaaaagattg | ttgaaaaatg | ttataacaat | ccacttgcta | taacggtggt | aggaagtctt | 1140 |
| ctttatggag | aggagataag | taagtggcgg | tcatttgaaa | tgagtgagtt | ggccaaaatt | 1200 |
| ggcaatgggg | ataataagat | tttgccgata | ttaaagctca | gttaccataa | tcttataccc | 1260 |
| tcgttgaaga | gttgcttcag | ttattgtgca | gtgtttccca | aggatcatga | aataaagaag | 1320 |
| gagatgttga | ttgatctttg | gatagcacaa | ggatacgttg | tggcacttga | tggaggtcaa | 1380 |
| agtatagaag | atgctgccga | agaacatttt | gtaattttgt | tacggagatg | tttctttcaa | 1440 |
| gatgtaaaga | aggatgaata | tggtgatgtt | gattctgtta | aaatccacga | cttgatgcac | 1500 |
| gatgtcgccc | aagaagtggg | gagggaggaa | atatgtgtag | tgaatgataa | tacaaagaac | 1560 |
| ttgggtgata | aaatccgtca | tgtacatggt | gatgtcaata | gatatgcaca | aagagtctct | 1620 |
| ctgtgtagcc | atagccataa | gattcgttcg | tatattggtg | gtgattgtga | aaaacgttgt | 1680 |
| gtggatacac | taatagacaa | gtggatgtgt | cttaggatgt | ggacttgtc | atggtcggat | 1740 |
| gttaaaaatt | tgcctaattc | aataggtaaa | ttgttgcact | tgaggtatct | taacctgtca | 1800 |
| gataatagaa | atctaaagat | acttcctgat | gcaattacaa | gactgcataa | tttgcagaca | 1860 |

```
ctgcttttaa aagattgcag aagtttaaag gagttgccaa aagattttg caaattggtc      1920 aaactgagac acttggattt atggggttgt gatgatttga ttggtatgcc atttggaatg     1980
gataagctaa ctagtcttag aatactacca aacattgtgg tgggtaggaa ggaacaaagt    2040
gttgatgatg agctgaaagc ccttaaaggc ctcaccgaga taaaaggcga cattgatatc     2100
aaaatctgtg aaaattatag aatagttgaa ggcatgaatg acacaggagg agctgggtat    2160
ttgaagagca tgaaacatct cagggagatt ggtattacat ttgatggtgg atgtgttaac    2220
cctgaagctg tgttggcaac cctagagcca ccttcaaata tcaagagctt atctatacat    2280
cgttttgatg gtaaaacact tccagtatgg ggaagagcag agattaattg ggcaatctcc    2340
ctctcacatc ttgtcgacat ccagctttgg cattgtcgta atttgcagga gatgccagtg    2400
ctgagtaaac tgcctcattt gaaatcactg gaactttata atttgattag tttagagtac    2460
atggagagca caagcagaag cagtagcagt gacacagaag cagcaacacc agaattacca    2520
acattcttcc cttcccttga aaacttaca ctttggggtc tggaaaagtt gaagggtttg     2580
gggaacagga gatcgagtag ttttccccgc ctctctgaat tgaaaatcat ggaatgccca    2640
gatctaacgt ggtttcctcc ctgtccaagc cttgaaaaac ttacactttg gcgtctggac    2700
aagttgaagg gttttgggaa ccggagatcg agtacttttc cccgcctctc tgaattggaa    2760
atcaagaaat gcccagatct aacgtcattt ccttcttgtc caagccttga aagttggaa     2820 ttgaaagaaa gcaatgaagc attgcaaata atagtaaaaa taacaacaag aggtaaagaa    2880
aaagaagaga acaataatgc tggtgttaga aattcacaag atgatgacaa agtcaaatta    2940
cggaagatgg tgatagacaa tctgggttat ctcaaatcac tgcccacaaa ttgtcttact    3000
cacctcgacc ttacaataag tgattccaag gagggggagg gtgaatggga agttggggat   3060
gcatttcaga agtgtgtatc ttctttgaga agcctcacca taatcggaaa tcacggaata    3120
aataaagtga agagactgtc tggaagaaca gggttggagc atttcactct gttggaatca    3180
ctcaaacttt cagatataga agaccaggaa gatgagggcg aagacaacat catattctgg    3240
aaatcctttc ctcaaaaacct ccgcagtttg agaattaaag actctgacaa aatgacaagt   3300
ttgcccatgg ggatgcagta cttaacctcc ctccaaaccc tctatctaca ccattgttat    3360
gaattgaatt cccttccaga atggataagc agcttatcat ctcttcaata cctgcgcata    3420
tactactgtc cagccctgaa atcactacca gaagcaatgc ggaacctcac ctcccttcag    3480
acacttggga tatcggattg tccagaccta gttaaaagat gcagaaaacc caacggcaag    3540
gactatccca aaattcaaca catccccctat tggagtatag aacatcaggt tataactagc    3600
ttgtaactaa cttgtaacta cctagtataa atacagtagt ttgtactatt ttacattcaa   3660
ttacacaatt aataaaatgt agactctcac tctctctctc taagccacga gctccaagct    3720
cgtcaatggc ttcccttctc tgttcttgct ttcttctttc ctcttcaatt cacaaattca    3780
acatggtatc agagcgggac gatccttgct cttcacttcc gcacaaaatt ttcgttcaat    3840
tcaacccatc aaattttttt tttcccccaa attttctcga attcggtcaa aattcgacga    3900
attagggatt caatttaccc tgatttcttc tgattccatt caatgattgt tcatttcgaa    3960
tcttgaatca aataattgtt gattctggat tccccaaatt ctagggttct tgaaggattt    4020
acaagaatct ggcattgctg atagattctt gaagcaattt gcgtctccgt gttcctcggt    4080
ggtcttgagt ttgtttccgt attcgctgct ctcatcttta ctggggattg tggtctgatt    4140
tcttggcttc ctctgtcgat gatgtgattg gtaatactta aaaccctct ctctcttcc      4200
```

```
gaaattattg atgctggttc gtcatttttt tttttggaat catctcagtt tatcgccgca    4260
atttgagttg ttgttgggta attgttgttg ctgccgatga tgttttgtga atttgagaat    4320
tgttagaatg attcttgttc aatcaatttg gttctcatac tctaatggaa gcctgttttg    4380
gagcgacgaa ttatgcaatt ctgagatttc ttttgatcct tatttctttt cttcacttga    4440
atttctggtg tttgtgagta attcttggtt aatgtttgat ctgggtagtt cttgggttta    4500
ctgaagacgt ttccttgaagg ttttgacaga aaagctgagg tttaattcca aaattcttct    4560
gtccaattac attttttattg ttgatggttc ttatgtgaga actagactga gtttttttta    4620
tgaaattgtt tcgaccttca gatggattcg agagatttga gttcattttc tttgatgaat    4680
gtgttagaaa aggttttggt gcagtgacca ttttaaacca aatagagtta cataaatatt    4740
gggattcttt tctgggaatg tagttaggag ttgaaatctt ttggagctgc tttaccataa    4800
aacccagcct cagagtctgt taaccagtta ggaccgtgta acatgatcc caggctgcat    4860 ttgcgttatc agatttgatt cagttttgga attgtggatt ttgagggttt aaaagcttac    4920
agttgctcct ggagaatggt gtgagcaata taggaattca gcactagtat tgcagaaaat    4980
gaagcttggt tgttgattgt tggcatgttt tgttgccatt gttttgggtt gatgttttcc    5040
tttctttttg aatgttggca cgattcaaca tttctttcct gcaacagatt tggagttcag    5100
tacctgtata atcaggtcaa ttttgttcat tttccccagc aacagatctg gagaatcaga    5160
acctgtaaaa nnnnnnnnnn nnnnnnnnnn nnnnnnnnnn nnnnnnnnnn nnnnnnnnnn    5220
nnnnnnnnnn acccaaagag gtcagttttc attgatccat tgtgatcatt cttttgatga    5280
gacccattga ggctcatttc ttcaaggcaa tattggaagt tgtagattga tatgagcagt    5340
tggtacaaca gcaacaaaag tggccagcat ctatgcttgt tcatgaggag ttcttggtgc    5400
agagttaatg aagagtctgt tttgaagctt tcaaactgaa gatgtttatc accatctcca    5460
gtttgagggg gggtattgga gtatagaaca tcaggttata actagcttgt aactaacttg    5520
taactaccta gtataaatac agtagtttgt acnnnnnnnn nnnnnnnnnn nnnnnnnnnn    5580
nnnnnnnnnn nnnnnnnnnn nnccacgagc tccaagctcg tcaatggctt cccttctctg    5640
ttcttgcttt cttctttcct cttcaattca caaattcaac atccccaaaa ttgtaagtca    5700
ttgcagaaag taatttattc atttatattt attttatgct tagaatgata tacgcagtcg    5760
tcctttggtt tcaaatcttg aatttggttt ttgttttctt tctttgtttc tttattcaac    5820
accagcccat ttatgattga ttcattaaaa aaaggatgga gttttatgga tttgaagaag    5880
acaacgaatt gagattcctg ggttttctt tttgttgggg ttggatttca tgtatatgtt    5940
gctgattaaa tacgagactg atgatgatga tgtgtttatg ggttttaaat cagattaaat    6000
atatgggaaa tgcaagttaa tttgggatgc acataaggtg tttgctgaaa tgtctatgag    6060
aaatgttgtt tcttggactt agaatgatat acactgtcgt cctttggttt ccaatcttac    6120
atttggtttg tgttttctta gtttgttct ttaatcaaca ccaacccgtt ttttttaaac    6180
tacctgcaac tactaattta cgtttaccct gtatctcagg tactaaatga atattggtga    6240
ttttcagtta ctcaacacta gcttgatcct gaacgcaccc aaccttcagg ttagaatccg    6300
gcttactcat ccttttgtcc agttttcaag taattgtttt ggcaggatca attctctaat    6360
tgttgtacac cgtatattgc aatttatagt gactacagtt aatgaatgtt tacaaaaaat    6420
tagtcatgta aaaacttctt ctctgtccat tacataaact cttttctct ttctaactta    6480 tcatgttcat gtctaaacaa ttaaacatgc tcacatcaat gttcatttaa gctaacttac    6540
ttctgtaaga gagcgagcta gttaaaaact cctttaactt tctgttttat actcaggaca    6600
```

```
tggattgatg caagcatgaa gaacttcggg aatttgctaa aactctacca aagcgatgag    6660
agtttggact ttatttcact tgaagtcagg gactgtcaac aaagccacag tgtgcatgtt    6720
ggctgtttca cttggacgat aaaaaggttt atttaattgt tttcctaagt gtatttggct    6780
tacaagcttt tacttttcac ttgaaagggt ttttcttgtt ttaagctttt cgaattagag    6840
ttttcggttg aagtaagagt agtcgtatta gtcttttacc taaggaagac tcttttttgt    6900
aattttcaga ctatgcaatt caagttttcg agtgttttct tgcttgtgtg attgtgagtt    6960
ggtgaattcg tctttcatac attttgagat tatcagaagc tttatgctcc accggtagtc    7020
tagtaccttt tctgttactg tgcagggaag taatctggta ccttctatat atatggaaaa    7080
acatacatta tacattatgc aaaattctta caggttagtt acttcctgga acttcattta    7140
cacttagttt tttttgttcc attccctcgg aatcaagtca ttccctctga gaaatatgta    7200
atgaacttct gtatgttgct gtttggttcc tgttttaatc ttcaattttc ttgtatagtt    7260
acagctgcat ttacaatgaa gtttaagcag acactctctt tatatagtgc ctctttctgg    7320
agcaccgtag agctgtctgt ggttgatcac catctgctgc cgagagattc agcaatcgcg    7380
tgtttgatca ggtaaaagtt tttatgtcaa tgtgttttt tttccgtttg atcaattat    7440 gtctgtattc agattcttat cttcttacag tagcataaca cattgtttct ttcatttatg    7500
taaactgttt caagattaca gagatgtatg cttcagtcga cattgatgat aacttaagat    7560
ggcattccta caacagttgc aggcgcattc taactccggc aattctagtt aggcaagagg    7620
agcattgcca atacctgcca cctctgggat ttactatacc agggttgaag tttatggaag    7680
acaccagcta tgcacaagcc ttcaagggg tcatcctacat aacaagttga accaaccaat    7740
tgcttgttgg ttcagtggta attgaagctg aatttggtag ggatggcccg tgttcgatcc    7800
ccacaacaac aattgggagg ggactggaac ctatccacac agaactcgcc ctgaatccgg    7860
attagcccta agggtgaacg gggtgctaac accaaaaaaa aaaacataac aagttgaacc    7920
aaacatactt tgtttgaatt gaagatttag tgatttcatt tgatcgattg agatgtctta    7980
ttataagcgt atatgctctt ggatttggcc acttaggtgt tgtttgacaa ttggacatta    8040
actcgctttt atattttctt ttctcttagg aaaggtgatc ctgagaattt atattggaac    8100 acttttttt tctcactagc tttaaaaaag tgttctgtgt tacctgcaat tcaatttgat    8160
tatttttcac atagttttac ctgaaaaagt gttacctgaa aaagtgttac ctgaaaatca    8220
actgacataa gttttgttt ggatccaatt aaggacacta gataaatcgg aataaataat    8280
caaccaatta agtacttcat aattaaatat gaagtgtatt attatcttat gcttgtgaca    8340
ttgaaggatg ttatgatatt ttaactcaat accttgcaaa atatactgg              8389
```

<210> SEQ ID NO 2
<211> LENGTH: 3606
<212> TYPE: DNA
<213> ORGANISM: Spinacia oleracea

<400> SEQUENCE: 2

```
atggccgaaa tcggatactc ggtttgtgcg aaactcatcg aagtgattgg cagtgagctg      60
atcaaagaga tttgtgacac atggggttac aaatctcttc ttgaggacct caacaaaact     120
gtattgacgg tcaggaacgt tctcattcaa gccggggtga tgcgggagct tactagtgaa     180
caacaaggtt tcattgcaga ccttaaagat gttgtttatg atgctgatga cttgttcgac     240
aagttactca ctcgtgctga gcgaaaacag attgatggaa acgaaatctc tgaaaaggta     300
```

```
cgtcgtttct tttcctctag taacaagatc ggtcaagctt actacatgtc tcgtaaggtt      360
aaggaaatta agaagcagtt ggatgaaatt gttgataggc atacaaaatt tgggtttagt      420
gccgagttta tacctgtttg tagggaaagg gggaacgaga gggaaacacg ttcatatata      480
gatgtcaaga atattcttgg gagggataaa gataagaatg atatcataga taggttgctt      540
aatcgtaatg gtaatgaagc ttgtagtttc ctgaccatag tgggagcggg aggattggga      600
aaaactgctc ttgcacaact tgtgttcaat gatgaaaggg tcaaaattga gttccatgat      660
ttgaggtatt gggtttgtgt ctctgatcaa gatggggggcc aatttgatgt gaaagaaatc      720
ctttgtaaga ttttagaggt ggttactaag gagaaagttg ataatagttc cacattggaa      780
ttggtacaaa gccaatttca agagaagtta agaggaaaga agtacttcct tgttcttgat      840
gatgtatgga acgaagatcg tgagaagtgg cttccttttgg aagagttgtt aatgttgggt      900
caagggggaa gcaaggttgt agtgaccgca cgttcagaga agacagcaaa tgtcataggg      960
aaaagacatt tttatacact ggaatgtttg tcaccagatt attcatggag cttatttgaa     1020
atgtcggctt ttcagaaagg gcatgagcag gaaaaccatc acgaactagt tgatattggg     1080
aaaaagattg ttgaaaaatg ttataacaat ccacttgcta taacggtggt aggaagtctt     1140
ctttatggag aggagataag taagtggcgg tcatttgaaa tgagtgagtt ggccaaaatt     1200
ggcaatgggg ataataagat tttgccgata ttaaagctca gttaccataa tcttataccc     1260
tcgttgaaga gttgcttcag ttattgtgca gtgtttccca aggatcatga aataagaag      1320
gagatgttga ttgatctttg gatagcacaa ggatacgttg tggcacttga tggaggtcaa     1380
agtatagaag atgctgccga agaacatttt gtaattttgt tacggagatg tttcttttcaa    1440
gatgtaaaga aggatgaata tggtgatgtt gattctgtta aaatccacga cttgatgcac     1500
gatgtcgccc aagaagtggg gagggaggaa atatgtgtag tgaatgataa tacaaagaac     1560
ttgggtgata aaatccgtca tgtacatggt gatgtcaata gatatgcaca aagagtctct     1620
ctgtgtagcc atagccataa gattcgttcg tatattggtg gtgattgtga aaaacgttgt     1680
gtggatacac taatagacaa gtggatgtgt cttaggatgt tggacttgtc atggtcggat     1740
gttaaaaatt tgcctaattc aataggtaaa ttgttgcact tgaggtatct taacctgtca     1800
gataatagaa atctaaagat acttcctgat gcaattacaa gactgcataa tttgcagaca     1860
ctgcttttaa aagattgcag aagtttaaag gagttgccaa aagattttttg caaattggtc     1920
aaactgagac acttggatttt atggggttgt gatgatttga ttggtatgcc atttggaatg     1980
gataagctaa ctagtcttag aatactacca aacattgtgg tgggtaggaa ggaacaaagt     2040
gttgatgatg agctgaaagc ccttaaaggc ctcaccgaga taaaaggcga cattgatatc     2100
aaaatctgtg aaaattatag aatagttgaa ggcatgaatg acacaggagg agctgggtat     2160
ttgaagagca tgaaacatct cagggagatt ggtattacat ttgatggtgg atgtgttaac     2220
cctgaagctg tgttggcaac cctagagcca ccttcaaata tcaagagctt atctatacat     2280
cgttttgatg gtaaaacact tccagtatgg ggaagagcag agattaattg ggcaatctcc     2340
ctctcacatc ttgtcgacat ccagctttgg cattgtcgta atttgcagga gatgccagtg     2400
ctgagtaaac tgcctcattt gaaatcactg gaactttata atttgattag tttagagtac     2460
atggagagca caagcagaag cagtagcagt gacacagaag cagcaacacc agaattacca     2520
acattcttcc cttcccttga aaacttaca ctttggggtc tggaaaagtt gaagggtttg      2580
gggaacagga gatcgagtag ttttcccgc ctctctgaat tgaaaatcat ggaatgccca      2640
gatctaacgt ggtttcctcc ctgtccaagc cttgaaaaac ttacactttg gcgtctggac     2700
```

-continued

```
aagttgaagg gttttgggaa ccggagatcg agtactttc cccgcctctc tgaattggaa    2760
atcaagaaat gcccagatct aacgtcattt ccttcttgtc caagccttga gaagttggaa   2820
ttgaaagaaa gcaatgaagc attgcaaata atagtaaaaa taacaacaag aggtaaagaa   2880
aaagaagaga acaataatgc tggtgttaga aattcacaag atgatgacaa agtcaaatta   2940
cggaagatgg tgatagacaa tctgggttat ctcaaatcac tgcccacaaa ttgtcttact   3000
cacctcgacc ttacaataag tgattccaag gaggggagg gtgaatggga agttggggat    3060
gcatttcaga agtgtgtatc ttcttggaga agcctcacca taatcggaaa tcacggaata   3120
aataaagtga agagactgtc tggaagaaca gggttggagc atttcactct gttggaatca   3180
ctcaaacttt cagatataga agaccaggaa gatgagggcg aagacaacat catattctgg   3240
aaatcctttc ctcaaaacct ccgcagtttg agaattaaag actctgacaa aatgacaagt   3300
ttgcccatgg ggatgcagta cttaacctcc ctccaaaccc tctatctaca ccattgttat   3360
gaattgaatt cccttccaga atggataagc agcttatcat ctcttcaata cctgcgcata   3420
tactactgtc cagccctgaa atcactacca gaagcaatgc ggaacctcac ctcccttcag   3480
acacttggga tatcggattg tccagaccta gttaaaagat gcagaaaacc caacggcaag   3540
gactatccca aaattcaaca catcccctat tggagtatag aacatcaggt tataactagc   3600
ttgtaa                                                              3606
```

<210> SEQ ID NO 3
<211> LENGTH: 3609
<212> TYPE: DNA
<213> ORGANISM: Spinacia oleracea

<400> SEQUENCE: 3

```
atggccgaaa tcggatactc ggtttgtgcg aaactcatcg aagtgattgg cagtgagctg     60
atcaaagaga tttgtgacac atggggttac aaatctcttc ttgaggacct caacaaaact    120
gtattgacgg tcaggaacgt tctcattcaa gccggggtga tgcgggagct tactagtgaa    180
caacaaggtt tcattgcaga ccttaaagat gttgtttatg atgctgatga cttgttcgac    240
aagttactca ctcgtgctga gcgaaaacag attgatggaa acgaaatctc tgaaaaggta    300 cgtcgttttct tttcctctag taacaagatc ggtcaagctt actacatgtc tcgtaaggtt    360
aaggaaatta agaagcagtt ggatgaaatt gttgataggc atacaaaatt tgggtttagt    420
gccgagttta tacctgtttg tagggaaagg gggaacgaga gggaaacacg ttcatatata    480
gatgtcaaga atattcttgg gagggataaa gataagaatg atatcataga taggttgctt    540
aatcgtaatg gtaatgaagc ttgtagtttc ctgaccatag tgggagcggg aggattggga    600
aaaactgctc ttgcacaact tgtgttcaat gatgaaaggg tcaaaattga gttccatgat    660
ttgaggtatt gggtttgtgt ctctgatcaa gatggggggcc aatttgatgt gaaagaaatc    720
ctttgtaaga ttttagaggt ggttactaag gagaaagttg ataatagttc cacattggaa    780
ttggtacaaa gccaatttca agagaagtta gaggaaaga agtacttcct tgttcttgat    840
gatgtatgga cgaagatcg tgagaagtgg cttcctttgg aagagttgtt aatgttgggt    900 caaggggaa gcaaggttgt agtgaccgca cgttcagaga agacagcaaa tgtcataggg    960
aaaagacatt tttatacact ggaatgtttg tcaccagatt attcatggag cttatttgaa   1020
atgtcggctt tcagaaagg gcatgagcag gaaaaccatc acgaactagt tgatattggg   1080 aaaagattg ttgaaaaatg ttataacaat ccacttgcta taacggtggt aggaagtctt   1140
```

```
ctttatggag aggagataag taagtggcgg tcatttgaaa tgagtgagtt ggccaaaatt     1200
ggcaatgggg ataataagat tttgccgata ttaaagctca gttaccataa tcttataccc     1260
tcgttgaaga gttgcttcag ttattgtgca gtgtttccca aggatcatga aataaagaag     1320
gagatgttga ttgatctttg gatagcacaa ggatacgttg tggcacttga tggaggtcaa     1380
agtatagaag atgctgccga agaacatttt gtaattttgt tacggagatg tttctttcaa     1440
gatgtaaaga aggatgaata tggtgatgtt gattctgtta aaatccacga cttgatgcac     1500
gatgtcgccc aagaagtggg gagggaggaa atatgtgtag tgaatgataa tacaaagaac     1560
ttgggtgata aaatccgtca tgtacatggt gatgtcaata gatatgcaca aagagtctct     1620
ctgtgtagcc atagccataa gattcgttcg tatattggtg gtgattgtga aaaacgttgt     1680
gtggatacac taatagacaa gtggatgtgt cttaggatgt tggacttgtc atggtcggat     1740
gttaaaaatt tgcctaattc aataggtaaa ttgttgcact tgaggtatct taacctgtca     1800
gataatagaa atctaaagat acttcctgat gcaattacaa gactgcataa tttgcagaca     1860
ctgcttttaa aagattgcag aagtttaaag gagttgccaa aagattttg caaattggtc      1920 aaactgagac acttggattt atggggttgt gatgatttga ttggtatgcc atttggaatg     1980
gataagctaa ctagtcttag aatactacca aacattgtgg tgggtaggaa ggaacaaagt     2040
gttgatgatg agctgaaagc ccttaaaggc ctcaccgaga taaaaggcga cattgatatc     2100
aaaatctgtg aaaattatag aatagttgaa ggcatgaatg acacaggagg agctgggtat     2160
ttgaagagca tgaaacatct cagggagatt ggtattacat ttgatggtgg atgtgttaac     2220
cctgaagctg tgttggcaac cctagagcca ccttcaaata tcaagagctt atctatacat     2280
cgttttgatg gtaaaacact tccagtatgg ggaagagcag agattaattg gcaatctcc     2340 ctctcacatc ttgtcgacat ccagctttgg cattgtcgta atttgcagga gatgccagtg     2400
ctgagtaaac tgcctcattt gaaatcactg gaactttata atttgattag tttagagtac     2460
atggagagca caagcagaag cagtagcagt gacacagaag cagcaacacc agaattacca     2520
acattcttcc cttcccttga aaaacttaca ctttggggtc tggaaaagtt gaagggtttg     2580
gggaacagga gatcgagtag ttttccccgc ctctctgaat tgaaaatcat ggaatgccca     2640
gatctaacgt ggtttcctcc ctgtccaagc cttgaaaaac ttacactttg gcgtctggac     2700
aagttgaagg gttttgggaa ccggagatcg agtactttc cccgcctctc tgaattggaa      2760
atcaagaaat gcccagatct aacgtcattt ccttcttgtc caagccttga gaagttggaa     2820
ttgaaagaaa gcaatgaagc attgcaaata atagtaaaaa taacaacaag aggtaaagaa     2880
aaagaagaga acaataatgc tggtgttaga aattcacaag atgatgacaa agtcaaatta     2940
cggaagatgg tgatagacaa tctgggttat ctcaaatcac tgcccacaaa ttgtcttact     3000 caccctcgacc ttacaataag tgattccaag gaggggagg gtgaatggga agttggggat     3060
gcatttcaga agtgtgtatc ttctttgaga agcctcacca taatcggaaa tcacggaata     3120
aataaagtga agagactgtc tggaagaaca gggttggagc atttcactct gttggaatca     3180
ctcaaacttt cagatataga agaccaggaa gatgagggcg aagacaacat catattctgg     3240
aaatcctttc ctcaaaacct ccgcagtttg agaattaaag actctgacaa aatgacaagt     3300
ttgcccatgg ggatgcagta cttaacctcc ctccaaaccc tctatctaca ccattgttat     3360
gaattgaatt cccttccaga atggataagc agcttatcat ctcttcaata cctgcgcata     3420
tactactgtc cagccctgaa atcactacca gaagcaatgc ggaaccctcac ctcccttcag     3480 acacttggga tatcggattg tccagaccta gttaaaagat gcagaaaacc caacggcaag     3540
```

```
gactatccca aaattcaaca catcccctat tggagtatag aacatcaggt actaaatgaa    3600
tattggtga                                                            3609

<210> SEQ ID NO 4
<211> LENGTH: 2445
<212> TYPE: DNA
<213> ORGANISM: Spinacia oleracea

<400> SEQUENCE: 4
atggccgaaa tcggatactc ggtttgtgcg aaactcatcg aagtgattgg cagtgagctg      60
atcaaagaga tttgtgacac atgggggttac aaatctcttc ttgaggacct caacaaaact   120
gtattgacgg tcaggaacgt tctcattcaa gccggggtga tgcgggagct tactagtgaa   180
caacaaggtt tcattgcaga ccttaaagat gttgtttatg atgctgatga cttgttcgac   240
aagttactca ctcgtgctga gcgaaaacag attgatggaa cgaaatctc tgaaaaggta   300 cgtcgtttct tttcctctag taacaagatc ggtcaagctt actacatgtc tcgtaaggtt   360
aaggaaatta agaagcagtt ggatgaaatt gttgataggc atacaaaatt tgggtttagt   420
gccgagttta tacctgtttg tagggaaagg gggaacgaga gggaaacacg ttcatatata   480
gatgtcaaga atattcttgg gagggataaa gataagaatg atatcataga taggttgctt   540
aatcgtaatg gtaatgaagc ttgtagtttc ctgaccatag tgggagcggg aggattggga   600
aaaactgctc ttgcacaact tgtgttcaat gatgaaaggg tcaaaattga gttccatgat   660
ttgaggtatt gggtttgtgt ctctgatcaa gatgggggcc aatttgatgt gaaagaaatc   720
ctttgtaaga ttttagaggt ggttactaag gagaaagttg ataatagttc cacattggaa   780
ttggtacaaa gccaatttca agagaagtta agaggaaaga agtacttcct tgttcttgat   840
gatgtatgga cgaagatcg tgagaagtgg cttcctttgg aagagttgtt aatgttgggt   900 caaggggaa gcaaggttgt agtgaccgca cgttcagaga agacagcaaa tgtcataggg   960
aaaagacatt tttatacact ggaatgtttg tcaccagatt attcatggag cttatttgaa  1020
atgtcggctt tcagaaagg gcatgagcag gaaaaccatc acgaactagt tgatattggg  1080
aaaaagattg ttgaaaaatg ttataacaat ccacttgcta acggtggt aggaagtctt   1140 ctttatggag aggagataag taagtggcgg tcatttgaaa tgagtgagtt ggccaaaatt  1200
ggcaatgggg ataataagat tttgccgata ttaaagctca gttaccataa tcttataccc  1260
tcgttgaaga gttgcttcag ttattgtgca gtgtttccca aggatcatga ataaagaag   1320 gagatgttga ttgatctttg gatagcacaa ggatacgttg tggcacttga tggaggtcaa  1380
agtatagaag atgctgccga agaacatttt gtaattttgt tacggagatg ttctcttcaa  1440
gatgtaaaga aggatgaata tggtgatgtt gattctgtta aaatccacga cttgatgcac  1500
gatgtcgccc aagaagtggg gagggaggaa atatgtgtag tgaatgataa tacaaagaac  1560
ttgggtgata aaatccgtca tgtacatggt gatgtcaata gatatgcaca agagtctct    1620 ctgtgtagcc atagccataa gattcgttcg tatattggtg gtgattgtga aaacgttgt   1680 gtggatacac taatagacaa gtggatgtgt cttaggatgt tggacttgtc atggtcggat  1740
gttaaaaatt tgcctaattc aataggtaaa ttgttgcact tgaggtatct taacctgtca  1800
gataatagaa atctaaagat acttcctgat gcaattacaa gactgcataa tttgcagaca  1860
ctgcttttaa aagattgcag aagtttaaag gagttgccaa agattttttg caaattggtc  1920
aaactgagac acttggattt atggggttgt gatgatttga ttggtatgcc atttggaatg  1980
```

```
gataagctaa ctagtcttag aatactacca aacattgtgg tgggtaggaa ggaacaaagt    2040
gttgatgatg agctgaaagc ccttaaaggc ctcaccgaga taaaaggcga cattgatatc    2100
aaaatctgtg aaaattatag aatagttgaa ggcatgaatg acacaggagg agctgggtat    2160
ttgaagagca tgaaacatct cagggagatt ggtattacat ttgatggtgg atgtgttaac    2220
cctgaagctg tgttggcaac cctagagcca ccttcaaata tcaagagctt atctatacat    2280
cgttttgatg gtaaaacact tccagtatgg ggaagagcag agattaattg gcaatctcc    2340 ctctcacatc ttgtcgacat ccagctttgg cattgtcgta atttgcagga gatgccagtg    2400
ctgagtaaac tgcctcattt gaaatcactg gaactttata atttg                    2445
```

<210> SEQ ID NO 5
<211> LENGTH: 1201
<212> TYPE: PRT
<213> ORGANISM: Spinacia oleracea

<400> SEQUENCE: 5

```
Met Ala Glu Ile Gly Tyr Ser Val Cys Ala Lys Leu Ile Glu Val Ile
1               5                   10                  15

Gly Ser Glu Leu Ile Lys Glu Ile Cys Asp Thr Trp Gly Tyr Lys Ser
            20                  25                  30

Leu Leu Glu Asp Leu Asn Lys Thr Val Leu Thr Val Arg Asn Val Leu
        35                  40                  45

Ile Gln Ala Gly Val Met Arg Glu Leu Thr Ser Gln Gln Gly Phe
    50                  55                  60

Ile Ala Asp Leu Lys Asp Val Val Tyr Asp Ala Asp Asp Leu Phe Asp
65                  70                  75                  80

Lys Leu Leu Thr Arg Ala Glu Arg Lys Gln Ile Asp Gly Asn Glu Ile
                85                  90                  95

Ser Glu Lys Val Arg Arg Phe Phe Ser Ser Asn Lys Ile Gly Gln
            100                 105                 110

Ala Tyr Tyr Met Ser Arg Lys Val Lys Glu Ile Lys Lys Gln Leu Asp
        115                 120                 125

Glu Ile Val Asp Arg His Thr Lys Phe Gly Phe Ser Ala Glu Phe Ile
    130                 135                 140

Pro Val Cys Arg Glu Arg Gly Asn Glu Arg Glu Thr Arg Ser Tyr Ile
145                 150                 155                 160

Asp Val Lys Asn Ile Leu Gly Arg Asp Lys Asp Asn Asp Ile Ile
                165                 170                 175

Asp Arg Leu Leu Asn Arg Asn Gly Asn Glu Ala Cys Ser Phe Leu Thr
            180                 185                 190

Ile Val Gly Ala Gly Gly Leu Gly Lys Thr Ala Leu Ala Gln Leu Val
        195                 200                 205

Phe Asn Asp Glu Arg Val Lys Ile Glu Phe His Asp Leu Arg Tyr Trp
    210                 215                 220

Val Cys Val Ser Asp Gln Asp Gly Gly Gln Phe Asp Val Lys Glu Ile
225                 230                 235                 240

Leu Cys Lys Ile Leu Glu Val Val Thr Lys Glu Lys Val Asp Asn Ser
                245                 250                 255

Ser Thr Leu Glu Leu Val Gln Ser Gln Phe Gln Glu Lys Leu Arg Gly
            260                 265                 270

Lys Lys Tyr Phe Leu Val Leu Asp Asp Val Trp Asn Glu Asp Arg Glu
        275                 280                 285

Lys Trp Leu Pro Leu Glu Glu Leu Leu Met Leu Gly Gln Gly Gly Ser
```

```
              290                 295                 300
Lys Val Val Thr Ala Arg Ser Glu Lys Thr Ala Asn Val Ile Gly
305                 310                 315                 320

Lys Arg His Phe Tyr Thr Leu Glu Cys Leu Ser Pro Asp Tyr Ser Trp
                    325                 330                 335

Ser Leu Phe Glu Met Ser Ala Phe Gln Lys Gly His Glu Gln Glu Asn
                340                 345                 350

His His Glu Leu Val Asp Ile Gly Lys Lys Ile Val Glu Lys Cys Tyr
            355                 360                 365

Asn Asn Pro Leu Ala Ile Thr Val Val Gly Ser Leu Leu Tyr Gly Glu
        370                 375                 380

Glu Ile Ser Lys Trp Arg Ser Phe Glu Met Ser Glu Leu Ala Lys Ile
385                 390                 395                 400

Gly Asn Gly Asp Asn Lys Ile Leu Pro Ile Leu Lys Leu Ser Tyr His
                    405                 410                 415

Asn Leu Ile Pro Ser Leu Lys Ser Cys Phe Ser Tyr Cys Ala Val Phe
                420                 425                 430

Pro Lys Asp His Glu Ile Lys Lys Glu Met Leu Ile Asp Leu Trp Ile
            435                 440                 445

Ala Gln Gly Tyr Val Val Ala Leu Asp Gly Gly Gln Ser Ile Glu Asp
        450                 455                 460

Ala Ala Glu Glu His Phe Val Ile Leu Arg Arg Cys Phe Gln
465                 470                 475                 480

Asp Val Lys Lys Asp Glu Tyr Gly Asp Val Asp Ser Val Lys Ile His
                    485                 490                 495

Asp Leu Met His Asp Val Ala Gln Glu Val Gly Arg Glu Glu Ile Cys
                500                 505                 510

Val Val Asn Asp Asn Thr Lys Asn Leu Gly Asp Lys Ile Arg His Val
            515                 520                 525

His Gly Asp Val Asn Arg Tyr Ala Gln Arg Val Ser Leu Cys Ser His
        530                 535                 540

Ser His Lys Ile Arg Ser Tyr Ile Gly Gly Asp Cys Glu Lys Arg Cys
545                 550                 555                 560

Val Asp Thr Leu Ile Asp Lys Trp Met Cys Leu Arg Met Leu Asp Leu
                    565                 570                 575

Ser Trp Ser Asp Val Lys Asn Leu Pro Asn Ser Ile Gly Lys Leu Leu
                580                 585                 590

His Leu Arg Tyr Leu Asn Leu Ser Asp Asn Arg Asn Leu Lys Ile Leu
            595                 600                 605

Pro Asp Ala Ile Thr Arg Leu His Asn Leu Gln Thr Leu Leu Leu Lys
        610                 615                 620

Asp Cys Arg Ser Leu Lys Glu Leu Pro Lys Asp Phe Cys Lys Leu Val
625                 630                 635                 640

Lys Leu Arg His Leu Asp Leu Trp Gly Cys Asp Asp Leu Ile Gly Met
                    645                 650                 655

Pro Phe Gly Met Asp Lys Leu Thr Ser Leu Arg Ile Leu Pro Asn Ile
                660                 665                 670

Val Val Gly Arg Lys Glu Gln Ser Val Asp Asp Glu Leu Lys Ala Leu
            675                 680                 685

Lys Gly Leu Thr Glu Ile Lys Gly Asp Ile Asp Ile Lys Ile Cys Glu
        690                 695                 700

Asn Tyr Arg Ile Val Glu Gly Met Asn Asp Thr Gly Gly Ala Gly Tyr
705                 710                 715                 720
```

-continued

```
Leu Lys Ser Met Lys His Leu Arg Glu Ile Gly Ile Thr Phe Asp Gly
            725                 730                 735

Gly Cys Val Asn Pro Glu Ala Val Leu Ala Thr Leu Glu Pro Pro Ser
            740                 745                 750

Asn Ile Lys Ser Leu Ser Ile His Arg Phe Asp Gly Lys Thr Leu Pro
            755                 760                 765

Val Trp Gly Arg Ala Glu Ile Asn Trp Ala Ile Ser Leu Ser His Leu
770                 775                 780

Val Asp Ile Gln Leu Trp His Cys Arg Asn Leu Gln Glu Met Pro Val
785                 790                 795                 800

Leu Ser Lys Leu Pro His Leu Lys Ser Leu Glu Leu Tyr Asn Leu Ile
            805                 810                 815

Ser Leu Glu Tyr Met Glu Ser Thr Ser Arg Ser Ser Ser Ser Asp Thr
            820                 825                 830

Glu Ala Ala Thr Pro Glu Leu Pro Thr Phe Phe Pro Ser Leu Glu Lys
            835                 840                 845

Leu Thr Leu Trp Gly Leu Glu Lys Leu Lys Gly Leu Gly Asn Arg Arg
            850                 855                 860

Ser Ser Ser Phe Pro Arg Leu Ser Glu Leu Lys Ile Met Glu Cys Pro
865                 870                 875                 880

Asp Leu Thr Trp Phe Pro Pro Cys Pro Ser Leu Glu Lys Leu Thr Leu
            885                 890                 895

Trp Arg Leu Asp Lys Leu Lys Gly Phe Gly Asn Arg Arg Ser Ser Thr
            900                 905                 910

Phe Pro Arg Leu Ser Glu Leu Glu Ile Lys Lys Cys Pro Asp Leu Thr
            915                 920                 925

Ser Phe Pro Ser Cys Pro Ser Leu Glu Lys Leu Glu Leu Lys Glu Ser
            930                 935                 940

Asn Glu Ala Leu Gln Ile Ile Val Lys Ile Thr Thr Arg Gly Lys Glu
945                 950                 955                 960

Lys Glu Glu Asn Asn Asn Ala Gly Val Arg Asn Ser Gln Asp Asp Asp
            965                 970                 975

Lys Val Lys Leu Arg Lys Met Val Ile Asp Asn Leu Gly Tyr Leu Lys
            980                 985                 990

Ser Leu Pro Thr Asn Cys Leu Thr His Leu Asp Leu Thr Ile Ser Asp
            995                 1000                1005

Ser Lys Glu Gly Glu Gly Glu Trp Glu Val Gly Asp Ala Phe Gln Lys
    1010                1015                1020

Cys Val Ser Ser Leu Arg Ser Leu Thr Ile Ile Gly Asn His Gly Ile
1025                1030                1035                1040

Asn Lys Val Lys Arg Leu Ser Gly Arg Thr Gly Leu Glu His Phe Thr
                1045                1050                1055

Leu Leu Glu Ser Leu Lys Leu Ser Asp Ile Glu Asp Gln Glu Asp Glu
                1060                1065                1070

Gly Glu Asp Asn Ile Ile Phe Trp Lys Ser Phe Pro Gln Asn Leu Arg
            1075                1080                1085

Ser Leu Arg Ile Lys Asp Ser Asp Lys Met Thr Ser Leu Pro Met Gly
            1090                1095                1100

Met Gln Tyr Leu Thr Ser Leu Gln Thr Leu Tyr Leu His His Cys Tyr
1105                1110                1115                1120

Glu Leu Asn Ser Leu Pro Glu Trp Ile Ser Ser Leu Ser Leu Gln
                1125                1130                1135
```

```
Tyr Leu Arg Ile Tyr Tyr Cys Pro Ala Leu Lys Ser Leu Pro Glu Ala
            1140                1145                1150

Met Arg Asn Leu Thr Ser Leu Gln Thr Leu Gly Ile Ser Asp Cys Pro
        1155                1160                1165

Asp Leu Val Lys Arg Cys Arg Lys Pro Asn Gly Lys Asp Tyr Pro Lys
    1170                1175                1180

Ile Gln His Ile Pro Tyr Trp Ser Ile Glu His Gln Val Ile Thr Ser
1185                1190                1195                1200

Leu

<210> SEQ ID NO 6
<211> LENGTH: 1202
<212> TYPE: PRT
<213> ORGANISM: Spinacia oleracea

<400> SEQUENCE: 6

Met Ala Glu Ile Gly Tyr Ser Val Cys Ala Lys Leu Ile Glu Val Ile
1               5                   10                  15

Gly Ser Glu Leu Ile Lys Glu Ile Cys Asp Thr Trp Gly Tyr Lys Ser
            20                  25                  30

Leu Leu Glu Asp Leu Asn Lys Thr Val Leu Thr Val Arg Asn Val Leu
        35                  40                  45

Ile Gln Ala Gly Val Met Arg Glu Leu Thr Ser Glu Gln Gln Gly Phe
    50                  55                  60

Ile Ala Asp Leu Lys Asp Val Val Tyr Asp Ala Asp Leu Phe Asp
65                  70                  75                  80

Lys Leu Leu Thr Arg Ala Glu Arg Lys Gln Ile Asp Gly Asn Glu Ile
                85                  90                  95

Ser Glu Lys Val Arg Arg Phe Phe Ser Ser Asn Lys Ile Gly Gln
            100                 105                 110

Ala Tyr Tyr Met Ser Arg Lys Val Lys Glu Ile Lys Lys Gln Leu Asp
        115                 120                 125

Glu Ile Val Asp Arg His Thr Lys Phe Gly Phe Ser Ala Glu Phe Ile
    130                 135                 140

Pro Val Cys Arg Glu Arg Gly Asn Glu Arg Glu Thr Arg Ser Tyr Ile
145                 150                 155                 160

Asp Val Lys Asn Ile Leu Gly Arg Asp Lys Asp Lys Asn Asp Ile Ile
                165                 170                 175

Asp Arg Leu Leu Asn Arg Asn Gly Asn Glu Ala Cys Ser Phe Leu Thr
            180                 185                 190

Ile Val Gly Ala Gly Gly Leu Gly Lys Thr Ala Leu Ala Gln Leu Val
        195                 200                 205

Phe Asn Asp Glu Arg Val Lys Ile Glu Phe His Asp Leu Arg Tyr Trp
    210                 215                 220

Val Cys Val Ser Asp Gln Asp Gly Gly Gln Phe Asp Val Lys Glu Ile
225                 230                 235                 240

Leu Cys Lys Ile Leu Glu Val Val Thr Lys Glu Lys Val Asp Asn Ser
                245                 250                 255

Ser Thr Leu Glu Leu Val Gln Ser Gln Phe Gln Glu Lys Leu Arg Gly
            260                 265                 270

Lys Lys Tyr Phe Leu Val Leu Asp Asp Val Trp Asn Glu Asp Arg Glu
        275                 280                 285

Lys Trp Leu Pro Leu Glu Glu Leu Leu Met Leu Gly Gln Gly Gly Ser
    290                 295                 300
```

-continued

```
Lys Val Val Thr Ala Arg Ser Glu Lys Thr Ala Asn Val Ile Gly
305                 310                 315                 320

Lys Arg His Phe Tyr Thr Leu Glu Cys Leu Ser Pro Asp Tyr Ser Trp
                325                 330                 335

Ser Leu Phe Glu Met Ser Ala Phe Gln Lys Gly His Glu Gln Glu Asn
                340                 345                 350

His His Glu Leu Val Asp Ile Gly Lys Lys Ile Val Glu Lys Cys Tyr
            355                 360                 365

Asn Asn Pro Leu Ala Ile Thr Val Val Gly Ser Leu Leu Tyr Gly Glu
        370                 375                 380

Glu Ile Ser Lys Trp Arg Ser Phe Glu Met Ser Glu Leu Ala Lys Ile
385                 390                 395                 400

Gly Asn Gly Asp Asn Lys Ile Leu Pro Ile Leu Lys Leu Ser Tyr His
                405                 410                 415

Asn Leu Ile Pro Ser Leu Lys Ser Cys Phe Ser Tyr Cys Ala Val Phe
                420                 425                 430

Pro Lys Asp His Glu Ile Lys Lys Glu Met Leu Ile Asp Leu Trp Ile
            435                 440                 445

Ala Gln Gly Tyr Val Val Ala Leu Asp Gly Gly Gln Ser Ile Glu Asp
        450                 455                 460

Ala Ala Glu Glu His Phe Val Ile Leu Leu Arg Arg Cys Phe Phe Gln
465                 470                 475                 480

Asp Val Lys Lys Asp Glu Tyr Gly Asp Val Asp Ser Val Lys Ile His
                485                 490                 495

Asp Leu Met His Asp Val Ala Gln Glu Val Gly Arg Glu Glu Ile Cys
            500                 505                 510

Val Val Asn Asp Asn Thr Lys Asn Leu Gly Asp Lys Ile Arg His Val
        515                 520                 525

His Gly Asp Val Asn Arg Tyr Ala Gln Arg Val Ser Leu Cys Ser His
        530                 535                 540

Ser His Lys Ile Arg Ser Tyr Ile Gly Gly Asp Cys Glu Lys Arg Cys
545                 550                 555                 560

Val Asp Thr Leu Ile Asp Lys Trp Met Cys Leu Arg Met Leu Asp Leu
                565                 570                 575

Ser Trp Ser Asp Val Lys Asn Leu Pro Asn Ser Ile Gly Lys Leu Leu
            580                 585                 590

His Leu Arg Tyr Leu Asn Leu Ser Asp Asn Arg Asn Leu Lys Ile Leu
        595                 600                 605

Pro Asp Ala Ile Thr Arg Leu His Asn Leu Gln Thr Leu Leu Leu Lys
    610                 615                 620

Asp Cys Arg Ser Leu Lys Glu Leu Pro Lys Asp Phe Cys Lys Leu Val
625                 630                 635                 640

Lys Leu Arg His Leu Asp Leu Trp Gly Cys Asp Asp Leu Ile Gly Met
                645                 650                 655

Pro Phe Gly Met Asp Lys Leu Thr Ser Leu Arg Ile Leu Pro Asn Ile
            660                 665                 670

Val Val Gly Arg Lys Glu Gln Ser Val Asp Asp Glu Leu Lys Ala Leu
        675                 680                 685

Lys Gly Leu Thr Glu Ile Lys Gly Asp Ile Asp Lys Ile Cys Glu
        690                 695                 700

Asn Tyr Arg Ile Val Glu Gly Met Asn Asp Thr Gly Gly Ala Gly Tyr
705                 710                 715                 720

Leu Lys Ser Met Lys His Leu Arg Glu Ile Gly Ile Thr Phe Asp Gly
```

-continued

```
                725                 730                 735
Gly Cys Val Asn Pro Glu Ala Val Leu Ala Thr Leu Glu Pro Pro Ser
            740                 745                 750
Asn Ile Lys Ser Leu Ser Ile His Arg Phe Asp Gly Lys Thr Leu Pro
            755                 760                 765
Val Trp Gly Arg Ala Glu Ile Asn Trp Ala Ile Ser Leu Ser His Leu
    770                 775                 780
Val Asp Ile Gln Leu Trp His Cys Arg Asn Leu Gln Glu Met Pro Val
785                 790                 795                 800
Leu Ser Lys Leu Pro His Leu Lys Ser Leu Glu Leu Tyr Asn Leu Ile
                805                 810                 815
Ser Leu Glu Tyr Met Glu Ser Thr Ser Arg Ser Ser Ser Asp Thr
            820                 825                 830
Glu Ala Ala Thr Pro Glu Leu Pro Thr Phe Phe Pro Ser Leu Glu Lys
            835                 840                 845
Leu Thr Leu Trp Gly Leu Glu Lys Leu Lys Gly Leu Asn Arg Arg
    850                 855                 860
Ser Ser Ser Phe Pro Arg Leu Ser Glu Leu Lys Ile Met Glu Cys Pro
865                 870                 875                 880
Asp Leu Thr Trp Phe Pro Pro Cys Pro Ser Leu Glu Lys Leu Thr Leu
                885                 890                 895
Trp Arg Leu Asp Lys Leu Lys Gly Phe Gly Asn Arg Arg Ser Ser Thr
            900                 905                 910
Phe Pro Arg Leu Ser Glu Leu Glu Ile Lys Lys Cys Pro Asp Leu Thr
            915                 920                 925
Ser Phe Pro Ser Cys Pro Ser Leu Glu Lys Leu Glu Leu Lys Glu Ser
    930                 935                 940
Asn Glu Ala Leu Gln Ile Ile Val Lys Ile Thr Thr Arg Gly Lys Glu
945                 950                 955                 960
Lys Glu Glu Asn Asn Ala Gly Val Arg Asn Ser Gln Asp Asp
                965                 970                 975
Lys Val Lys Leu Arg Lys Met Val Ile Asp Asn Leu Gly Tyr Leu Lys
            980                 985                 990
Ser Leu Pro Thr Asn Cys Leu Thr His Leu Asp Leu Thr Ile Ser Asp
            995                 1000                1005
Ser Lys Glu Gly Glu Gly Glu Trp Glu Val Gly Asp Ala Phe Gln Lys
    1010                1015                1020
Cys Val Ser Ser Leu Arg Ser Leu Thr Ile Ile Gly Asn His Gly Ile
1025                1030                1035                1040
Asn Lys Val Lys Arg Leu Ser Gly Arg Thr Gly Leu Glu His Phe Thr
            1045                1050                1055
Leu Leu Glu Ser Leu Lys Leu Ser Asp Ile Glu Asp Gln Glu Asp Glu
            1060                1065                1070
Gly Glu Asp Asn Ile Ile Phe Trp Lys Ser Phe Pro Gln Asn Leu Arg
    1075                1080                1085
Ser Leu Arg Ile Lys Asp Ser Asp Lys Met Thr Ser Leu Pro Met Gly
    1090                1095                1100
Met Gln Tyr Leu Thr Ser Leu Gln Thr Leu Tyr Leu His His Cys Tyr
1105                1110                1115                1120
Glu Leu Asn Ser Leu Pro Glu Trp Ile Ser Ser Leu Ser Ser Leu Gln
                1125                1130                1135
Tyr Leu Arg Ile Tyr Tyr Cys Pro Ala Leu Lys Ser Leu Pro Glu Ala
            1140                1145                1150
```

```
Met Arg Asn Leu Thr Ser Leu Gln Thr Leu Gly Ile Ser Asp Cys Pro
        1155                1160                1165

Asp Leu Val Lys Arg Cys Arg Lys Pro Asn Gly Lys Asp Tyr Pro Lys
        1170                1175                1180

Ile Gln His Ile Pro Tyr Trp Ser Ile Glu His Gln Val Leu Asn Glu
1185                1190                1195                1200

Tyr Trp

<210> SEQ ID NO 7
<211> LENGTH: 1213
<212> TYPE: PRT
<213> ORGANISM: Spinacia oleracea

<400> SEQUENCE: 7

Met Ala Glu Ile Gly Tyr Ser Val Cys Ala Lys Leu Ile Glu Val Ile
1               5                   10                  15

Gly Ser Glu Leu Ile Lys Glu Ile Cys Asp Thr Trp Gly Tyr Lys Ser
            20                  25                  30

Leu Leu Glu Asp Leu Asn Lys Thr Val Leu Thr Val Arg Asn Val Leu
        35                  40                  45

Ile Gln Ala Gly Val Met Arg Glu Leu Thr Ser Glu Gln Gln Gly Phe
50                  55                  60

Ile Ala Asp Leu Lys Asp Val Val Tyr Asp Ala Asp Asp Leu Phe Asp
65                  70                  75                  80

Lys Leu Leu Thr Arg Ala Glu Arg Lys Gln Ile Asp Gly Asn Glu Ile
            85                  90                  95

Ser Glu Lys Val Arg Arg Phe Phe Ser Ser Asn Lys Ile Gly Gln
            100                 105                 110

Ala Tyr Tyr Met Ser Arg Lys Val Lys Glu Ile Lys Lys Gln Leu Asp
            115                 120                 125

Glu Ile Val Asp Arg His Thr Lys Phe Gly Phe Ser Ala Glu Phe Ile
130                 135                 140

Pro Val Cys Arg Glu Arg Gly Asn Glu Arg Glu Thr Arg Ser Tyr Ile
145                 150                 155                 160

Asp Val Lys Asn Ile Leu Gly Arg Asp Lys Asp Lys Asn Asp Ile Ile
                165                 170                 175

Asp Arg Leu Leu Asn Arg Asn Gly Asn Glu Ala Cys Ser Phe Leu Thr
            180                 185                 190

Ile Val Gly Ala Gly Gly Leu Gly Lys Thr Ala Leu Ala Gln Leu Val
            195                 200                 205

Phe Asn Asp Glu Arg Val Lys Ile Glu Phe His Asp Leu Arg Tyr Trp
210                 215                 220

Val Cys Val Ser Asp Gln Asp Gly Gly Gln Phe Asp Val Lys Glu Ile
225                 230                 235                 240

Leu Cys Lys Ile Leu Glu Val Val Thr Lys Glu Lys Val Asp Asn Ser
                245                 250                 255

Ser Thr Leu Glu Leu Val Gln Ser Gln Phe Gln Glu Lys Leu Arg Gly
            260                 265                 270

Lys Lys Tyr Phe Leu Val Leu Asp Asp Val Trp Asn Glu Asp Arg Glu
            275                 280                 285

Lys Trp Leu Pro Leu Glu Glu Leu Leu Met Leu Gly Gln Gly Gly Ser
290                 295                 300

Lys Val Val Val Thr Ala Arg Ser Glu Lys Thr Ala Asn Val Ile Gly
305                 310                 315                 320
```

```
Lys Arg His Phe Tyr Thr Leu Glu Cys Leu Ser Pro Asp Tyr Ser Trp
            325                 330                 335

Ser Leu Phe Glu Met Ser Ala Phe Gln Lys Gly His Glu Gln Glu Asn
            340                 345                 350

His His Glu Leu Val Asp Ile Gly Lys Lys Ile Val Glu Lys Cys Tyr
            355                 360                 365

Asn Asn Pro Leu Ala Ile Thr Val Val Gly Ser Leu Leu Tyr Gly Glu
            370                 375                 380

Glu Ile Ser Lys Trp Arg Ser Phe Glu Met Ser Glu Leu Ala Lys Ile
385                 390                 395                 400

Gly Asn Gly Asp Asn Lys Ile Leu Pro Ile Leu Lys Leu Ser Tyr His
            405                 410                 415

Asn Leu Ile Pro Ser Leu Lys Ser Cys Phe Ser Tyr Cys Ala Val Phe
            420                 425                 430

Pro Lys Asp His Glu Ile Lys Lys Glu Met Leu Ile Asp Leu Trp Ile
            435                 440                 445

Ala Gln Gly Tyr Val Val Ala Leu Asp Gly Gly Gln Ser Ile Glu Asp
            450                 455                 460

Ala Ala Glu Glu His Phe Val Ile Leu Leu Arg Arg Cys Phe Phe Gln
465                 470                 475                 480

Asp Val Lys Lys Asp Glu Tyr Gly Asp Val Asp Ser Val Lys Ile His
            485                 490                 495

Asp Leu Met His Asp Val Ala Gln Glu Val Gly Arg Glu Glu Ile Cys
            500                 505                 510

Val Val Asn Asp Asn Thr Lys Asn Leu Gly Asp Lys Ile Arg His Val
            515                 520                 525

His Gly Asp Val Asn Arg Tyr Ala Gln Arg Val Ser Leu Cys Ser His
            530                 535                 540

Ser His Lys Ile Arg Ser Tyr Ile Gly Gly Asp Cys Glu Lys Arg Cys
545                 550                 555                 560

Val Asp Thr Leu Ile Asp Lys Trp Met Cys Leu Arg Met Leu Asp Leu
            565                 570                 575

Ser Trp Ser Asp Val Lys Asn Leu Pro Asn Ser Ile Gly Lys Leu Leu
            580                 585                 590

His Leu Arg Tyr Leu Asn Leu Ser Asp Asn Arg Asn Leu Lys Ile Leu
            595                 600                 605

Pro Asp Ala Ile Thr Arg Leu His Asn Leu Gln Thr Leu Leu Leu Lys
            610                 615                 620

Asp Cys Arg Ser Leu Lys Glu Leu Pro Lys Asp Phe Cys Lys Leu Val
625                 630                 635                 640

Lys Leu Arg His Leu Asp Leu Trp Gly Cys Asp Asp Leu Ile Gly Met
            645                 650                 655

Pro Phe Gly Met Asp Lys Leu Thr Ser Leu Arg Ile Leu Pro Asn Ile
            660                 665                 670

Val Val Gly Arg Lys Glu Gln Ser Val Asp Asp Glu Leu Lys Ala Leu
            675                 680                 685

Lys Gly Leu Thr Glu Ile Lys Gly Asp Ile Asp Ile Lys Ile Cys Glu
            690                 695                 700

Asn Tyr Arg Ile Val Glu Gly Met Asn Asp Thr Gly Ala Gly Tyr
705                 710                 715                 720

Leu Lys Ser Met Lys His Leu Arg Glu Ile Gly Ile Thr Phe Asp Gly
            725                 730                 735
```

-continued

Gly Cys Val Asn Pro Glu Ala Val Leu Ala Thr Leu Glu Pro Pro Ser
            740                 745                 750

Asn Ile Lys Ser Leu Ser Ile His Arg Phe Asp Gly Lys Thr Leu Pro
            755                 760                 765

Val Trp Gly Arg Ala Glu Ile Asn Trp Ala Ile Ser Leu Ser His Leu
    770                 775                 780

Val Asp Ile Gln Leu Trp His Cys Arg Asn Leu Gln Glu Met Pro Val
785                 790                 795                 800

Leu Ser Lys Leu Pro His Leu Lys Ser Leu Glu Leu Tyr Asn Leu Ile
                805                 810                 815

Ser Leu Glu Tyr Met Glu Ser Thr Ser Arg Ser Ser Ser Ser Asp Thr
            820                 825                 830

Glu Ala Ala Thr Pro Glu Leu Pro Thr Phe Phe Pro Ser Leu Glu Lys
            835                 840                 845

Leu Thr Leu Trp Gly Leu Glu Lys Leu Lys Gly Leu Gly Asn Arg Arg
    850                 855                 860

Ser Ser Ser Phe Pro Arg Leu Ser Glu Leu Lys Ile Met Glu Cys Pro
865                 870                 875                 880

Asp Leu Thr Trp Phe Pro Pro Cys Pro Ser Leu Glu Lys Leu Thr Leu
                885                 890                 895

Trp Arg Leu Asp Lys Leu Lys Gly Phe Gly Asn Arg Arg Ser Ser Thr
            900                 905                 910

Phe Pro Arg Leu Ser Glu Leu Glu Ile Lys Lys Cys Pro Asp Leu Thr
            915                 920                 925

Ser Phe Pro Ser Cys Pro Ser Leu Glu Lys Leu Glu Leu Lys Glu Ser
    930                 935                 940

Asn Glu Ala Leu Gln Ile Ile Val Lys Ile Thr Thr Arg Gly Lys Glu
945                 950                 955                 960

Lys Glu Glu Asn Asn Asn Ala Gly Val Arg Asn Ser Gln Asp Asp Asp
                965                 970                 975

Lys Val Lys Leu Arg Lys Met Val Ile Asp Asn Leu Gly Tyr Leu Lys
            980                 985                 990

Ser Leu Pro Thr Asn Cys Leu Thr His Leu Asp Leu Thr Ile Ser Asp
    995                 1000                1005

Ser Lys Glu Gly Glu Gly Glu Trp Glu Val Gly Asp Ala Phe Gln Lys
    1010                1015                1020

Cys Val Ser Ser Leu Arg Ser Leu Thr Ile Ile Gly Asn His Gly Ile
1025                1030                1035                1040

Asn Lys Val Lys Arg Leu Ser Gly Arg Thr Gly Leu Glu His Phe Thr
                1045                1050                1055

Leu Leu Glu Ser Leu Lys Leu Ser Asp Ile Glu Asp Gln Glu Asp Glu
            1060                1065                1070

Gly Glu Asp Asn Ile Ile Phe Trp Lys Ser Phe Pro Gln Asn Leu Arg
            1075                1080                1085

Ser Leu Arg Ile Lys Asp Ser Asp Lys Met Thr Ser Leu Pro Met Gly
    1090                1095                1100

Met Gln Tyr Leu Thr Ser Leu Gln Thr Leu Tyr Leu His His Cys Tyr
1105                1110                1115                1120

Glu Leu Asn Ser Leu Pro Glu Trp Ile Ser Ser Leu Ser Leu Gln
                1125                1130                1135

Tyr Leu Arg Ile Tyr Tyr Cys Pro Ala Leu Lys Ser Leu Pro Glu Ala
            1140                1145                1150

Met Arg Asn Leu Thr Ser Leu Gln Thr Leu Gly Ile Ser Asp Cys Pro

Asp Leu Val Lys Arg Cys Arg Lys Pro Asn Gly Lys Asp Tyr Pro Lys
    1170                       1175                     1180

Ile Gln His Ile Pro Tyr Trp Ser Ile Glu His Gln Leu Leu Asn Thr
1185                 1190                   1195                   1200

Ser Leu Ile Leu Asn Ala Pro Asn Leu Gln Asp Met Asp
           1205                   1210

<210> SEQ ID NO 8
<211> LENGTH: 20
<212> TYPE: DNA
<213> ORGANISM: Spinacia oleracea
<220> FEATURE:
<223> OTHER INFORMATION: Forward primer

<400> SEQUENCE: 8
acaagtggat gtgtcttagg                                                 20

<210> SEQ ID NO 9
<211> LENGTH: 19
<212> TYPE: DNA
<213> ORGANISM: Spinacia oleracea
<220> FEATURE:
<223> OTHER INFORMATION: Reverse primer

<400> SEQUENCE: 9
ttcgccctca tcttcctgg                                                  19

<210> SEQ ID NO 10
<211> LENGTH: 18
<212> TYPE: DNA
<213> ORGANISM: Spinacia oleracea
<220> FEATURE:
<223> OTHER INFORMATION: Forward primer

<400> SEQUENCE: 10
tcacgtgggt tgtgttgt                                                   18

<210> SEQ ID NO 11
<211> LENGTH: 1526
<212> TYPE: DNA
<213> ORGANISM: Spinacia oleracea
<220> FEATURE:
<223> OTHER INFORMATION: Amplicon

<400> SEQUENCE: 11
acaagtggat gtgtcttagg atgttggact tgtcatggtc ggatgttaaa aatttgccta    60
attcaatagg taaattgttg cacttgaggt atcttaacct gtcagataat agaaatctaa   120
agatacttcc tgatgcaatt acaagactgc ataatttgca gacactgctt ttaaaagatt   180
gcagaagttt aaaggagttg ccaaaagatt tttgcaaatt ggtcaaactg agacacttgg   240
atttatgggg ttgtgatgat ttgattggta tgccatttgg aatggataag ctaactagtc   300
ttagaatact accaaacatt gtggtgggta ggaaggaaca aagtgttgat gatgagctga   360
aagcccttaa aggcctcacc gagataaaag gcgacattga tatcaaaatc tgtgaaaatt   420
atagaatagt tgaaggcatg aatgacacag gaggagctgg gtatttgaag agcatgaaac   480
atctcaggga gattggtatt acatttgatg gtggatgtgt taaccctgaa gctgtgttgg   540
caaccctaga gccaccttca aatatcaaga gcttatctat acatcgtttt gatggtaaaa   600
cacttccagt atggggaaga gcagagatta attgggcaat ctccctctca catcttgtcg   660

```
acatccagct ttggcattgt cgtaatttgc aggagatgcc agtgctgagt aaactgcctc    720
atttgaaatc actggaactt tataatttga ttagtttaga gtacatggag agcacaagca    780
gaagcagtag cagtgacaca gaagcagcaa caccagaatt accaacattc ttcccttccc    840
ttgaaaaact tacactttgg ggtctggaaa agttgaaggg tttggggaac aggagatcga    900
gtagttttcc ccgcctctct gaattgaaaa tcatggaatg cccagatcta acgtggtttc    960
ctccctgtcc aagccttgaa aaacttacac tttggcgtct ggacaagttg aagggttttg   1020
ggaaccggag atcgagtact ttccccgcc tctctgaatt ggaaatcaag aaatgcccag   1080
atctaacgtc atttccttct tgtccaagcc ttgagaagtt ggaattgaaa gaaagcaatg   1140
aagcattgca aataatagta aaaataacaa caagaggtaa agaaaagaa gagaacaata    1200
atgctggtgt tagaaattca caagatgatg acaaagtcaa attacggaag atggtgatag   1260
acaatctggg ttatctcaaa tcactgccca caaattgtct tactccacctc gaccttacaa   1320
taagtgattc caaggagggg gagggtgaat gggaagttgg ggatgcattt cagaagtgtg   1380
tatcttcttt gagaagcctc accataatcg gaaatcacgg aataaataaa gtgaagagac   1440
tgtctggaag aacagggttg gagcatttca ctctgttgga atcactcaaa ctttcagata   1500
tagaagacca ggaagatgag ggcgaa                                        1526
```

<210> SEQ ID NO 12
<211> LENGTH: 508
<212> TYPE: PRT
<213> ORGANISM: Spinacia oleracea
<220> FEATURE:
<223> OTHER INFORMATION: Amino acid sequence encoded by amplicon

<400> SEQUENCE: 12

```
Lys Trp Met Cys Leu Arg Met Leu Asp Leu Ser Trp Ser Asp Val Lys
1               5                   10                  15

Asn Leu Pro Asn Ser Ile Gly Lys Leu Leu His Leu Arg Tyr Leu Asn
            20                  25                  30

Leu Ser Asp Asn Arg Asn Leu Lys Ile Leu Pro Asp Ala Ile Thr Arg
        35                  40                  45

Leu His Asn Leu Gln Thr Leu Leu Lys Asp Cys Arg Ser Leu Lys
    50                  55                  60

Glu Leu Pro Lys Asp Phe Cys Lys Leu Val Lys Leu Arg His Leu Asp
65                  70                  75                  80

Leu Trp Gly Cys Asp Asp Leu Ile Gly Met Pro Phe Gly Met Asp Lys
                85                  90                  95

Leu Thr Ser Leu Arg Ile Leu Pro Asn Ile Val Val Gly Arg Lys Glu
            100                 105                 110

Gln Ser Val Asp Asp Glu Leu Lys Ala Leu Lys Gly Leu Thr Glu Ile
        115                 120                 125

Lys Gly Asp Ile Asp Ile Lys Ile Cys Glu Asn Tyr Arg Ile Val Glu
    130                 135                 140

Gly Met Asn Asp Thr Gly Gly Ala Gly Tyr Leu Lys Ser Met Lys His
145                 150                 155                 160

Leu Arg Glu Ile Gly Ile Thr Phe Asp Gly Gly Cys Val Asn Pro Glu
                165                 170                 175

Ala Val Leu Ala Thr Leu Glu Pro Pro Ser Asn Ile Lys Ser Leu Ser
            180                 185                 190

Ile His Arg Phe Asp Gly Lys Thr Leu Pro Val Trp Gly Arg Ala Glu
        195                 200                 205
```

Ile Asn Trp Ala Ile Ser Leu Ser His Leu Val Asp Ile Gln Leu Trp
210                 215                 220

His Cys Arg Asn Leu Gln Glu Met Pro Val Leu Ser Lys Leu Pro His
225                 230                 235                 240

Leu Lys Ser Leu Glu Leu Tyr Asn Leu Ile Ser Leu Glu Tyr Met Glu
            245                 250                 255

Ser Thr Ser Arg Ser Ser Ser Asp Thr Glu Ala Ala Thr Pro Glu
            260                 265                 270

Leu Pro Thr Phe Phe Pro Ser Leu Glu Lys Leu Thr Leu Trp Gly Leu
            275                 280                 285

Glu Lys Leu Lys Gly Leu Gly Asn Arg Arg Ser Ser Ser Phe Pro Arg
290                 295                 300

Leu Ser Glu Leu Lys Ile Met Glu Cys Pro Asp Leu Thr Trp Phe Pro
305                 310                 315                 320

Pro Cys Pro Ser Leu Glu Lys Leu Thr Leu Trp Arg Leu Asp Lys Leu
            325                 330                 335

Lys Gly Phe Gly Asn Arg Arg Ser Ser Thr Phe Pro Arg Leu Ser Glu
            340                 345                 350

Leu Glu Ile Lys Lys Cys Pro Asp Leu Thr Ser Phe Pro Ser Cys Pro
            355                 360                 365

Ser Leu Glu Lys Leu Glu Leu Lys Glu Ser Asn Glu Ala Leu Gln Ile
370                 375                 380

Ile Val Lys Ile Thr Thr Arg Gly Lys Glu Lys Glu Asn Asn Asn
385                 390                 395                 400

Ala Gly Val Arg Asn Ser Gln Asp Asp Lys Val Lys Leu Arg Lys
            405                 410                 415

Met Val Ile Asp Asn Leu Gly Tyr Leu Lys Ser Leu Pro Thr Asn Cys
            420                 425                 430

Leu Thr His Leu Asp Leu Thr Ile Ser Asp Ser Lys Glu Gly Glu Gly
            435                 440                 445

Glu Trp Glu Val Gly Asp Ala Phe Gln Lys Cys Val Ser Ser Leu Arg
450                 455                 460

Ser Leu Thr Ile Ile Gly Asn His Gly Ile Asn Lys Val Lys Arg Leu
465                 470                 475                 480

Ser Gly Arg Thr Gly Leu Glu His Phe Thr Leu Leu Glu Ser Leu Lys
            485                 490                 495

Leu Ser Asp Ile Glu Asp Gln Glu Asp Glu Gly Glu
            500                 505

<210> SEQ ID NO 13
<211> LENGTH: 1597
<212> TYPE: DNA
<213> ORGANISM: Spinacia oleracea
<220> FEATURE:
<223> OTHER INFORMATION: Amplicon

<400> SEQUENCE: 13
tcacgtgggt tgtgttgtcg atagagatcc agaaatagtc tttttatgta gcaataagat    60
tcgttcgtat attagcggtc gctgcataaa gaatccggtg gattcacaaa tagacaactg   120
gatgtgcctt agggtgttgg acttgtcaga ttcatgtgtt aaagatttgt ctgattcaat   180
aggtaagctg ctgcacttaa ggtatcttaa cctctcttct aatataaagt tggagataat   240
ccctgatgca attacaagac tgcataactt gcagacacta cttttagaag attgcagaag   300
tttaaaggag ttgccaaaag attttgcaa attggtcaaa ctgaggcact tggaattaca    360

```
gggttgtcat gatttgattg gtatgtcatt tggaatggat aagctaacta gtcttagaat    420
actaccaaac attgtggtgg gtaggaagga acaaagtgtt gatgatgagc tgaaagccct    480
aaaaggcctc accgagataa aaggctccat tgatatcaca atctattcaa aatatagaag    540
agttgaaggc atgaatggca caggaggagg agctgggtat ttgaagagca tgaaacatct    600
cacgggggtt aatattacat ttgatgaagg tggatgtgtt aaccctgaag ctgtgtattt    660
gaagagcatg aaacatctca cgagggttat tattatattt gattataaag gtggatgtgt    720
taaccctgaa gctgtgttgg caaccctaga gccaccttca aatatcaaga ggttagagat    780
gtggcattac agtggtacaa caattccagt atggggaaga gcagagatta attgggcaat    840
ctccctctca catcttgtcg acatcacgct tgaagattgt acaatttgc aggagatgcc     900 agtgctgagt aaactgcctc atttgaaatc actggaactt acagagttgg ataacttaga    960
gtacatggag agtagaagca gcagcagtag cagtgacaca gaagcagcaa caccagaatt   1020
accaacattc ttcccttccc ttgaaaaact tacactttgg cgtctggaca gttgaagggg   1080
ttttgggaac aggagatcga gtagttttcc ccgcctctct aaattggaaa tctggaaatg   1140
tccagatcta acgtcatttc cttcttgtcc aagccttgaa gagttggaat tgaaagaaaa   1200
caatgaagcg ttgcaaataa tagtaaaaat aacaacaaca agaggtaaag aagaaaaaga   1260
agaagacaag aatgctggtg ttggaaattc acaagatgat gacaatgtca aattatggaa   1320
ggtggaaata gacaatctgg gttatctcaa atcactgccc acaaattgtc tgactcacct   1380
cgaccttaca ataagtgatt ccaaggaggg ggagggtgaa tgggaagttg gggatgcatt   1440
tcagaagtgt gtatcttctt tgagaagcct caccataatc ggaaatcacg gaataaataa   1500
agtgaagaga ctgtctggaa gaacagggtt ggagcatttc actctgttgg aatcactcaa   1560
actttcagat atagaagacc aggaagatga gggcgaa                            1597
```

<210> SEQ ID NO 14
<211> LENGTH: 532
<212> TYPE: PRT
<213> ORGANISM: Spinacia oleracea
<220> FEATURE:
<223> OTHER INFORMATION: Amino acid sequence encoded by amplicon

<400> SEQUENCE: 14

```
His Val Gly Cys Val Val Asp Arg Asp Pro Glu Ile Val Phe Leu Cys
1               5                   10                  15

Ser Asn Lys Ile Arg Ser Tyr Ile Ser Gly Arg Cys Ile Lys Asn Pro
            20                  25                  30

Val Asp Ser Gln Ile Asp Asn Trp Met Cys Leu Arg Val Leu Asp Leu
        35                  40                  45

Ser Asp Ser Cys Val Lys Asp Leu Ser Asp Ser Ile Gly Lys Leu Leu
    50                  55                  60

His Leu Arg Tyr Leu Asn Leu Ser Ser Asn Ile Lys Leu Glu Ile Ile
65                  70                  75                  80

Pro Asp Ala Ile Thr Arg Leu His Asn Leu Gln Thr Leu Leu Leu Glu
                85                  90                  95

Asp Cys Arg Ser Leu Lys Glu Leu Pro Lys Asp Phe Cys Lys Leu Val
            100                 105                 110

Lys Leu Arg His Leu Glu Leu Gln Gly Cys His Asp Leu Ile Gly Met
        115                 120                 125

Ser Phe Gly Met Asp Lys Leu Thr Ser Leu Arg Ile Leu Pro Asn Ile
    130                 135                 140
```

Val Val Gly Arg Lys Glu Gln Ser Val Asp Asp Glu Leu Lys Ala Leu
145                 150                 155                 160

Lys Gly Leu Thr Glu Ile Lys Gly Ser Ile Asp Ile Thr Ile Tyr Ser
            165                 170                 175

Lys Tyr Arg Arg Val Glu Gly Met Asn Gly Thr Gly Gly Ala Gly
        180                 185                 190

Tyr Leu Lys Ser Met Lys His Leu Thr Gly Val Asn Ile Thr Phe Asp
        195                 200                 205

Glu Gly Gly Cys Val Asn Pro Glu Ala Val Tyr Leu Lys Ser Met Lys
210                 215                 220

His Leu Thr Arg Val Ile Ile Ile Phe Asp Tyr Lys Gly Gly Cys Val
225                 230                 235                 240

Asn Pro Glu Ala Val Leu Ala Thr Leu Glu Pro Ser Asn Ile Lys
            245                 250                 255

Arg Leu Glu Met Trp His Tyr Ser Gly Thr Thr Ile Pro Val Trp Gly
            260                 265                 270

Arg Ala Glu Ile Asn Trp Ala Ile Ser Leu Ser His Leu Val Asp Ile
            275                 280                 285

Thr Leu Glu Asp Cys Tyr Asn Leu Gln Glu Met Pro Val Leu Ser Lys
290                 295                 300

Leu Pro His Leu Lys Ser Leu Glu Leu Thr Glu Leu Asp Asn Leu Glu
305                 310                 315                 320

Tyr Met Glu Ser Arg Ser Ser Ser Ser Asp Thr Glu Ala Ala
            325                 330                 335

Thr Pro Glu Leu Pro Thr Phe Phe Pro Ser Leu Glu Lys Leu Thr Leu
            340                 345                 350

Trp Arg Leu Asp Lys Leu Lys Gly Phe Gly Asn Arg Arg Ser Ser Ser
            355                 360                 365

Phe Pro Arg Leu Ser Lys Leu Glu Ile Trp Lys Cys Pro Asp Leu Thr
            370                 375                 380

Ser Phe Pro Ser Cys Pro Ser Leu Glu Glu Leu Glu Leu Lys Glu Asn
385                 390                 395                 400

Asn Glu Ala Leu Gln Ile Ile Val Lys Ile Thr Thr Thr Arg Gly Lys
            405                 410                 415

Glu Glu Lys Glu Glu Asp Lys Asn Ala Gly Val Gly Asn Ser Gln Asp
            420                 425                 430

Asp Asp Asn Val Lys Leu Trp Lys Val Glu Ile Asp Asn Leu Gly Tyr
            435                 440                 445

Leu Lys Ser Leu Pro Thr Asn Cys Leu Thr His Leu Asp Leu Thr Ile
450                 455                 460

Ser Asp Ser Lys Glu Gly Glu Gly Glu Trp Glu Val Gly Asp Ala Phe
465                 470                 475                 480

Gln Lys Cys Val Ser Ser Leu Arg Ser Leu Thr Ile Ile Gly Asn His
            485                 490                 495

Gly Ile Asn Lys Val Lys Arg Leu Ser Gly Arg Thr Gly Leu Glu His
            500                 505                 510

Phe Thr Leu Leu Glu Ser Leu Lys Leu Ser Asp Ile Glu Asp Gln Glu
            515                 520                 525

Asp Glu Gly Glu
    530

<210> SEQ ID NO 15
<211> LENGTH: 9
<212> TYPE: PRT

```
<213> ORGANISM: Spinacia oleracea
<220> FEATURE:
<223> OTHER INFORMATION: motif N-terminus

<400> SEQUENCE: 15

Met Ala Glu Ile Gly Tyr Ser Val Cys
1               5

<210> SEQ ID NO 16
<211> LENGTH: 6
<212> TYPE: PRT
<213> ORGANISM: Spinacia oleracea
<220> FEATURE:
<223> OTHER INFORMATION: motif

<400> SEQUENCE: 16

Lys Trp Met Cys Leu Arg
1               5

<210> SEQ ID NO 17
<211> LENGTH: 8
<212> TYPE: PRT
<213> ORGANISM: Spinacia oleracea
<220> FEATURE:
<223> OTHER INFORMATION: motif

<400> SEQUENCE: 17

His Val Gly Cys Val Val Asp Arg
1               5

<210> SEQ ID NO 18
<211> LENGTH: 9
<212> TYPE: PRT
<213> ORGANISM: Spinacia oleracea
<220> FEATURE:
<223> OTHER INFORMATION: additional motif

<400> SEQUENCE: 18

Asp Gln Glu Asp Glu Gly Glu Asp Asn
1               5

<210> SEQ ID NO 19
<211> LENGTH: 30
<212> TYPE: DNA
<213> ORGANISM: Spinacia oleracea
<220> FEATURE:
<223> OTHER INFORMATION: Standard amplification sequence forward primer

<400> SEQUENCE: 19
gcagtcgaac atgtagctga ctcaggtcac                                      30

<210> SEQ ID NO 20
<211> LENGTH: 30
<212> TYPE: DNA
<213> ORGANISM: Spinacia oleracea
<220> FEATURE:
<223> OTHER INFORMATION: standard amplification sequence reverse primer

<400> SEQUENCE: 20
tggatcactt gtgcaagcat cacatcgtag                                      30
```